(12) United States Patent
Chukka et al.

(10) Patent No.: US 11,823,347 B2
(45) Date of Patent: Nov. 21, 2023

(54) LINE-BASED IMAGE REGISTRATION AND CROSS-IMAGE ANNOTATION DEVICES, SYSTEMS AND METHODS

(71) Applicant: Ventana Medical Systems, Inc., Tucson, AZ (US)

(72) Inventors: Srinivas Chukka, San Jose, CA (US); Anindya Sarkar, Milpitas, CA (US); Quan Yuan, San Jose, CA (US)

(73) Assignee: VENTANA MEDICAL SYSTEMS, INC., Tucson, AZ (US)

( * ) Notice: Subject to any disclaimer, the term of this patent is extended or adjusted under 35 U.S.C. 154(b) by 313 days.

(21) Appl. No.: 17/192,967

(22) Filed: Mar. 5, 2021

(65) Prior Publication Data

US 2021/0233206 A1    Jul. 29, 2021

Related U.S. Application Data

(60) Continuation of application No. 16/706,630, filed on Dec. 6, 2019, now Pat. No. 10,977,766, which is a
(Continued)

(51) Int. Cl.
*G16H 30/40* (2018.01)
*G06T 3/00* (2006.01)
(Continued)

(52) U.S. Cl.
CPC .............. *G06T 3/0068* (2013.01); *G06T 7/33* (2017.01); *G06V 20/695* (2022.01); *G16H 30/20* (2018.01);
(Continued)

(58) Field of Classification Search
None
See application file for complete search history.

(56) References Cited

U.S. PATENT DOCUMENTS 6,061,476 A    5/2000    Nichani
6,251,615 B1   6/2001    Oberhardt
(Continued)

FOREIGN PATENT DOCUMENTS

EP    2634749 A2    4/2013
JP    2000342558 A  12/2000
WO    2011163624 A1 12/2011

OTHER PUBLICATIONS

Image Registration—Wikipedia, Available online at https://en.wikipedia.org/w/index.php?title=Image_registration&oldid=562394204, Jul. 1, 2013, pp. 1-4.
(Continued)

*Primary Examiner* — Tsung Yin Tsai
(74) *Attorney, Agent, or Firm* — Kilpatrick Townsend & Stockton LLP

(57) ABSTRACT

The disclosure relates to devices, systems and methods for image registration and annotation. The devices include computer software products for aligning whole slide digital images on a common grid and transferring annotations from one aligned image to another aligned image on the basis of matching tissue structure. The systems include computer-implemented systems such as work stations and networked computers for accomplishing the tissue-structure based image registration and cross-image annotation. The methods include processes for aligning digital images corresponding to adjacent tissue sections on a common grid based on tissue structure, and transferring annotations from one of the adjacent tissue images to another of the adjacent tissue images. The basis for alignment may be a line-based registration process, wherein sets of lines are computed on the boundary regions computed for the two images, where the boundary regions are obtained using information from two domains—soft-weighted foreground images and gradient magnitude images. The binary mask image, based on whose
(Continued)

boundary the line features are computed, may be generated by combining two binary masks—a first binary mask is obtained on thresholding a soft-weighted (continuous valued) foreground image, which is computed based on the stain content in an image, while a second binary mask is obtained after thresholding a gradient magnitude domain image, where the gradient is computed from the grayscale image obtained from the color image.

17 Claims, 43 Drawing Sheets

Related U.S. Application Data division of application No. 15/087,753, filed on Mar. 31, 2016, now Pat. No. 10,503,868, which is a continuation of application No. PCT/EP2014/070927, filed on Sep. 30, 2014.

(60) Provisional application No. 61/885,024, filed on Oct. 1, 2013.

(51) Int. Cl.
G06T 7/33 (2017.01)
G16H 30/20 (2018.01)
G06V 20/69 (2022.01)

(52) U.S. Cl.
CPC ... G16H 30/40 (2018.01); G06T 2207/10024 (2013.01); G06T 2207/10056 (2013.01); G06T 2207/10064 (2013.01); G06T 2207/20016 (2013.01); G06T 2207/30024 (2013.01)

(56) References Cited

U.S. PATENT DOCUMENTS

| | | | |
|---|---|---|---|
| 7,783,096 B2 * | 8/2010 | Chen | G06T 7/207 382/128 |
| 7,899,624 B2 | 3/2011 | Cualing et al. | |
| 8,131,476 B2 | 3/2012 | Cline et al. | |
| 8,463,006 B2 * | 6/2013 | Prokoski | G16H 30/20 382/128 |
| 8,771,188 B2 * | 7/2014 | Schers | A61B 8/483 600/595 |
| 9,818,190 B2 | 11/2017 | Chukka | |
| 10,290,111 B2 * | 5/2019 | Jia | G06T 3/0012 |
| 10,503,868 B2 | 12/2019 | Chukka et al. | |
| 10,977,766 B2 | 4/2021 | Chukka et al. | |
| 10,977,791 B2 * | 4/2021 | Chukka | G06T 7/0012 |
| 2003/0118222 A1 | 6/2003 | Foran et al. | |
| 2006/0120583 A1 * | 6/2006 | Dewaele | G06T 7/35 382/128 |
| 2008/0166036 A1 | 7/2008 | Bloom et al. | |
| 2009/0018445 A1 * | 1/2009 | Schers | A61B 8/483 600/437 |
| 2009/0028614 A1 | 1/2009 | Kerxhalli et al. | |
| 2010/0000383 A1 | 1/2010 | Koos et al. | |
| 2010/0054560 A1 | 3/2010 | Yamashita et al. | |
| 2010/0172567 A1 * | 7/2010 | Prokoski | A61B 5/0064 348/47 |
| 2011/0040169 A1 | 2/2011 | Kamen et al. | |
| 2012/0076390 A1 | 3/2012 | Potts et al. | |
| 2012/0082362 A1 | 4/2012 | Diem et al. | |
| 2012/0328178 A1 | 12/2012 | Remiszewski | |
| 2013/0089249 A1 | 4/2013 | Mueller et al. | |
| 2013/0156279 A1 | 6/2013 | Schoenmeyer et al. | |
| 2013/0230220 A1 | 9/2013 | Yu et al. | |
| 2013/0294697 A1 * | 11/2013 | Nepomniachtchi | G06Q 20/10 382/192 |
| 2014/0212037 A1 | 7/2014 | Sasaki | |
| 2016/0019695 A1 | 1/2016 | Chukka et al. | |
| 2016/0148435 A1 * | 5/2016 | Li | G06F 3/0482 715/848 |
| 2016/0321495 A1 | 11/2016 | Chukka | |
| 2016/0321809 A1 | 11/2016 | Chukka | |
| 2017/0103521 A1 | 4/2017 | Chukka et al. | |
| 2017/0309021 A1 | 10/2017 | Barnes et al. | |
| 2017/0322124 A1 * | 11/2017 | Barnes | G06T 7/33 |
| 2017/0328817 A1 | 11/2017 | Barnes | |
| 2018/0033155 A1 * | 2/2018 | Jia | G06T 3/0093 |
| 2018/0356624 A1 * | 12/2018 | Isobe | H01J 37/16 |
| 2019/0376878 A1 | 12/2019 | Barnes | |
| 2019/0392578 A1 * | 12/2019 | Chukka | G06V 20/698 |
| 2020/0226462 A1 | 7/2020 | Maddison et al. | |
| 2020/0302603 A1 | 9/2020 | Barnes | |
| 2020/0372235 A1 | 11/2020 | Peng | |
| 2021/0233206 A1 * | 7/2021 | Chukka | G16H 30/40 |

OTHER PUBLICATIONS

U.S. Appl. No. 15/087,753, Non-Final Office Action dated Mar. 15, 2018, 11 pages.
U.S. Appl. No. 15/087,753, Notice of Allowance dated Jul. 15, 2019, 10 pages.
U.S. Appl. No. 15/087,753, Notice of Allowance dated Dec. 28, 2018, 9 pages.
U.S. Appl. No. 16/706,630, Notice of Allowance dated Dec. 4, 2020, 12 pages.
European Application No. 14780824.0, Office Action dated Jun. 7, 2017, 4 pages.
European Application No. 14780824.0, Office Action dated Mar. 20, 2019, 5 pages.
Otsu et al., A Threshold Selection Method from Gray-Level Histograms, Automatica 11.285-296, 1975, pp. 23-27.
Borgefors, Gunilla, "Distance Transformations in Digital Images, Computer vision, Graphics, and Image Processing", 1986, pp. 344-371, vol. 34.
Canny, John, "A Computational Approach to Edge Detection, IEEE Transactions on Pattern Analysis and Machine Intelligence", Nov. 1986, pp. 679-698, vol. 8, No. 6.
Chappelow, J. et. al. "HistoStitcher ©: An Interactive Program for Accurate and Rapid Reconstruction of Digitized Whole Histological Sections From Tissue Fragments." Computerized Medical Imaging and Graphics, vol. 35, No. 7, pp. 557-567 2011).
Hu, M. "Visual Pattern Recognition by Moment Invariants." IRE Transactions on Information Theory, vol. 8, No. 2, pp. 179-187, (1962).
International Search Report & Written Opinion dated Sep. 23, 2014 in corresponding International Application No. PCT/EP2014/054781, all pgs.
Ma, T. et al. "Boosting Chamfer Matching by Learning Chamfer Distance Normalization." Computer Vision—ECCV 2010, Part V, LNCS 6315, pp. 450-463, (2010).
Wei, et. al., "A Hierarchical Approach for Image Registration Using Line Features, Proceedings of SPIE", 2008, p. 72851H-1-72851H-7, vol. 7285.
LV, Guohuna, et. al. "Maximizing Structural Similarity in Multimodal Biomedical Microscopic Images for Effective Registration", presented at 2013 IEEE International Conference on Multimedia and Expo {ICME) and published on Sep. 26, 2013 {pp. 1-6).
Anonymous, "Image Registration, Wikipedia", (Jul. 1, 2013), pp. 1-4, retrieved from the Internet URL:https://en.Wikipedia.org/w/index.php?title=Image_registration&oldid=562394204 [retrieved on May 30, 2017].
Fischler, et. al., "Random Sample Consensus: a Paradigm for Model Fitting with Applications to Image Analysis and Automated Cartography", Communications ofthe ACMI, Jun. 1981, pp. 381-395, vol. 24, No. 6.
Eldad Haber, et. al.: "Intensity Gradient Based Registration and Fusion of Multi-modal Images", Jan. 1, 2006 (Jan. 1, 2006 ),Medical Image Computing and Computer Assisted Intervention—MICCAI 2006 Lecture Notes in Computer Science LNCS, Springer, Berlin, DE, pp. 726-733, XP019043650,ISBN: 978-3-540-44727-6.

(56) References Cited

OTHER PUBLICATIONS

Otsu, "A Threshold Selection Method from Gray-Level Histograms, IEEE Transactions on Systems", Man, and Cybernetics, Jan. 1979, pp. 62-66, vol. SMC-9, No. 1.
International Search Report and Written Opinion dated Feb. 16, 2015 received in corresponding PCT Application No. PCT/EP2014/070927.
Samet, et. al., "An Improved Approach to Connected Component Labeling of Images", Proceedings, IEEE Computer Society Press, 1986, pp. 312-318.
Tae, et. al., "Multimodal Microscopy for Automated Histologic Microscopy for Automated Histologic Analysis of Prostate Cancer", BMC Cancer, Biomed Central, 2001, p. 62, vol. 11, No. 1.
Zhang, et. al., "Perceptual Object Extraction Based on Saliency and Clustering", Journal of Multimedia, Aug. 1, 2010, vol. 5, No. 4.
Issue Notification mailed in U.S. Appl. No. 15/087,753 dated Nov. 21, 2019, all pgs.
International Search Report and Written Opinion dated Apr. 9, 2015 in application No. PCT/EP2014/070927, all pgs.
Notice of Allowance dated Jul. 27, 2020 in application No. CA 2920494, all pgs.
Decision to Grant Patent dated Sep. 24, 2020 in application No. EP14780824.0, all pgs.
Ruifrok AC, Johnston DA, Quantification of Histological Staining by Color Deconvolution, Analytical and Quantitative Cytology Histology 23: 291-299, 2001.
Lippolis, et. al. "Automatic Registration of Multi-Modal Microscopy Images for Integrative Analysis of Prostate Issue Sections", BMC Cancer, 2013, all pgs.

\* cited by examiner

Foreground extraction through color deconvolution

HE image

Hematoxylin component

Eosin component

Weighted FG image

IHC image

Soft weighted foreground image extracted
From IHC image in Fig. 17(a)

Binary mask obtained by OR-ing both masks
Line segments obtained along boundary of image
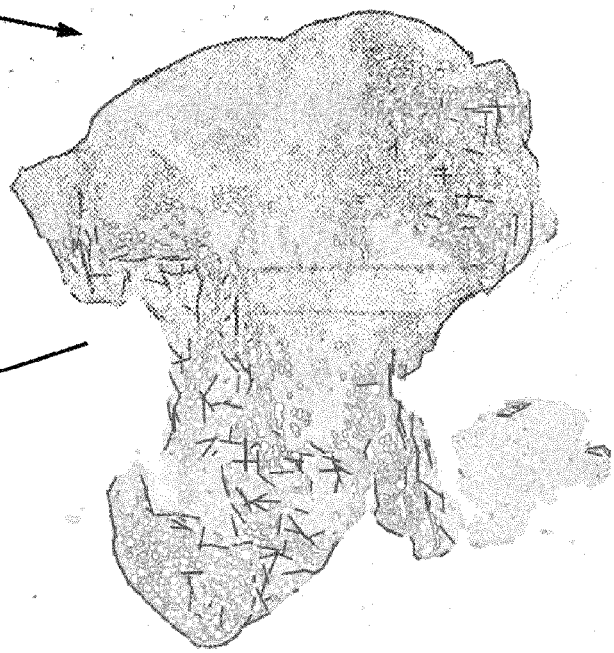
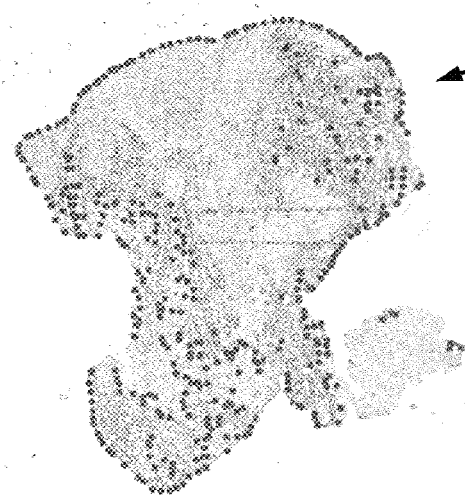
Line centers plotted at centers of line segments
FIG.19

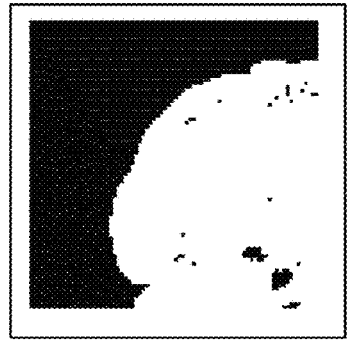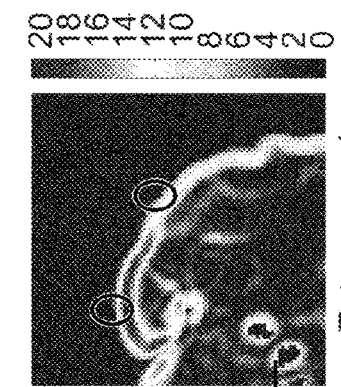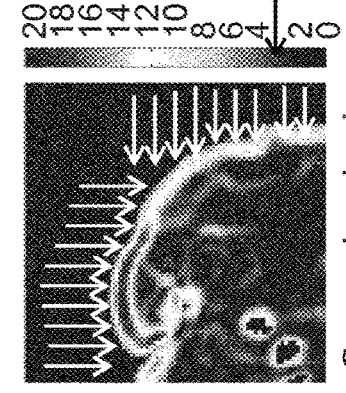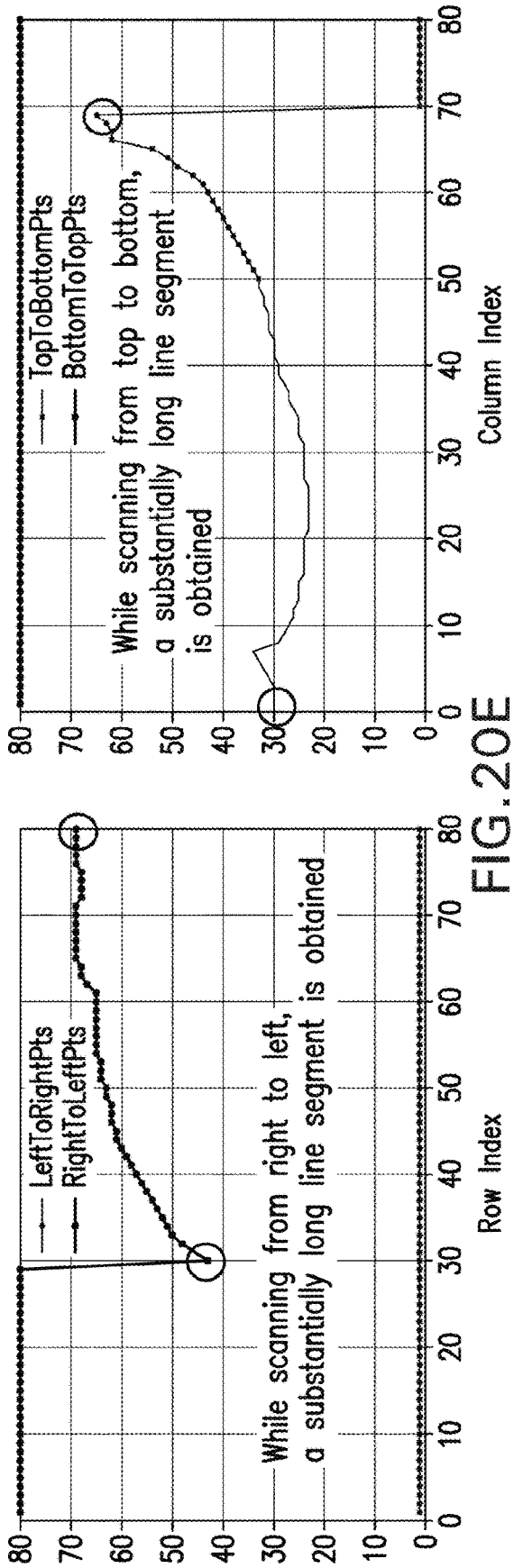
FIG. 20E

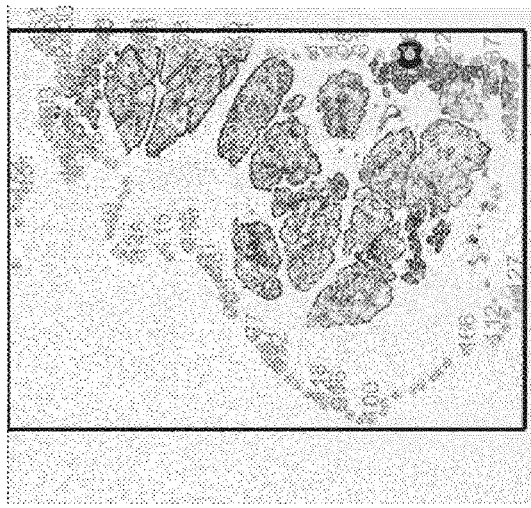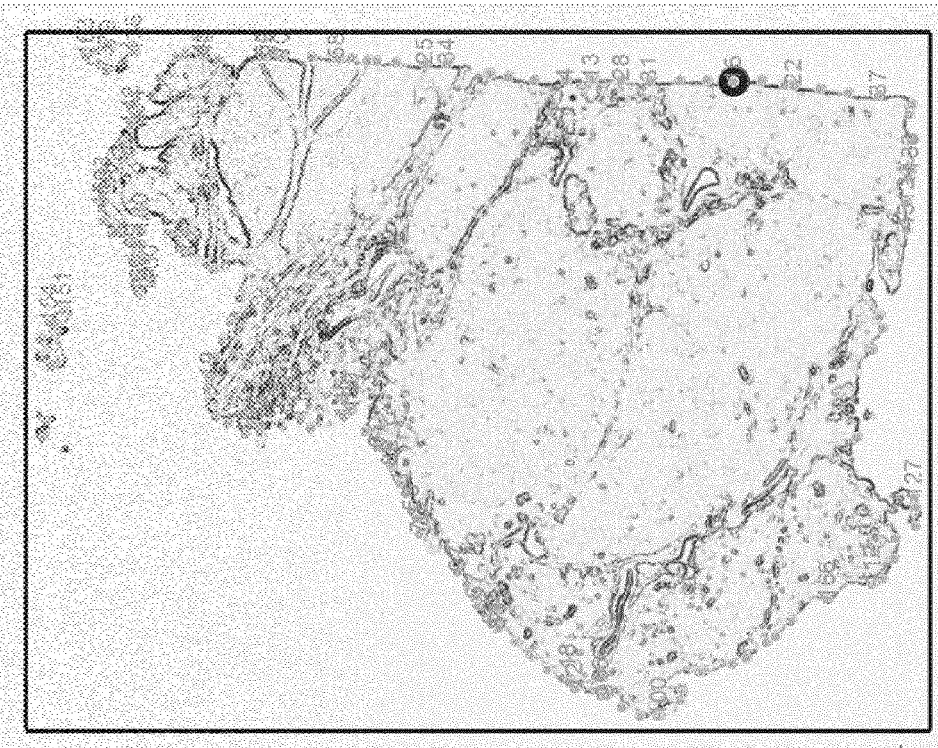
FIG. 21A

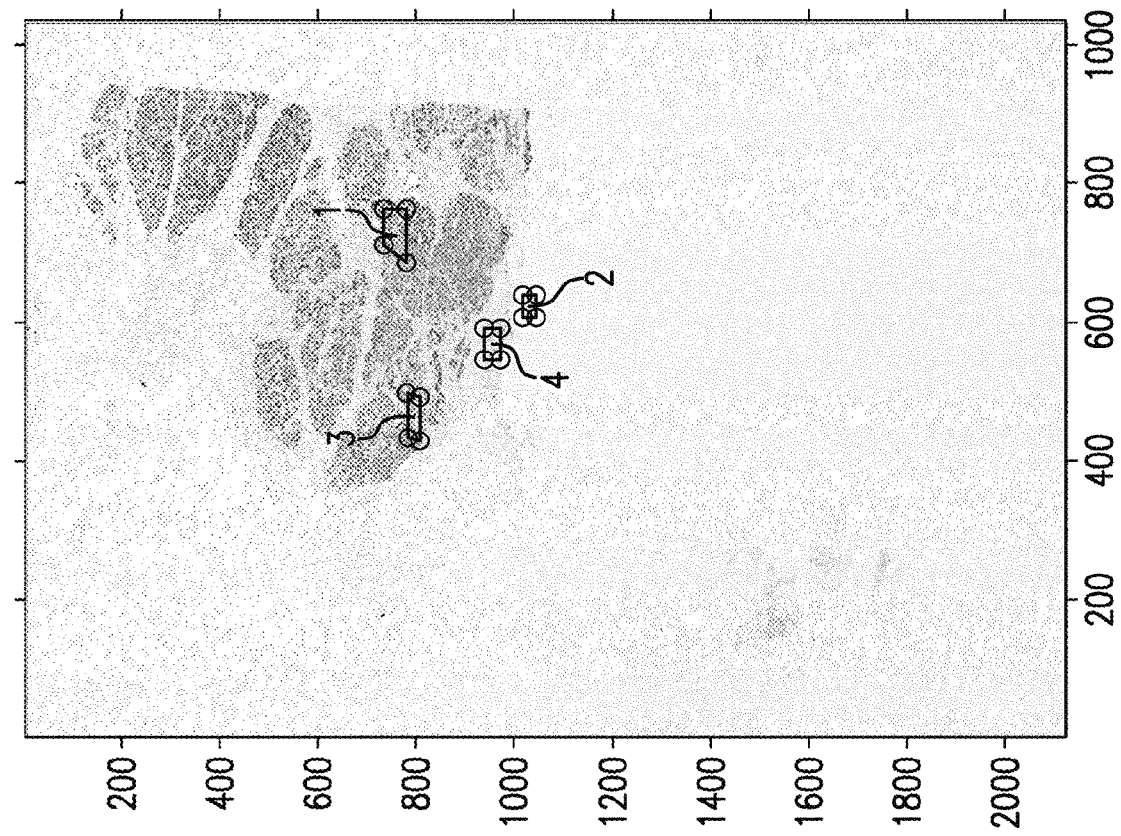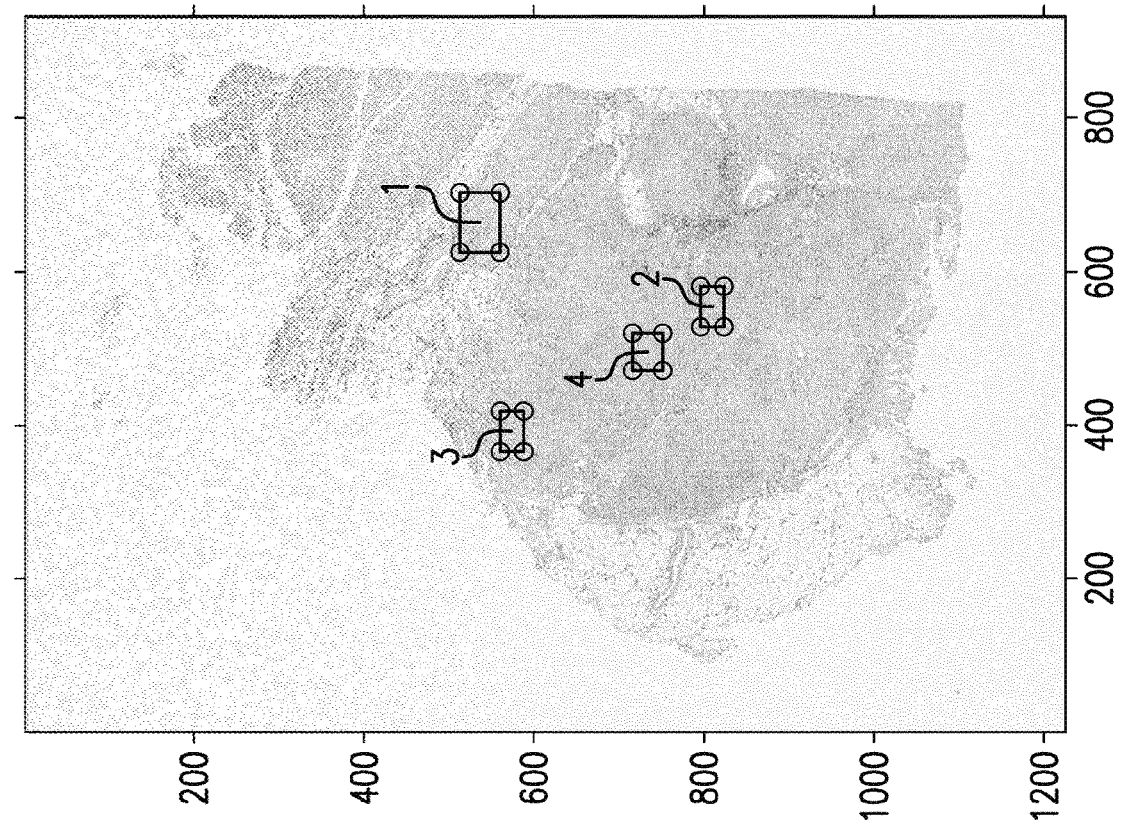
FIG. 21B

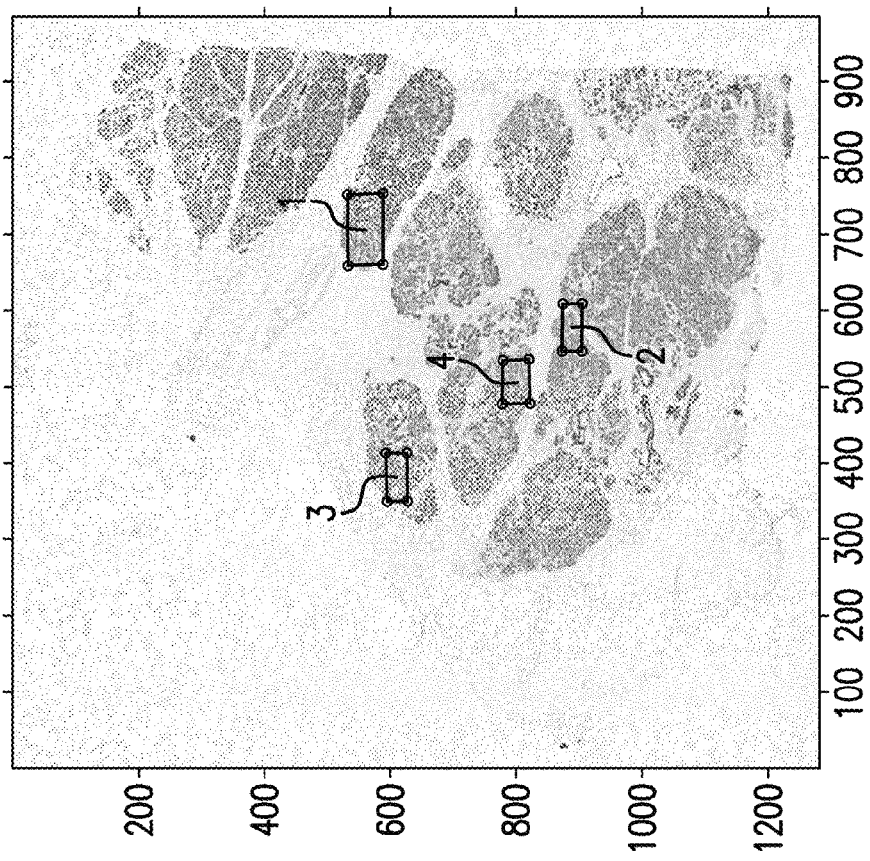
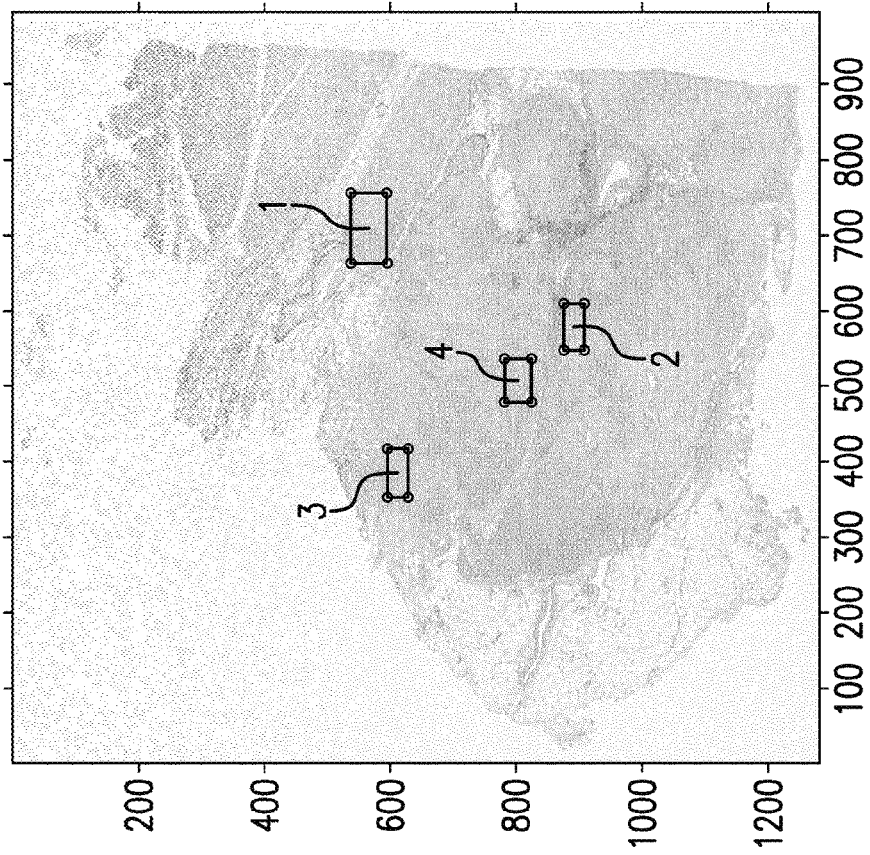
FIG.21C

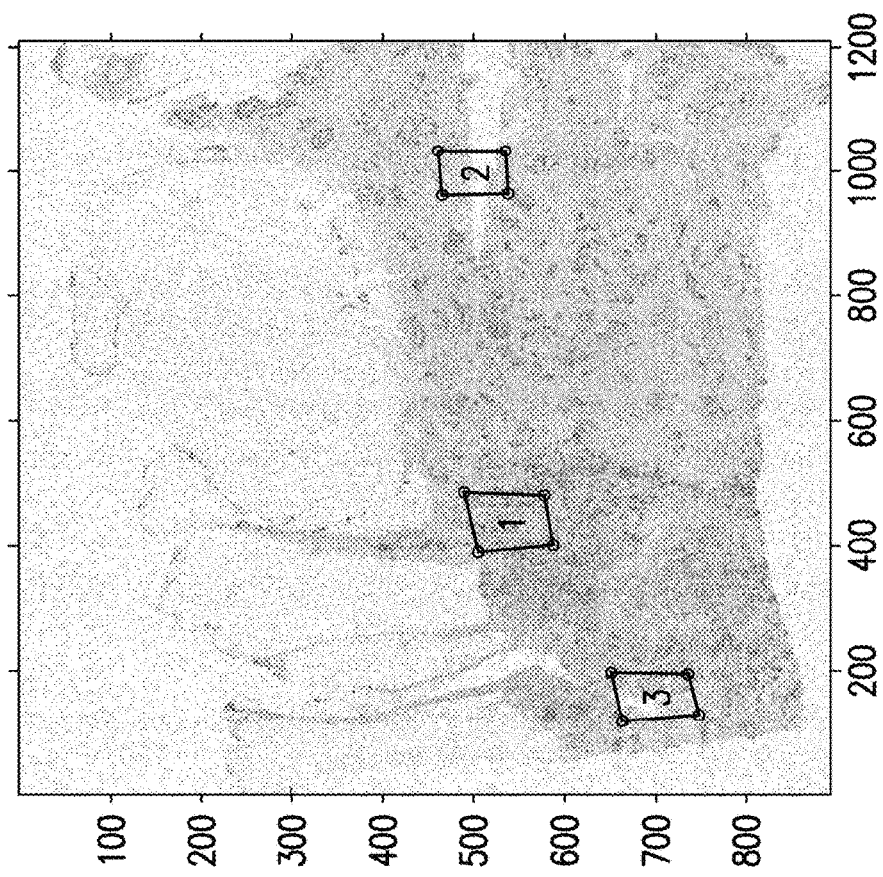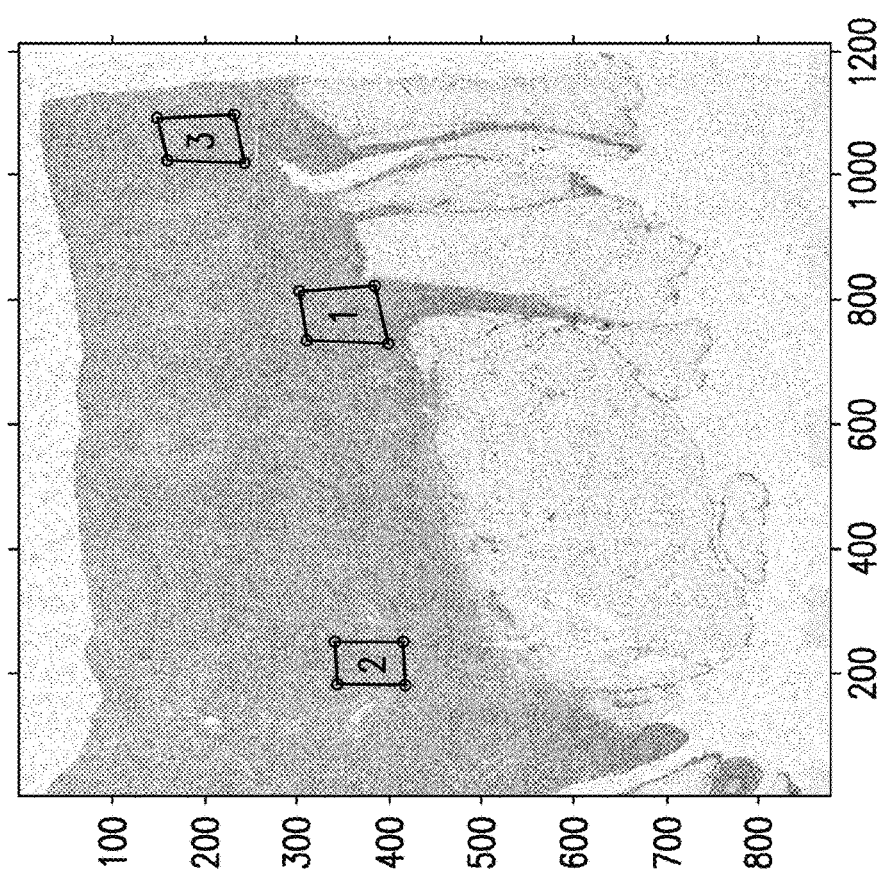
FIG.23

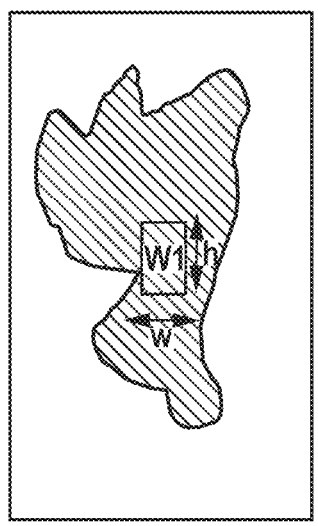 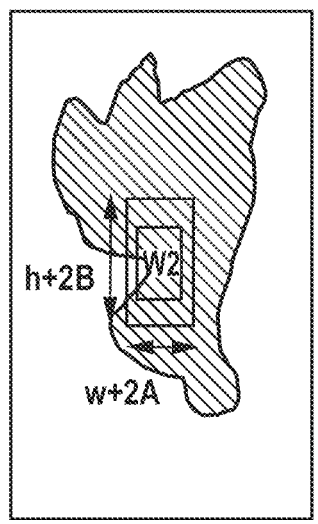
Grid for transformed image 1    Grid for image 2
FIG. 26

Transformed image 1 grid: aligned to grid of image 2

Image 2 grid

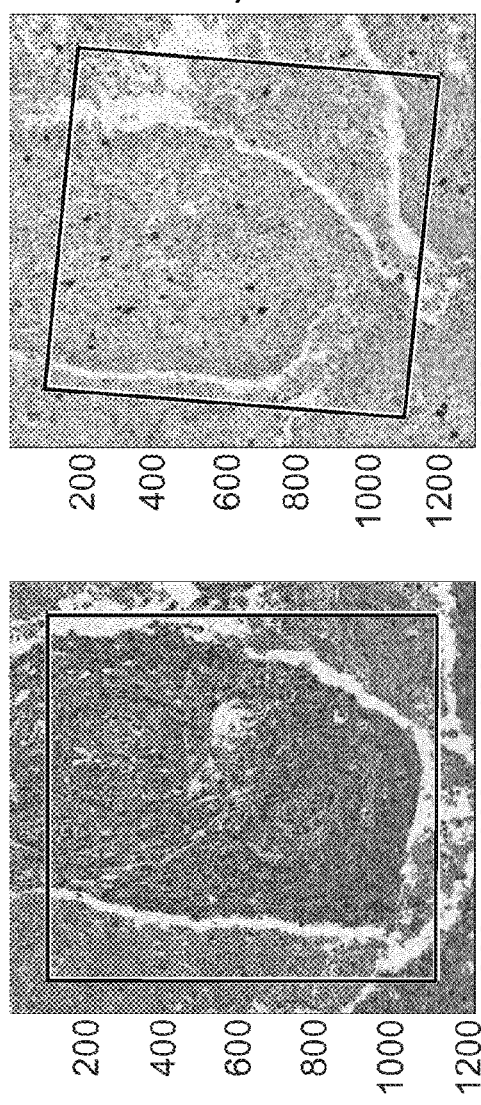
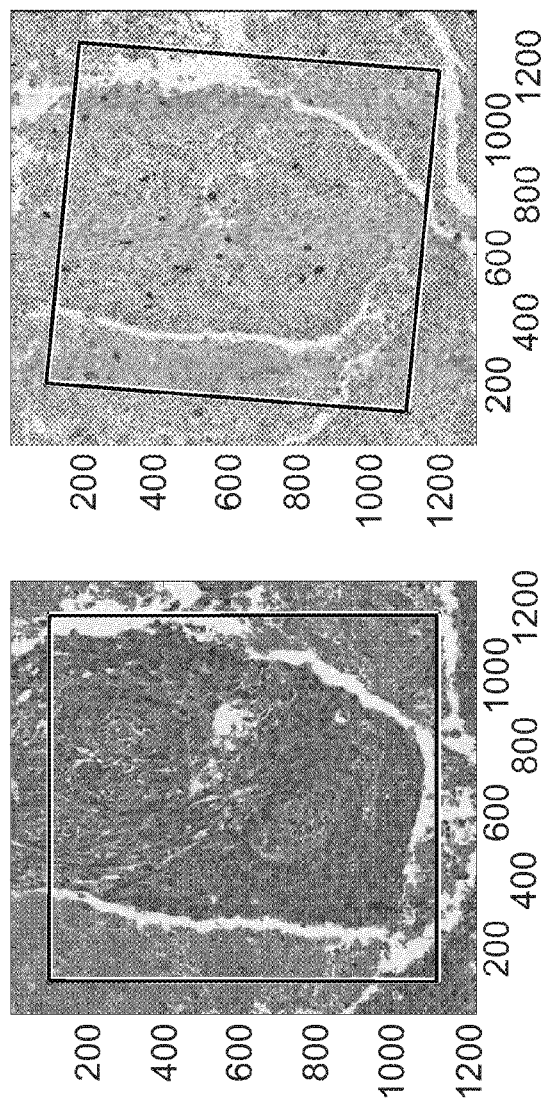
FIG. 31A — Less accurate registration
FIG. 31B — More accurate registration
Results before (top) and after (bottom) finer refinement

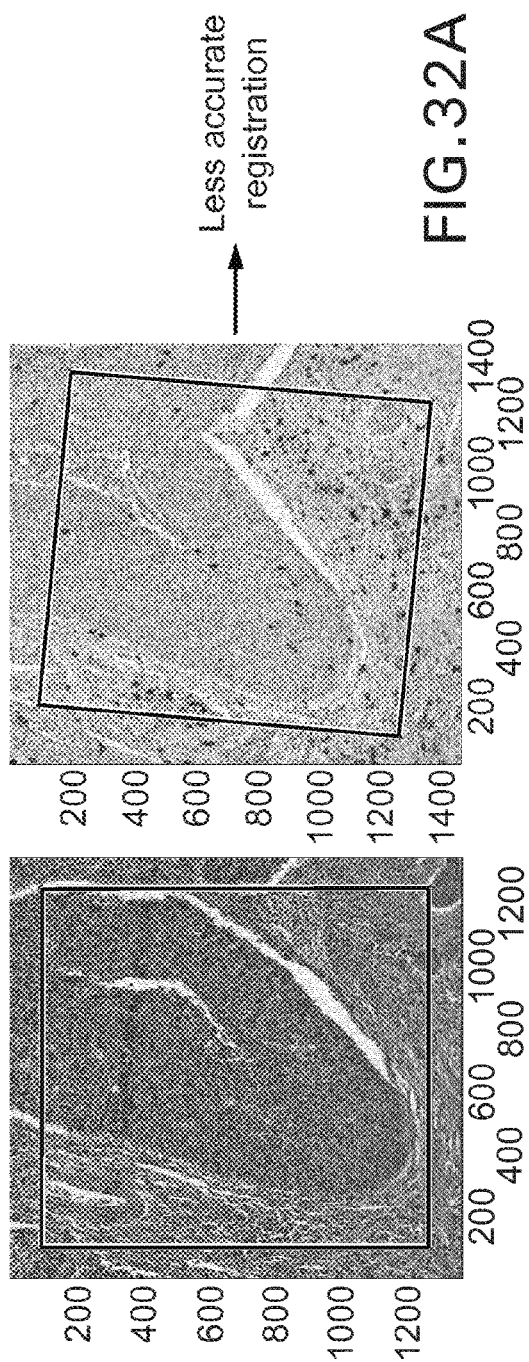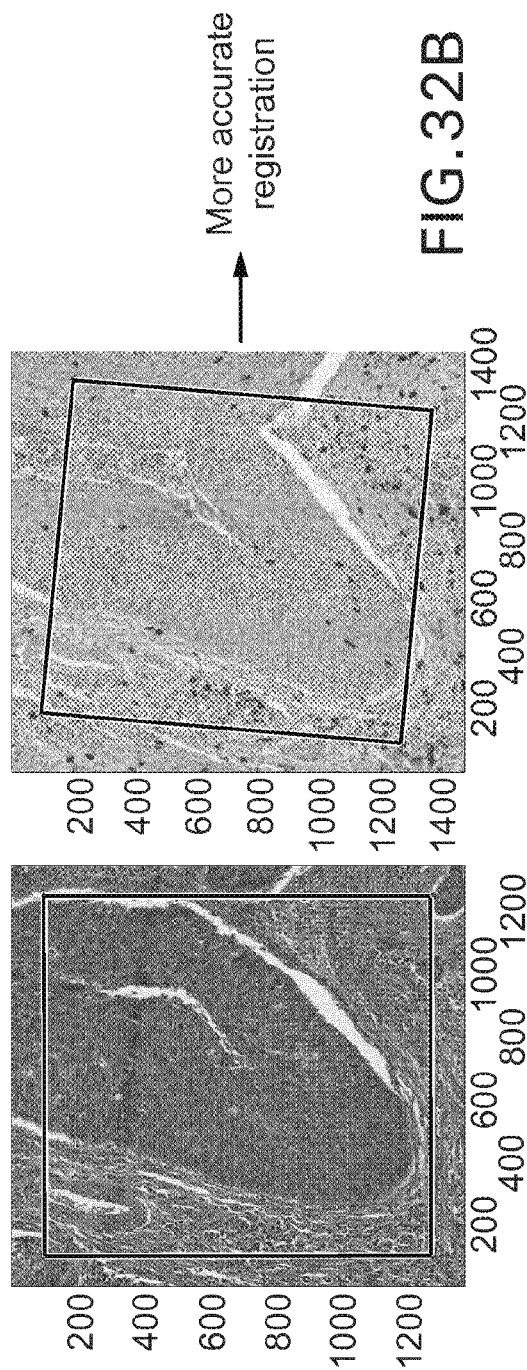
FIG. 32A Less accurate registration
FIG. 32B More accurate registration
Results before (top) and after (bottom) finer refinement

LINE-BASED IMAGE REGISTRATION AND CROSS-IMAGE ANNOTATION DEVICES, SYSTEMS AND METHODS

CROSS-REFERENCE TO RELATED APPLICATIONS

This patent application is a continuation of U.S. patent application Ser. No. 16/706,630, filed Dec. 6, 2019, which is a divisional application of U.S. patent application Ser. No. 15/087,753 filed Mar. 31, 2016, which is a continuation of International patent Application No. PCT/EP2014/070927 filed Sep. 30, 2014, which claims priority to and the benefit of U.S. Provisional Patent Application No. 61/885,024 filed Oct. 1, 2013. Each patent application is incorporated herein by reference as if set forth in its entirety.

FIELD

This specification relates to devices, systems, and methods for manipulation and/or analysis of digitized images of tissue samples. This specification also relates to devices, systems and methods for image registration of a set of digitized images of neighboring tissue section samples. This specification also relates to devices, systems and methods for transferring annotations from one image in the set of images of adjacent tissue section samples to other images in the set of images of adjacent tissue section samples.

BACKGROUND

Digital Pathology refers to the management and interpretation of pathology information in a digital environment. Scanning devices are used to image slides of tissue sections, which may be stained, such that digital slides, e.g., whole slide images are generated. Digital Pathology software enables digital slides to be stored in a computer memory device, viewed on a computer monitor, and analyzed for pathology information. It is expected that Digital Pathology may enable integration of various aspects of the pathology environment such as paper and electronic records, clinical background information, prior cases, images, and results, among other things. It is also expected that Digital Pathology may enable increased efficiencies such as increased workload capability, access to the right pathologist at the right time, rapid retrieval of cases and diagnoses, and improved workflow among other possible efficiencies. However, there are a number of impediments to the widespread adoption of Digital Pathology and the promise of its various benefits, such as imaging performance, scalability and management.

While certain novel features are shown and described below, some or all of which may be pointed out in the claims, the devices, systems and methods of this disclosure are not intended to be limited to the details specified, since a person of ordinary skill in the relevant art will understand that various omissions, modifications, substitutions and changes in the forms and details of the illustrated embodiments and in their operation may be made without departing in any way from the spirit of the disclosure. No feature described herein is critical or essential unless it is expressly stated as being "critical" or "essential."

SUMMARY

The present disclosure provides devices, systems and methods for the manipulation and/or analysis of digitized images of tissue samples. For example, the present disclosure provides devices, systems and methods for computerized image registration of digital slides corresponding to adjacent tissue sections, and/or for transferring annotations from at least one of the digital slides to at least one other of the digital slides.

In general, in some embodiments, the devices, systems and methods are based on modeling the boundary regions of tissue samples reflected in the slides with line segments, then matching sets of line-segments between tissue samples (i.e. between slide images) to obtain an overall global transformation (coarse matching). In some embodiments, the line-based coarse matching approach is able to align images even in cases of mismatch between images (for example wear-and-tear effects, Area of Interest mismatch which can occur when the area of a physical slide picked up by the scanner for high resolution scanning varies from slice-to-slice, rotation (even up to 180 degrees), and horizontal and vertical flips) such as when greater than 50% of lines may be matched between the two images. In further embodiments, the devices, systems, and methods are also based on an additional finer sub-image registration process (which in some embodiments involves normalized, correlation-based, block matching on gradient magnitude images) to compute local refinements between globally-aligned images. In some embodiments, the proposed registration framework provides one or more of the following advantages: i) handles insertions/deletions (in terms of tissue content); ii) is robust to flips; iii) is robust to Area of Interest ("AOI") mismatches (wherein AOI is the area on a physical slide scanned in high resolution); iv) is insensitive to internal content (in some embodiments, for symmetric shapes, when multiple orientations may yield similar matching scores in the line-based matching, edge-map based matching may be used to use internal structure to determine optimal transformation); and, v) for second-pass finer resolution matching, robust criteria are used to decide if high resolution internal structure provides more precise matching.

In some embodiments, the devices include a computer program product for aligning images which are part of a set of digital images of adjacent tissue sections, and/or mapping annotations between aligned images. Each image in the set may be obtained using a different stain (or label, hereinafter "stain"), a different imaging mode, or both, or one or more in the set (or the images which are to be registered) may be scanned using the same stain and imaging mode on the same or different scanners. In some embodiments, the computer program product includes a tangible computer readable storage medium having a computer readable program code embedded therein, the computer readable program code is configured to align selected digital images in the set resulting in a set of aligned digital images using an image registration process (i.e., a process that is directed to, for example, transform different sets of data into one coordinate system) based on matching tissue structure; and the computer readable program code may also be configured to transfer an annotation from at least one digital image in the set of aligned digital images to at least another one of the digital images in the set of aligned images. In other embodiments, the computer program product includes a tangible computer readable storage medium having a computer readable program code embedded therein, the computer readable program code is configured to align a first digital image from the set of digital images of adjacent tissue sections and a second digital image from the set resulting in an aligned image pair using an image registration process based on matching tissue structure; and the computer readable program code may also be configured to transfer an annotation from one of the first or second digital images in the aligned pair to the other of the first or second digital images in the aligned pair. In some embodiments the tissue-matching image registration process is robust to mismatch between images to be aligned. In some embodiments, the tissue-matching image registration process is a line-based image registration process. In some embodiments the tissue-matching image registration process is line-based image registration process which is robust to mismatch between images, for example, when the line-based image registration process produces greater than 50% matching lines between two images for which alignment is desired.

In further embodiments, matching tissue structure involves generating a foreground image mask for each of the selected images in the set of digital images of adjacent tissue sections by OR-combining a binary image mask derived from a soft weighted foreground image and a binary image mask derived from a gradient magnitude image, computing a first set of line-based features from the boundary of the foreground image mask of the first image and computing a second set of line-based features from the boundary of the foreground image mask of the second image, computing global transformation parameters based on matching of the line-based features between the two sets of line-based features, and globally aligning the two images based on the transformation parameters. In further embodiments, globally aligning comprises mapping the transformed first image (the first image is transformed by the computed transformation parameters) from its image grid to the image grid of the second image.

In other embodiments, transferring an annotation includes mapping an annotation from at least one of the aligned images (for example, from the first image or source image) to a corresponding location on at least another of the aligned images (for example, the second image or target image) based on the common grid (which in some embodiments may be the grid of a specific image such as the target image). In further embodiments, transferring the annotation further comprises refining the location of the transferred annotation based on a fine registration process. In further embodiments, the fine registration process includes identifying a window around the original annotation in the source image (for example the first image of an aligned pair of images), identifying a second but larger window in a corresponding location in the target image (for example the second image of an aligned pair of images), and iteratively shifting a third window corresponding to the first window within the second window and identifying an optimal location for the third window in the transformed source image grid which is aligned to the target image. In further embodiments, identifying the optimal location is based on normalized correlation in the gradient magnitude domain.

In some embodiments, the systems include a processor; a memory containing instructions for execution by the processor, which if executed by the processor provide the following results: aligning a first image and second image based on tissue structure, wherein the first image and second image are part of a set of images of adjacent tissue sections and wherein each image in the set may be prepared using a different stain, a different imaging mode, or both; and/or replicating an annotation (for example a pre-existing annotation and/or a user-marked annotation) on one of at least the first image or second image on the other of at least the first image or second image; a client user interface for triggering the processor to execute the instructions; and a monitor for displaying the client user interface, the images, the results, or combinations thereof. In some embodiments, the system is implemented on a computer workstation. In some embodiments, the system is implemented using a computer network.

In some embodiments, the methods include an image registration process involving selecting images from a set of digital images of adjacent tissue sections and aligning the selected images using a registration process based on tissue matching. Each digital image may be obtained using a different stain, a different imaging mode, or both as compared to another digital image in the set. In further embodiments, the image registration process includes selecting a first digital image of a first tissue section from a set of digital images of adjacent tissue sections of a single patient; selecting a second digital image of a second tissue section from the set; and performing a registration process based on matching tissue structure between the first digital image and the second digital image. In some embodiments, the registration process includes a coarse registration mode. In some embodiments, the registration process also includes a fine registration mode.

In some embodiments, the coarse registration mode involves generating a first foreground image mask from the first digital image, generating a second foreground image mask from the second digital image, computing a first set of line-based features from the boundary of the first foreground image mask, computing a second set of line-based features from the second foreground image mask, computing global transformation parameters between the first and second set of line-based features, and mapping the first digital image and the second digital image to a common grid based on the global transformation parameters. In some embodiments, the common grid is that of the second or target image. In some embodiments, computing global transformation parameters comprises matching 50% or more of the lines (or in some embodiments matching greater than 50% of the lines) in the first set to the second set of line-based features and computing the global transformation parameters from the matched sets of lines. In some embodiments, generating a foreground mask (whether a first foreground mask from the first image or a second foreground mask from a second image or both) comprises generating a soft-weighted foreground image from the digital image, applying OTSU thresholding to the soft-weighted foreground image to generating a soft-weighted binary mask, generating a gradient domain image from the digital image, applying OTSU thresholding to the gradient domain image to generate a gradient domain binary mask, and combining the soft-weighted binary mask and the gradient domain binary mask using a logical operation, for example, a binary OR operation (when two binary images A and B are subjected to a binary OR operation to produce a $3^{rd}$ image C, then a certain pixel in image C is 1 when either the corresponding pixel in A is 1, or the corresponding pixel in B is 1, or both the corresponding pixels in A and B are 1) to produce the foreground mask. In some embodiments, the fine registration process includes annotating the first digital image, mapping the annotation on the common grid to a corresponding location on the second digital image, and updating the location of the annotation on the second image using a normalized correlation in the gradient magnitude domain.

In some embodiments, the methods are a method for mapping an annotation from a first digital image from a set of digital images of adjacent tissue sections to a second digital image in the set. In some embodiments, the methods involve selecting a pair of digital images which has been aligned, annotating one of the digital images in the pair if none of the selected images have previously been annotated (or optionally further annotating an image if it has previously been annotated), and transferring the annotation to the other digital image in the pair. In some embodiments the mapping methods involve selecting a first image from a set of digital images of adjacent tissue sections, selecting a second image from the set, instructing a computer processor to execute instructions resulting in aligning the first image with the second image on a common grid using a coarse registration process based on matching tissue structure, for example a line-based, tissue matching image registration process as described further herein, annotating the first image if it has not already been annotated (or optionally further annotating the first image if it already has been annotated), and instructing the computer processor to transfer the annotation or annotation data to the second image. In some embodiments, transferring the annotation occurs automatically, and may occur substantially simultaneously with an initial registration process (for example a coarse registration process) if an image in the pair to be registered has been annotated, or it may occur substantially simultaneously with annotating the first image. In some embodiments, transferring the annotation occurs after the first and second images have been aligned. In some embodiments, transferring the annotation further comprises adjusting the location of the annotation on the second image based on a fine registration process, for example as further described herein. After the line-based registration module, the user has the ability to slightly modify or adjust a retrieved annotation if he perceives that to be a better fit.

While the disclosure provides certain specific embodiments, the invention is not limited to those embodiments. A person of ordinary skill will appreciate from the description herein that modifications can be made to the described embodiments and therefore that the specification is broader in scope than the described embodiments. All examples are therefore non-limiting.

BRIEF DESCRIPTION OF THE DRAWINGS

FIGS. 14B and 14C are a larger scale illustration of some of the basic steps shown in FIG. 14a.

FIGS. 15A to 15D illustrate a color deconvolution process which may be part of the process for generating a soft-weighted foreground image of FIG. 14a.

FIG. 19 illustrates a line-based boundary map generated from a foreground mask.

FIGS. 20A to 20E illustrate a method of generating a line-based boundary map from a foreground mask.

FIGS. 21A to 21C illustrate the applicability of embodiments of coarse registration processes according to this disclosure for slides which have AOI mismatch.

FIG. 23 is another illustration of the applicability of embodiments of coarse registration processes according to this disclosure for slides which have rotation mismatch.

FIG. 26 illustrates the basic concepts of an embodiment of a fine registration process according to this disclosure where the search window is shown around the annotation region returned after coarse registration.

FIG. 29A shows the gradient magnitude image 1 transformed and aligned to the grid of image 2, and FIG. 29B shows the points marked in image 1 recovered (transformed and mapped) in the gradient magnitude domain of image 2 in the grid of image 1

FIGS. 31A and 31B compare a pair of images after the have undergone a coarse registration process in accordance with an embodiment of the disclosure with the same pair of images after they have also undergone a fine registration process according to an embodiment of the disclosure.

FIGS. 32A and 32B provide another comparison of a pair of images after the have undergone a coarse registration process in accordance with an embodiment of the disclosure with the same pair of images after they have also undergone a fine registration process according to an embodiment of the disclosure.

DETAILED DESCRIPTION

Figure 1:
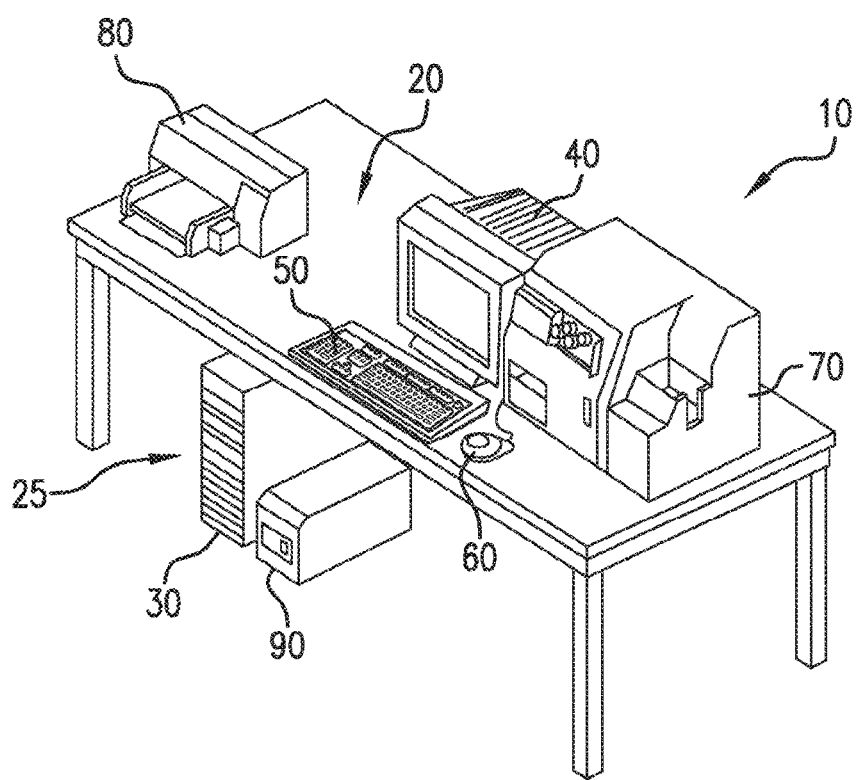
FIG. 1 is a perspective, pictorial representation of an embodiment of a medical imaging workstation system in which the devices, systems and methods according to this disclosure may be implemented.

Detailed descriptions of one or more embodiments are provided herein. It is to be understood, however, that the devices, systems and methods according to this disclosure may be embodied in various forms. Therefore, specific details disclosed herein are not to be interpreted as limiting, but rather as a representative basis for the claims and for teaching one skilled in the art to employ the present devices, systems and methods in any appropriate manner.

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

Where ever the phrase "for example," "such as," "including" and the like are used herein, the phrase "and without limitation" is understood to follow unless explicitly stated otherwise. Similarly "an example," "exemplary" and the like are understood to be non-limiting.

The term "substantially" allows for deviations from the descriptor that don't negatively impact the intended purpose. Descriptive terms are understood to be modified by the term "substantially" even if the word "substantially" is not explicitly recited.

The term "about" is meant to account for variations due to experimental error. All measurements or numbers are implicitly understood to be modified by the word about, even if the measurement or number is not explicitly modified by the word about.

The terms "comprising" and "including" and "having" and "involving" and the like are used interchangeably and have the same meaning. Similarly, "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c.

Where ever the terms "a" or "an" are used, "one or more" is understood unless explicitly stated otherwise or such interpretation is nonsensical in context.

The terms "align" and "register" and all of their forms (for example, "aligning" and "registering") are used in the alternative and mean the same thing when used in connection with the term "image." For example, the phrases "aligned images" and "registered images" are used in the alternative to describe digital images which have undergone an image registration process (for example a coarse registration and/or a fine registration process).

When used in reference to the process of obtaining a soft-weighted foreground image, the terms "spectral unmixing" (or "unmixing") and "color deconvolution" (or "deconvolution") or the like (e.g. "deconvolving," "unmixed") are used interchangeably. For example, where the specification refers to a using color deconvolution alogorithm, a spectral unmixing algorithm could also be used (and vice versa) unless specifically stated otherwise.

As is understood in the art, a digital image file comprises data (image data). Accordingly, references to digital images are also references to image data. For example, reference to a set of digital images implicitly discloses/refers to a set of image data comprising one or more image data files.

This disclosure relates to Digital Pathology and provides computer-implemented devices, systems and methods for digital tissue image analysis. In some embodiments, the devices, systems and methods are implemented on a stand-alone workstation (which may include a modem for access to the internet). In some embodiments, the devices, systems and methods may be implemented over a computer network.

Whether implemented on a stand-alone workstation or over a network, the systems according to this disclosure may include at least some of the following hardware components: a computer comprising an output device for displaying images and/or results such as a monitor and one or more input devices such as a keyboard and mouse or trackball for interacting with software programs, and a processor for executing the software programs. The systems may also include a storage device for storing sets of digital image files, wherein each set includes one or more whole slide images of adjacent tissue sections of the same tissue of a single patient. Each digital image file in a set may be generated from a glass slide using a different imaging mode (for example brightfield microscopy, darkfield, and fluorescent microscopy), or a glass slide in which a tissue section was prepared using a different stain (for example HE, IHC, and/or ISH stains), or both, as compared to another digital image file in the set. The storage device can be part of the computer itself or it can be a separate device such as a network-accessible storage device. The systems may also include a scanner for producing the digital image files from glass slides. In certain embodiments within the scope of this disclosure, a biological specimen (which may or may not be a tissue specimen) is placed on a substrate, which may or may not be a glass or microscope slide. In certain embodiments within the scope of this disclosure, the biological specimens (e.g., tissue specimens), which are imaged and compared, may not originate from the same section or block of a patient. In certain embodiments within the scope of this disclosure, the digital images that are registered and available for use in accordance with methods within the scope of this disclosure may be images of non-adjacent tissue sections from a single patient. In certain embodiments within the scope of this disclosure, the digital images that are registered and available for use in accordance with methods within the scope of this disclosure may be images of biological specimens from different patients.

Whether implemented on a stand-alone workstation or over a network, the systems may also include the following software components: an image analysis program comprising a registration module (which may include a coarse registration module and/or a fine registration module), an annotation module or both. The registration module, when executed by the processor, results in aligning at least two digital images in a set of digital images of adjacent tissue sections thereby creating a set of aligned digital images. The annotation module, when executed by the processor, results in mapping an annotation on at least one of the digital images in the set of digital images of adjacent tissue sections to at least another one of the digital images in the set. In some embodiments, the annotation module, when executed by the processor, results in annotating at least one of the digital images and/or mapping an annotation on at least one of the digital images to at least another of the digital images. In some embodiments, the registration module is executed substantially simultaneously with the annotation module. For example, a request to map an annotation from one slide to another slide causes the processor to both align and map an annotation from at least one of the images to at least another of the images. In some embodiments, the annotation can be pre-existing on the source image. In some embodiments, the annotation is user-generated in the image analysis program, by for example, selecting an image as the source image and annotating that image using the image analysis program. In some embodiments, the registration module is executed prior to the annotation module. For example, the annotation module, when executed by the processor results in mapping an annotation from at least one digital image that is part of a set of aligned images to at least one other digital image that is part of the set of aligned images. The systems also include an image viewing module, which may be part of the image analysis program and enables a user to access one or more digital image files, view the files on the monitor(s), and in some embodiments, manipulate the digital slides using a client user interface.

Computer-implemented methods according to this disclosure comprise: a computer-implemented registration process for aligning at least two digital images from the same tissue block, section, or sample of a single patient based on tissue structure resulting in a set of aligned digital images, wherein each digital image in the set may be derived from an image obtained using a different stain, a different imaging mode, or both as compared to the other digital images in the set; and, a computer-implemented mapping process for mapping an annotation on at least one of the digital images in the set of aligned digital images to at least another of the digital images in the set of aligned digital images. In some embodiments, the image registration process and the annotation process occur substantially coextensively. For example, an instruction to map an annotation from one digital slide to another results in both aligning the slides and annotating the slides, for example the annotation instruction results in first aligning the images and then transferring the annotation from one image to the other image. In some embodiments, the image registration process occurs first, and the annotation process is initiated by first selecting at least a pair of aligned images and next annotating at least one of the images in the at least one pair of aligned images. In some embodiments, the registration process comprises a coarse registration process. In some embodiments, the registration process comprises a coarse registration process and a fine registration process. In further embodiments, the annotation of the source image is done before the fine registration module is used and/or before the coarse registration process is used. Thus, for example, in some embodiments, wherein a user desires simultaneous viewing of both a source and a target image, the coarse registration process may be invoked to perform global registration of both images, without needing any specific annotations. In some embodiments, wherein a user desires to return user-marked annotations of a source image to a target image, a fine registration process may be invoked, for example in regions close to the user annotations, to improve alignment of the source and target images as compared to just relying on a coarse registration.

In some embodiments, the coarse registration process may involve selecting digital images for alignment, generating a foreground image mask from each of the selected digital images, and matching tissue structure between the resultant foreground images. In further embodiments, generating a foreground image mask involves generating a soft-weighted foreground image from the whole slide image of a stained tissue section and applying OTSU thresholding to the soft-weighted foreground image to produce a binary soft-weighted image mask. In other further embodiments, generating a foreground image mask involves generating a binary soft-weighted image mask from a whole slide image of a stained tissue section, separately generating a gradient magnitude image mask from the same whole slide image, applying OTSU thresholding to the gradient image mask to produce a binary gradient magnitude image mask, and combining the binary soft-weighted image and the binary gradient magnitude image mask using a binary OR operation to generate the foreground image mask. In some embodiments, matching tissue structure involves computing line-based features from the boundary of each of the resultant foreground image masks, computing global transformation parameters between a first set of line-features on a first foreground image mask and a second set of line-features on a second foreground image mask, and globally aligning the first and second image based on the transformation parameters. In yet further embodiments, the coarse registration process includes mapping the selected digital images based on the global transformation parameters to a common grid, which grid may encompass the selected digital images. In some embodiments, the fine registration process may involve identifying a first sub-region of a first digital image in the set of aligned digital images, for example a sub-region comprising an annotation (or for example corresponding to an annotation); identifying a second sub-region on a second digital image in the set of aligned digital images, wherein the second sub-region is larger than the first sub-region and the first sub-region is located substantially within the second sub-region on common grid; and, computing an optimized location for the first sub-region in the second sub-region.

In some embodiments, the mapping process may involve annotating a first digital image in a set of aligned images after the coarse registration process, and mapping the annotation to a second digital image in the set of aligned digital images. In further embodiments, the location of the annotation is refined based on results of the fine registration process.

Although examples described herein are typically directed at comparing a pair of adjacent tissue samples (or parallel slices), the workflow may be extended beyond a registration framework of only two images to include frameworks in which multiple layers are provided as input, including even images from multiple scanners. In some embodiments, this can be done by considering the multiple layers in sets of two layers which are in closest proximity. As an example, if three parallel slices are provided as input, the first layer (e.g. H&E) may be first registered with the second layer (e.g. IHC-1), and the second layer may then be registered with the third layer (e.g. IHC-2).

Referring now to the Figures, wherein like reference numerals refer to like parts throughout, FIG. 1 is a perspective, pictorial representation of an embodiment of a medical imaging workstation system 10 in which the devices, systems and methods according to this disclosure may be implemented. As shown, the medical imaging workstation system 10 includes a computer 20 having a housing for hardware components 30 such as a processor ("CPU") (not shown), a storage device (not shown), a graphics processor unit ("GPU") (not shown), and optionally a modem (not shown); a first output device, which in the illustrated example is a monitor 40; a first user input device, which in the illustrated example is a keyboard 50; and, a second user input device, which in the illustrated example is a pointing device for interacting with the display such as a track ball or mouse 60. As is known in the art, although the computer 20, hardware component 30, monitor 40, and user input devices 50, 60 are illustrated as separate components, they may be integrated in fewer parts such as they may all be integrated in the form of a laptop computer. The medical imaging workstation system 10 may also include additional peripherals such as a third input device, which in the illustrated example is a slide scanner 70, a second output device, which in the illustrated example is a printer 80, a back-up power supply 90, and external storage devices (not shown), among other devices which are known to be associated with computer-implemented medical imaging systems. In some embodiments, the medical imaging workstation system 10 may include more than one monitor 40 for ease of simultaneous viewing of multiple digital tissue images on multiple screens. As a person of skill appreciates, the specific components may change as technology changes. For example, a peripheral pointing device may not be necessary if the screen is responsive to a user's finger, or voice commands.

The medical imaging workstation system 10 also includes software components such as an image analysis program comprising a registration module, an annotation module or both, as well as an image viewing module which may be part of the image analysis program. The software components may be one or more files, which are stored on the storage device (for example the software components may be stored on an internal hard drive) and/or the software components may be stored on a memory disc such as a DVD, CD or memory card, which can be accessed by the processor when the memory disc is inserted into the housing 30 through a memory-disc receiving port 25.

The CPU is operatively connected to the various peripherals and hardware components, including the storage device and the GPU. The storage device may temporarily or permanently store sets of digital images, which may be imported into the system, for example by a scanning device. The sets of digital images include one or more digital images of adjacent tissue sections of a single patient, wherein each image can be obtained using a different stain/label/marker, a different imaging mode, or both as compared to another image. The GPU processes instructions from an image display program and image analysis program (which may be combined in a single program). When executed, for example by the GPU, the image display program may provide a windowed graphical user interface ("GUI") on the monitor 40 with multiple windows such that a user may interact with the GUI to provide instructions resulting in a processor, such as for example the CPU, executing one or more aspects of the image analysis program, and/or may result in displaying one or more of the stored digital images on one or more of the monitors 40, either in their native (originally-scanned) format or as modified by the image analysis program. As previously mentioned, the image analysis program comprises a registration module and an annotation module. When executed, for example by the CPU, the registration module results in aligning a least two of the stored digital images, even stored digital images that are obtained using different stains, different imaging modes, or both, on a common grid based on tissue structure, creating a set of aligned images. When executed, for example by the CPU, the annotation module results in mapping an annotation from one of the digital images in the set of aligned images to at least another of the digital images in the set of aligned images.

Figure 2:
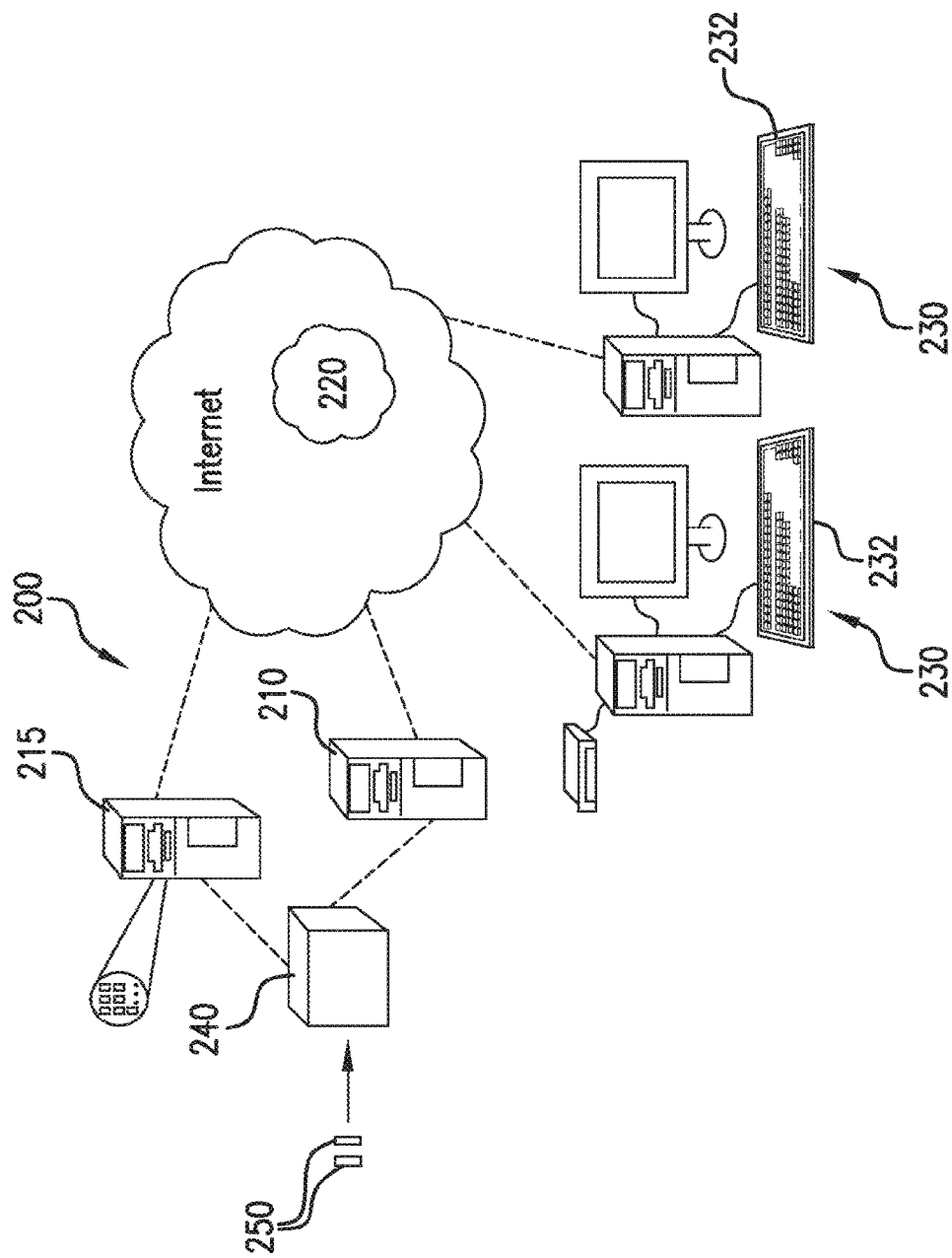
FIG. 2 is a network diagram illustrating an embodiment of a networked system in which the devices, systems and methods according to this disclosure may be implemented.

FIG. 2 is a network diagram illustrating an embodiment of a networked system in which the devices, systems and methods according to this disclosure may be implemented. As shown, the system 200 includes a database server 210 and a network-accessible storage device 215, each of which is connected to a network 220. The storage device 215 stores sets of digital images, wherein each set includes one or more digital images of adjacent tissue sections of a single patient. Each image in a set may be obtained by using a different stain, a different imaging mode or both as compared to another image in a set. One or more client computers 230, which may have associated input and output devices such as a keyboard 232, mouse (not shown) and printer (not shown) are also connected to the network 220 by any means known in the art (for example a dedicated connection, a DSL or cable modem, a wireless internet connection, a dial-up modem or the like). The client computer 230 includes a web browser which is used to access the digital images in the stored device 215. In exemplary embodiments of the present invention, cloud storage may be utilized for storing the digital images.

The client computer 230 includes at least one processor configured to execute instructions relating to an image analysis program. The image analysis program may be downloaded to the client computer 230 from the server 210. The image analysis program may include an image viewer module, which provides a client user interface such that when executed, the image viewer module may provide a windowed GUI with multiple windows that enables a user to provide instructions resulting in the processor executing one or more aspects of the image analysis program and/or may result in displaying one or more of the stored digital images, either in their originally-scanned format or as modified by the image analysis program. The image analysis program enables a user to select images for alignment (registration) in a set of images obtained from a tissue section of a single patient, but wherein each image in the set may have been made using a different stain, or a different mode or both as compared to other images in the set. The image analysis program also enables a user to annotate one or more selected digital images in the set of digital images and have those annotations mapped to one or more of the other digital images in the set of digital images. In some embodiments, the system 200 also includes a scanner 240 for scanning whole slides 250 and producing the digital images which are stored in the storage device 215.

As a person of skill understands, implementing the image analysis program in the context of a computerized network enables certain activities that may otherwise be limited by stand-alone work stations. For example, pathologists who are not co-located, and indeed may be remote from one another, may collaborate in analyzing images, or the right pathologist may be reached at the right time, independent of location.

FIGS. 1 and 2 illustrate certain elements which may be present in one or more computer system or network topologies. A person of skill understands that computer systems and networks in which devices and systems according to this disclosure may be implemented may encompass other computer system and network topologies, and may include more or less elements in those other computer system and network topologies. In other words, the embodiments of FIGS. 1 and 2 are not limiting. For example, in some embodiments, cloud storage may be used for storing the digital images.

Accordingly, an exemplary embodiment of a computer system for use in accordance with the present disclosure may include any number of computer platforms or multiple types of computer platforms, such as workstations, personal computers, servers, hand-held devices, multi-processor systems, microprocessor-based or programmable consumer electronics, network PCs, minicomputers, mainframe computers or any other present or future computer.

An exemplary embodiment may also be practiced in distributed computing environments where tasks are performed by local and/or remote processing devices that are connected (by, for example, hardwired connections, wireless connections, or a combination thereof), in a communications network. In a distributed computing environment, program modules may be located in both local and remote computer storage media including memory storage devices. It will, however, be appreciated by one of ordinary skill in the art that the aforementioned computer platforms as described herein are specifically configured to perform the specialized operations of the described invention and are not considered general purpose computers.

Computers typically include known components, such as a processor, an operating system, system memory, memory storage devices, input-output controllers, input-output devices, and display devices. It will also be understood by those of ordinary skill in the relevant art that there are many possible configurations and components of a computer and may also include cache memory, a data backup unit, and many other devices.

Examples of input devices include a keyboard, a cursor control devices (e.g., a mouse), a microphone, a scanner, and so forth.

Examples of output devices include a display device (e.g., a monitor or projector), speakers, a printer, a network card, and so forth. Display devices may include display devices that provide visual information, this information typically may be logically and/or physically organized as an array of pixels.

An interface controller may also be included that may comprise any of a variety of known or future software programs for providing input and output interfaces. For example, interfaces may include what are generally referred to as "Graphical User Interfaces" (often referred to as GUI's) that provide one or more graphical representations to a user. Interfaces are typically enabled to accept user inputs using means of selection or input known to those of ordinary skill in the related art. The interface may also be a touch screen device.

In the same or alternative embodiments, applications on a computer may employ an interface that includes what are referred to as "command line interfaces" (often referred to as CLI's). CLI's typically provide a text based interaction between an application and a user. Typically, command line interfaces present output and receive input as lines of text through display devices. For example, some implementations may include what are referred to as a "shell" such as Unix Shells known to those of ordinary skill in the related art, or Microsoft Windows Powershell that employs object-oriented type programming architectures such as the Microsoft .NET framework. Those of ordinary skill in the related art will appreciate that interfaces may include one or more GUI's, CLI's or a combination thereof.

A processor may include a commercially available processor such as a Celeron, Core, or Pentium processor made by Intel Corporation, a SPARC processor made by Sun Microsystems, an Athlon, Sempron, Phenom, or Opteron processor made by AMD Corporation, or it may be one of other processors that are or will become available. Some embodiments of a processor may include what is referred to as multi-core processor and/or be enabled to employ parallel processing technology in a single or multi-core configuration. For example, a multi-core architecture typically comprises two or more processor "execution cores". In the present example, each execution core may perform as an independent processor that enables parallel execution of multiple threads. In addition, those of ordinary skill in the related will appreciate that a processor may be configured in what is generally referred to as 32 or 64 bit architectures, or other architectural configurations now known or that may be developed in the future.

A processor typically executes an operating system, which may be, for example, a Windows-type operating system from the Microsoft Corporation; the Mac OS X operating system from Apple Computer Corp.; a Unix or Linux-type operating system available from many vendors or what is referred to as an open source; another or a future operating system; or some combination thereof. An operating system interfaces with firmware and hardware in a well-known manner, and facilitates the processor in coordinating and executing the functions of various computer programs that may be written in a variety of programming languages. An operating system, typically in cooperation with a processor, coordinates and executes functions of the other components of a computer. An operating system also provides scheduling, input-output control, file and data management, memory management, and communication control and related services, all in accordance with known techniques.

System memory may include any of a variety of known or future memory storage devices that can be used to store the desired information and that can be accessed by a computer. Computer-readable storage media may include volatile and non-volatile, removable and non-removable media implemented in any method or technology for storage of information such as computer readable instructions, data structures, program modules, or other data. Examples include any commonly available random access memory (RAM), read-only memory (ROM), electronically erasable programmable read-only memory (EEPROM), digital versatile disks (DVD), magnetic medium, such as a resident hard disk or tape, an optical medium such as a read and write compact disc, or other memory storage device. Memory storage devices may include any of a variety of known or future devices, including a compact disk drive, a tape drive, a removable hard disk drive, USB or flash drive, or a diskette drive. Such types of memory storage devices typically read from, and/or write to, a program storage medium such as, respectively, a compact disk, magnetic tape, removable hard disk, USB or flash drive, or floppy diskette. Any of these program storage media, or others now in use or that may later be developed, may be considered a computer program product.

As will be appreciated, these program storage media typically store a computer software program and/or data. Computer software programs, also called computer control logic, typically are stored in system memory and/or the program storage device used in conjunction with memory storage device. In some embodiments, a computer program product is described comprising a computer usable medium having control logic (computer software program, including program code) stored therein. The control logic, when executed by a processor, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Input-output controllers could include any of a variety of known devices for accepting and processing information from a user, whether a human or a machine, whether local or remote. Such devices include, for example, modem cards, wireless cards, network interface cards, sound cards, or other types of controllers for any of a variety of known input devices. Output controllers could include controllers for any of a variety of known display devices for presenting information to a user, whether a human or a machine, whether local or remote.

In the presently described embodiment, the functional elements of a computer communicate with each other via a system bus. Some embodiments of a computer may communicate with some functional elements using network or other types of remote communications. As will be evident to those skilled in the relevant art, an instrument control and/or a data processing application, if implemented in software, may be loaded into and executed from system memory and/or a memory storage device. All or portions of the instrument control and/or data processing applications may also reside in a read-only memory or similar device of the memory storage device, such devices not requiring that the instrument control and/or data processing applications first be loaded through input-output controllers. It will be understood by those skilled in the relevant art that the instrument control and/or data processing applications, or portions of it, may be loaded by a processor, in a known manner into system memory, or cache memory, or both, as advantageous for execution.

Also, a computer may include one or more library files, experiment data files, and an internet client stored in system memory. For example, experiment data could include data related to one or more experiments or assays, such as detected signal values, or other values associated with one or more sequencing by synthesis (SBS) experiments or processes.

Additionally, an internet client may include an application enabled to access a remote service on another computer using a network and may for instance comprise what are generally referred to as "Web Browsers". In the present example, some commonly employed web browsers include Microsoft Internet Explorer available from Microsoft Corporation, Mozilla Firefox from the Mozilla Corporation, Safari from Apple Computer Corp., Google Chrome from the Google Corporation, or other type of web browser currently known in the art or to be developed in the future. Also, in the same or other embodiments an internet client may include, or could be an element of, specialized software applications enabled to access remote information via a network such as a data processing application for biological applications.

A network may include one or more of the many various types of networks well known to those of ordinary skill in the art. For example, a network may include a local or wide area network that may employ what is commonly referred to as a TCP/IP protocol suite to communicate. A network may include a network comprising a worldwide system of interconnected computer networks that is commonly referred to as the internet, or could also include various intranet architectures. Those of ordinary skill in the related arts will also appreciate that some users in networked environments may prefer to employ what are generally referred to as "firewalls" (also sometimes referred to as Packet Filters, or Border Protection Devices) to control information traffic to and from hardware and/or software systems.

Figure 3:
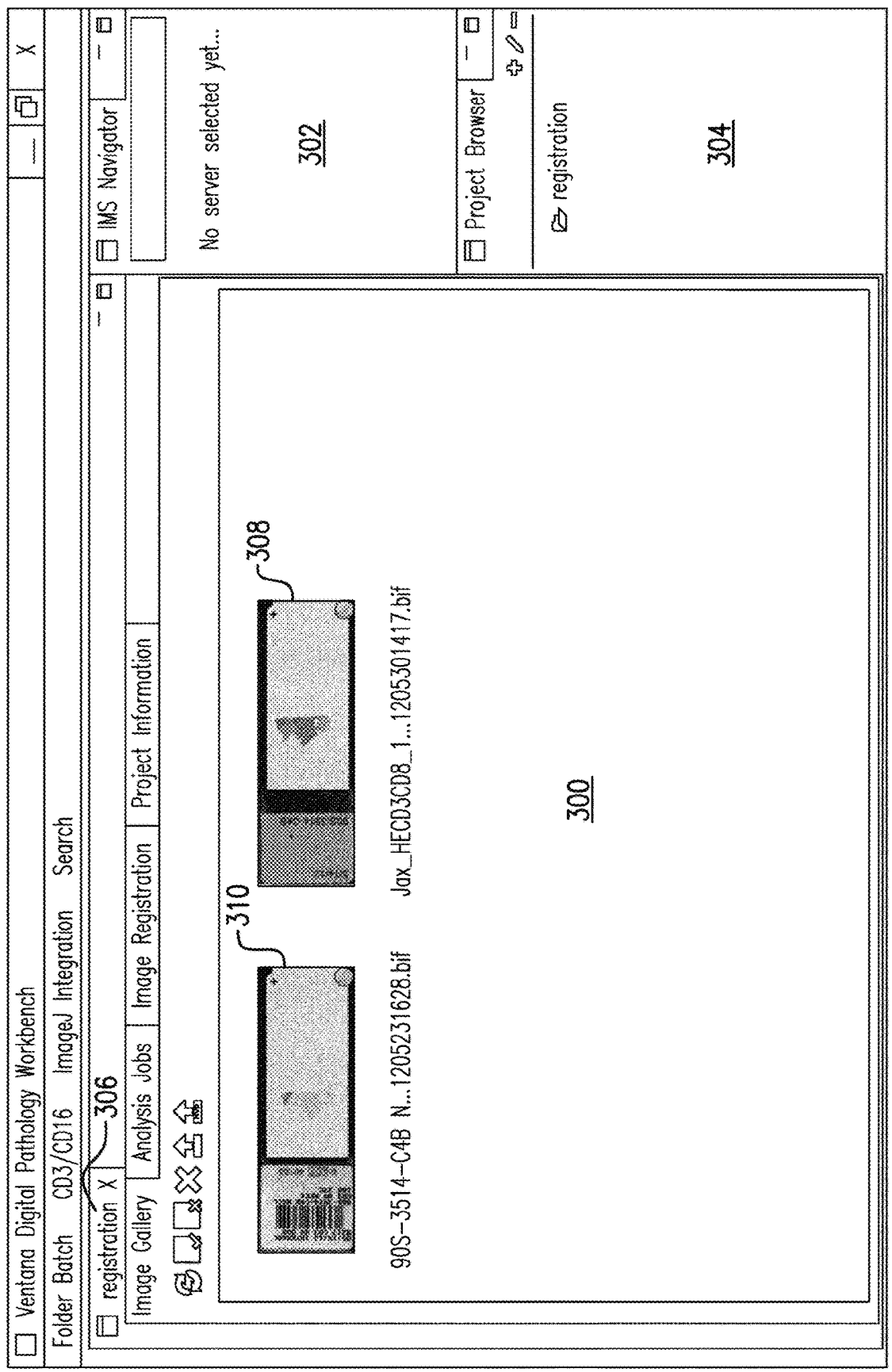
FIG. 3 is a screenshot of a home screen comprised of interactive menu bars and windows, which home screen may be part of a windowed graphical client user interface associated with an embodiment of an image analysis program in accordance with this disclosure.
Figure 4:
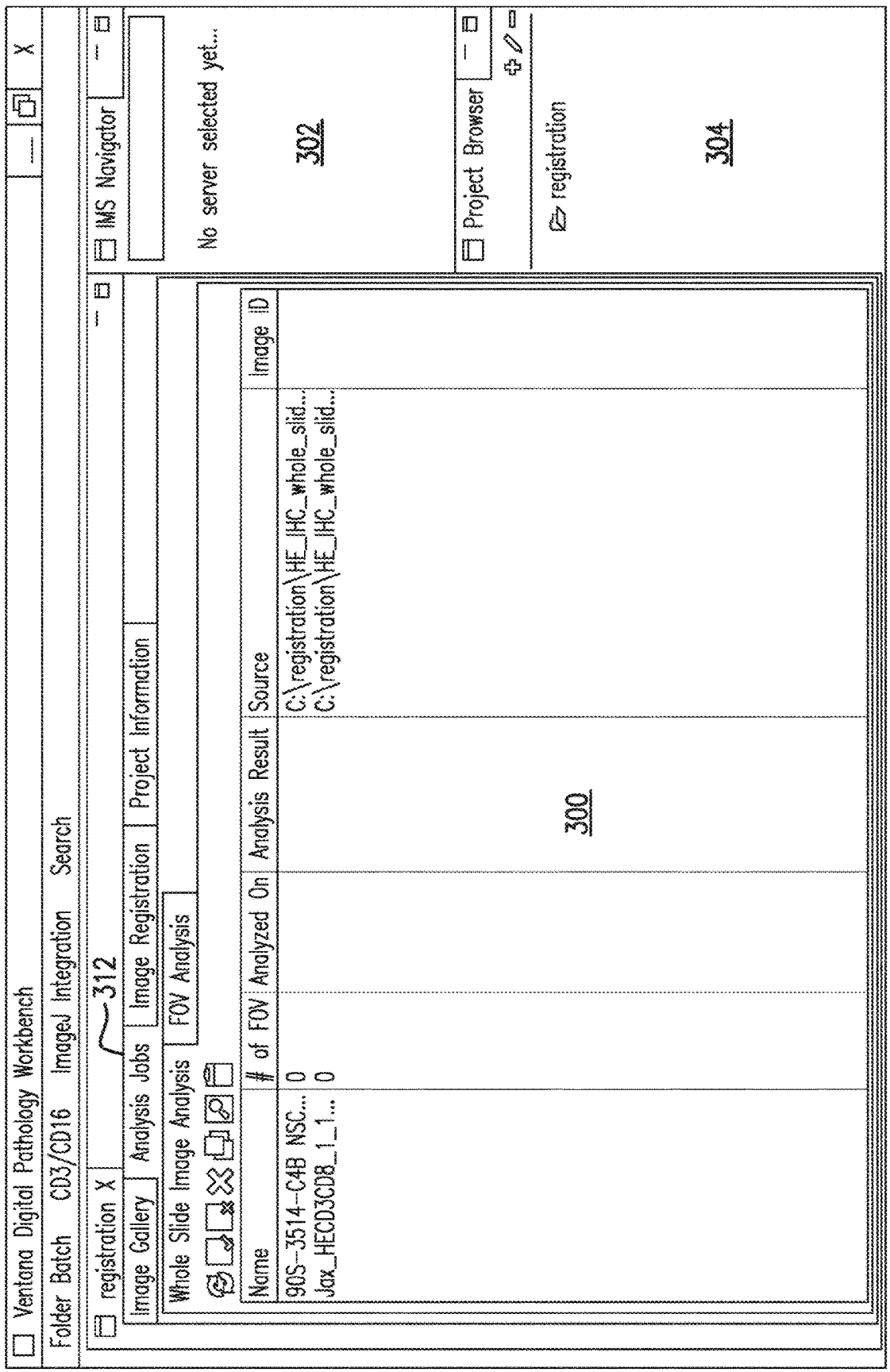
FIG. 4 is another screenshot of the home screen of FIG. 3 with a different menu option selected.
Figure 5:
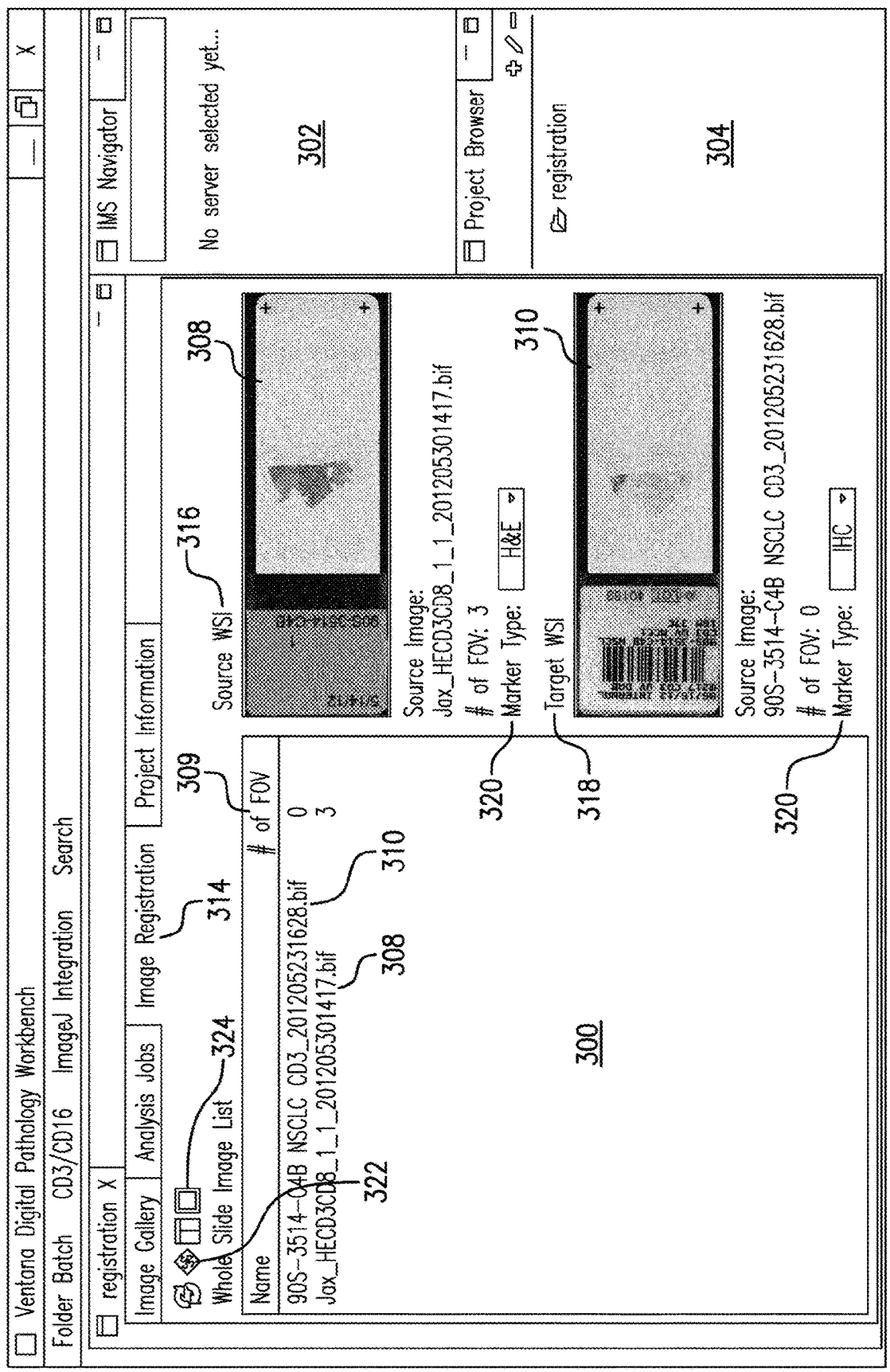
FIG. 5 is another screenshot of the home screen of FIG. 3 with yet another menu option highlighted.

FIGS. 3 to 5 together illustrate an embodiment of the client user interface for interacting with the processor to manage, align and/or annotate images. In the illustrated embodiment, the client user interface is implemented over two basic tools: "WorkBench" is a slide project management tool, whereas "VersoViewer" (or "Verso") is a slide viewer and annotation tool. Verso can also be used as an analysis platform because image analysis algorithms can be invoked from Verso. WorkBench and Verso are presented as an example of interface and workflow tools, based on which the registration framework is presented. However, the registration workflow is generic enough such that it can be used with and/or adapted for use with other annotation/viewer GUI tools and other image analysis/management tools.

FIGS. 3 and 4 illustrate an embodiment of a home screen for the WorkBench GUI interface, which opens when the image analysis program is launched, for example to create an analysis project for a registration problem. In the illustrated embodiment, the home screen is comprised of multiple different windows (as shown, a "registration" window 300, a "navigator" window 302, and a "project browser" window 304). Within this windowed environment, a user may select from various options in which to ultimately invoke and implement image registration, image annotation, and image and results display. The project browser window 304 helps the user to locate an already created project, for example if the user is not starting a new project, whereas the navigator window 302 helps the user to access images which, for example, may be located on a remote server. The registration window 300 includes various buttons, whose functionality is described in more detail below.

After launching the program, once a project is created, a user may select the "Image Gallery" section 306 of the Image Registration module (e.g. registration window 300), as shown in FIG. 3, to preview images being considered for registration. In the illustrated example, the Image Gallery 306 contains two images, a HE image 308 and an IHC image 310, which are displayed as a thumb nail picture of the whole slide image with the name of the whole slide image appearing below the thumb nail. However, the Image Gallery 306 can contain any number of images (e.g., limited by the storage capacity of the system), including entire sets of images taken from adjacent tissue sections. Images are added to the Image Gallery 306 according to means known in the art, for example, upon clicking the Image Gallery tab 306, images can be added by dragging and dropping them from an area of the user interface or a database into the Image Gallery 306.

As shown in FIG. 4, selecting the "Analysis Jobs" folder 312 of the registration window 300 brings up a list of images available in the Image Gallery 306 and associated information, for example the different annotations already available for images in the Image Gallery 306. In the present example, no annotations are available for any of the images in the Image Gallery 306.

As shown in FIG. 5, under the Image Registration tab 314, a user may identify an image in the project as the source image (has user annotations or will be annotated with user annotations) and a user may also identify an image in the project as a target image (the registration module will retrieve annotations for this image). In the illustrated example, the HE image 308 has been dragged and dropped into the "Source WSI" (whole slide image) panel 316 identifying the HE image 308 as the source image, and the IHC image 310 has been dragged and dropped into the "Target WSI" panel 318, identifying the IHC image as the target image. Within each WSI panel 318, the stain type for each image is input by selecting the appropriate tag option in "Marker Type" 320.

Figure 9:
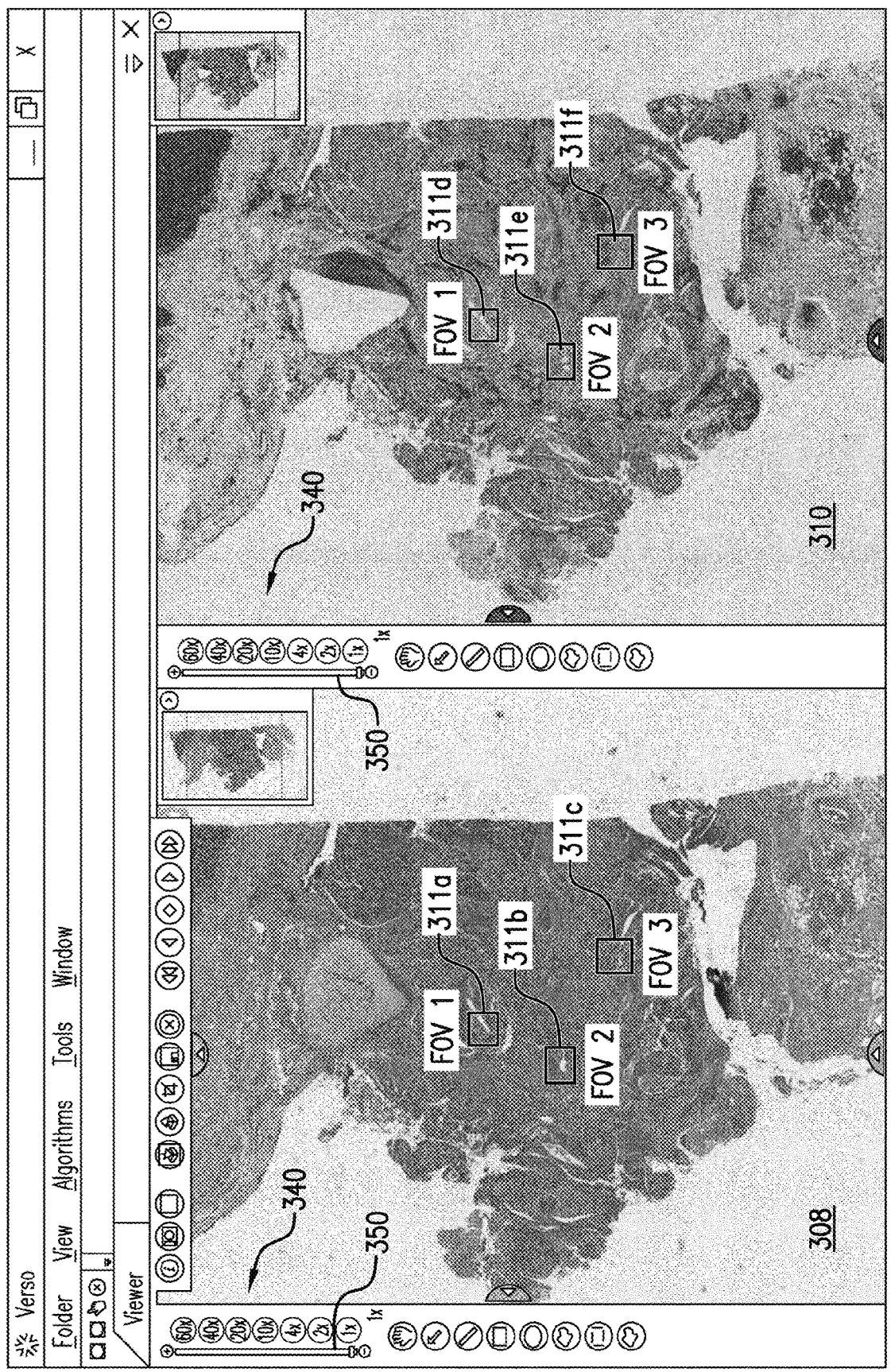
FIG. 9 is a screenshot of the annotation module GUI, which screen in the illustrated embodiment opens automatically after registration has been performed.

If the source image already contains user annotations, the registration routine may be invoked by clicking on the "Analysis" button 322 under the Image Registration tab 314. The side-by-side FOV viewing button 324, also under the Image Registration tab 314, provides side-by-side viewing of matched Field of Views ("FOV"s) from source and target images, enabling a user to compare the user-marked FOV with the algorithm-retrieved FOV, in the target image. In the exemplified embodiment, once the analysis button 322 is clicked and registration is complete, Verso Viewer automatically launches and displays the source 308 and target 310 images side-by-side, as shown in FIG. 9.

Figure 6:
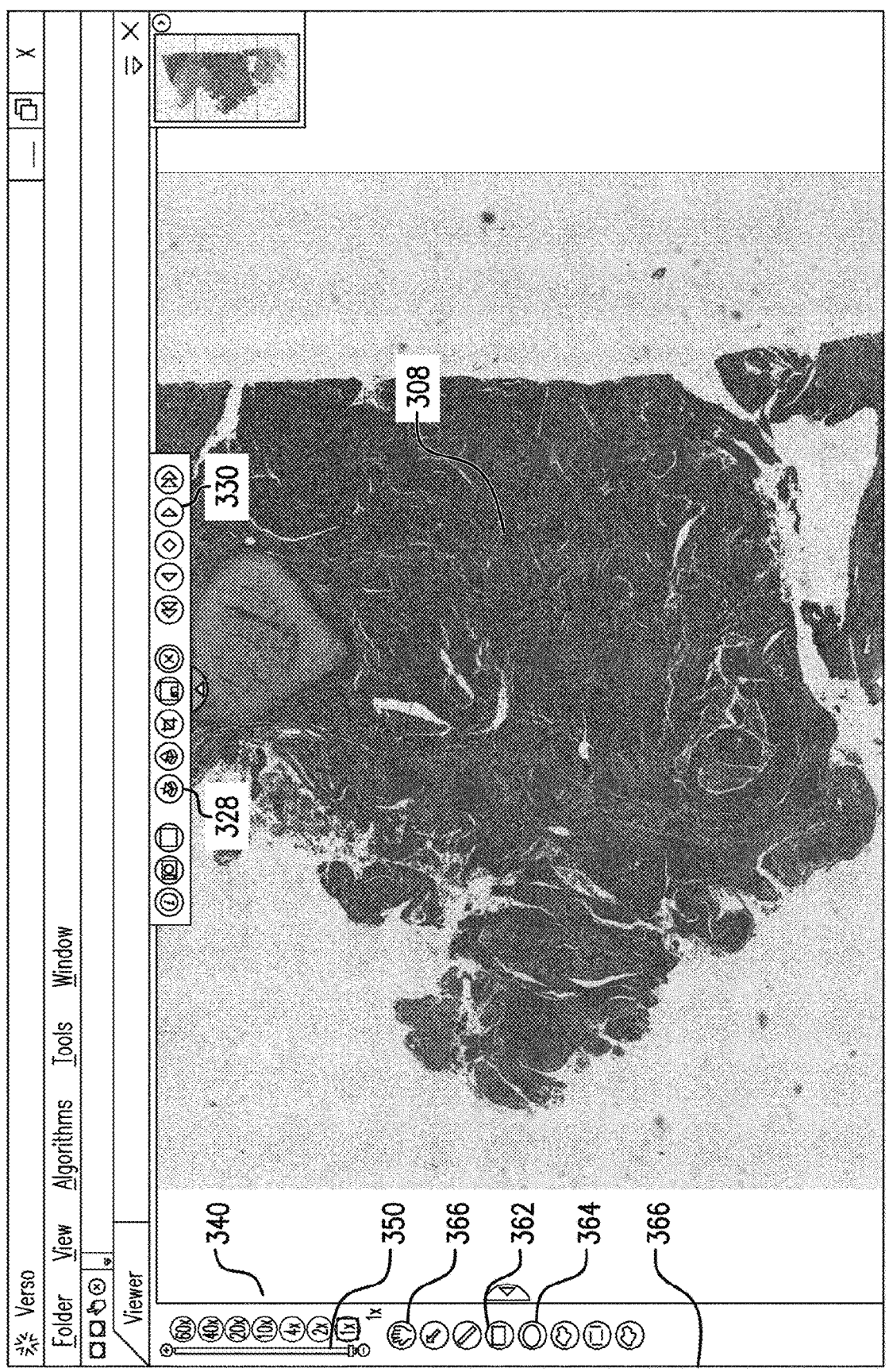
FIG. 6 is a screenshot of an embodiment of the annotation module GUI in which a digital slide may be viewed and annotated, and which may be launched from the home screen of FIG. 3.

When user annotations are not present, the user may open the source image in a viewer and mark regions of interest (create annotations). More specifically, as shown in FIG. 6, double-clicking on the source image launches a viewer interface (Verso Viewer) associated with the annotation module in which the source image (the HE image in the illustrated embodiment) is displayed and in which the source image can be manipulated and/or annotated. As illustrated, the Verso Viewer GUI includes a "Viewer" window 326 having a menu bar and a number of icons to facilitate a user's interaction with the displayed image, annotation module, and overall registration and annotation program. For example, import button 328 enables a user to import annotations, play button 330 enables a user to go from one annotation to the next, zoom buttons 340 and slider 350 enable a user to view the whole slide image at various resolutions. Furthermore annotations can be made, for example, using the annotation tool 360, which can be used to make rectangular, elliptical or polyline-based (like free hand drawing) regions using the rectangular 362, elliptical 364, or free-hand drawing 366 buttons respectively. Once the source image has at least one FOV marked, and after the marked annotations have been saved, a user can proceed with registration (for example, by clicking on the "Analysis" button 322 under the Image Registration tab 314 in the WorkBench environment).

In some embodiments, Verso Viewer may be opened independently. However, for ease of usability, double clicking on the source image in WorkBench results in opening the image in the Verso Viewer tab. As an example, if the viewer is opened first, the source image can be dragged and dropped into the viewer window; alternatively, the File→Open menu can be used to open the image.

Figure 7:
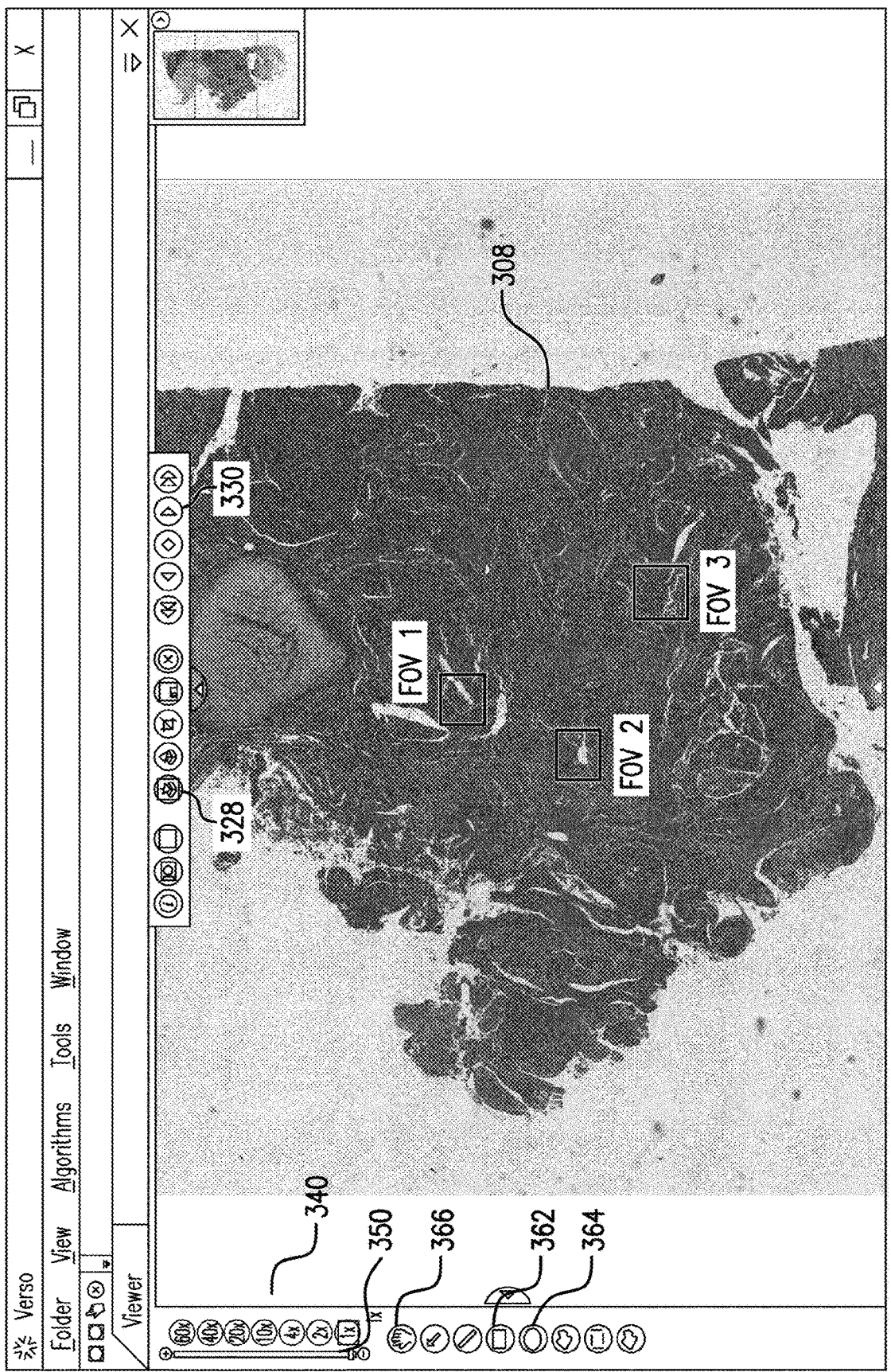
FIG. 7 is another screenshot of the annotation module GUI of FIG. 6 after a digital slide has been annotated.

FIG. 7 illustrates the same HE source image 308, also displayed in the annotation screen, but after it has been annotated using the tools 368 provided in the annotation module (e.g. Verso) and illustrated in the Figure. Specifically, three regions of interest (depicted as rectangles and labeled FOV1, FOV2 and FOV3) have been marked in the HE image 308. For each of these three regions in the HE image 308, the registration module should return the corresponding annotation in the target image (the IHC image 310 in the present example).

Figure 8:
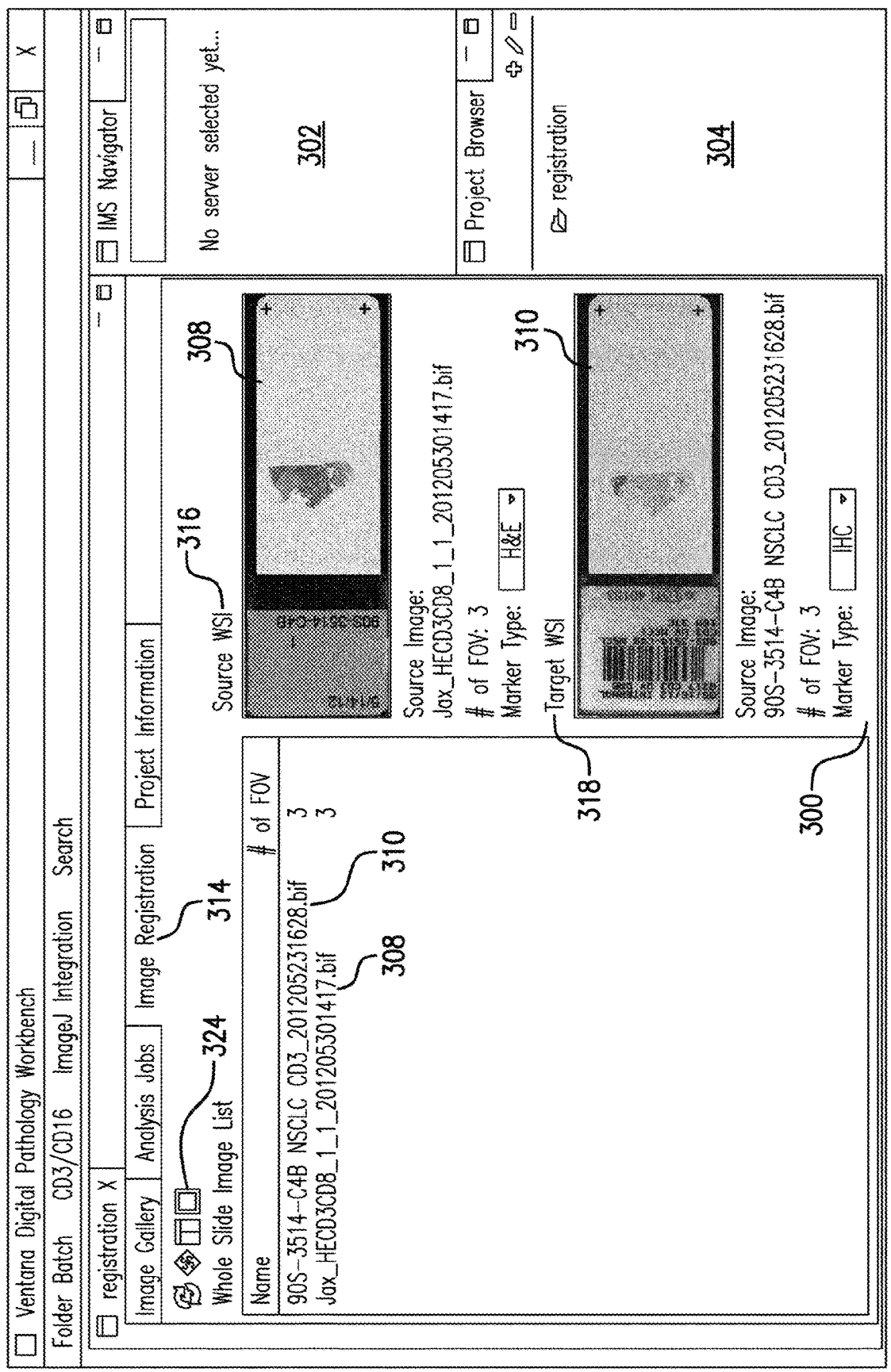
FIG. 8 is another screenshot of screen of FIG. 5 after performing image registration.

FIG. 5 together with FIG. 8, which is another screen shot of the image registration module (e.g. WorkBench) GUI, illustrate how changes in the annotation module (e.g. Verso) are updated to and reflected in the image registration module. Specifically, as shown in FIG. 5, under the image registration tab 314, after annotation in the annotation module, the # of FOV tab 309 is updated to indicate that three different FOV images ("FOV") are available for the HE source image 308. FIG. 8 illustrates updates to the image registration module after the user instructs the program to align the source image (in the example the HE image 308) and the target image (in the example the IHC image 310). Specifically, under the image registration tab 314, after image registration, three different FOVs are now also available for the IHC target image 310.

FIG. 9 is another screen shot of the annotation module (e.g. Verso) GUI. As shown, in the illustrated embodiment, once the image registration is completed through the WorkBench framework, the annotation screen automatically opens up in the annotation module with the HE source image 308 and the IHC target image 310 displayed together on the same screen, for example side-by-side as shown, with matching FOVs (i.e. the user-marked annotations 311a-c are displayed on the HE source image 308 and the corresponding retrieved annotations 311d-f are displayed on the IHC target image 310). In the illustrated embodiment, the whole slide images are shown at 1× resolution so that all 3 FOVs can be seen side-by-side for both whole slide images.

Figure 10:
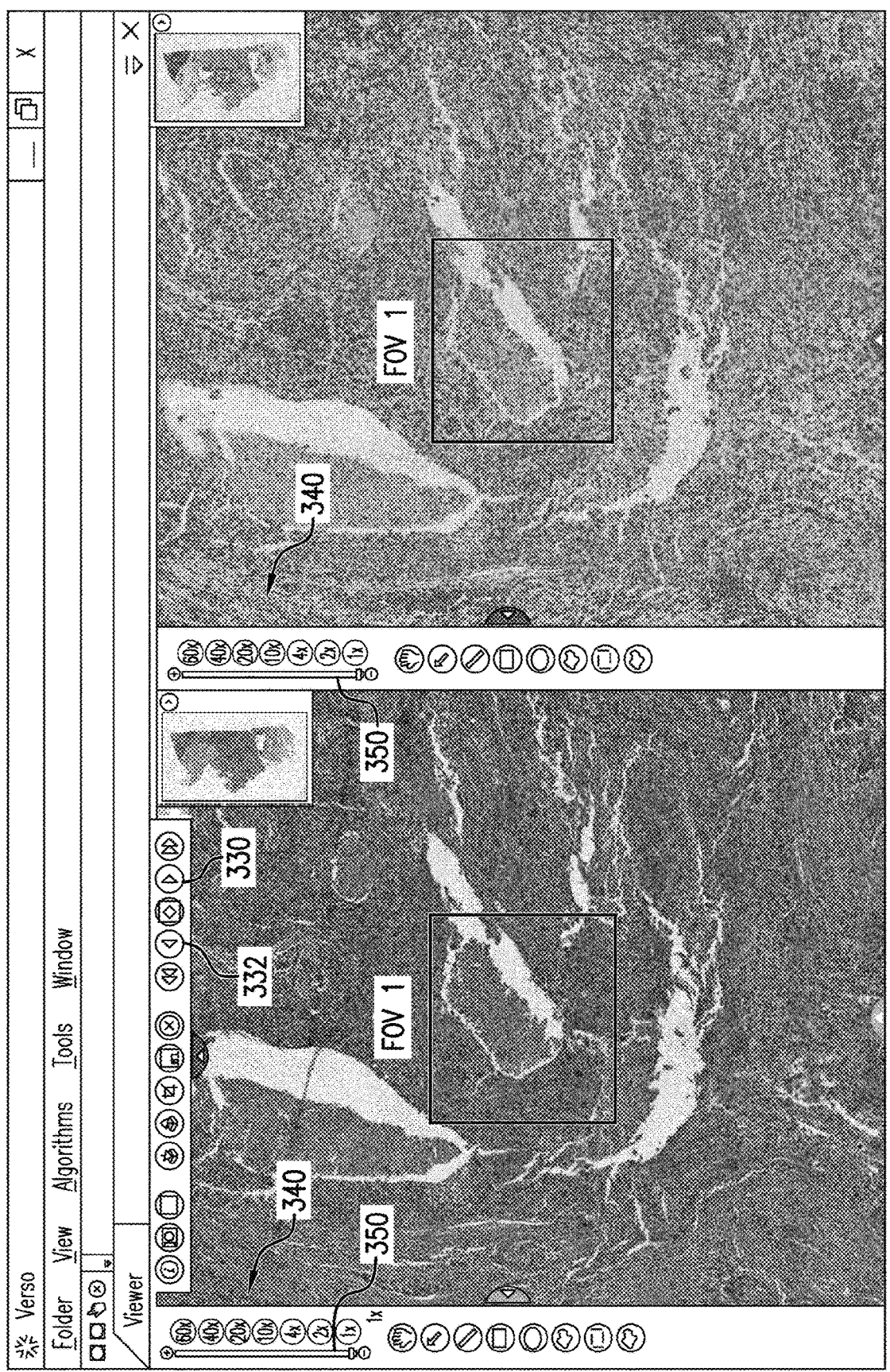
FIG. 10 is another screenshot of the annotation module GUI of FIG. 9, displaying a desired Field of View ("FOV") for a pair of registered images.

As shown in FIG. 10, in the illustrated embodiment, VersoViewer also includes a mode to view the annotated regions, one after the other. Clicking advance button 330 permits a user to progress forward from one annotation to the next, whereas previous button 332 permits a user to move from the currently viewed annotation to the previously viewed annotation. Also in the illustrated embodiment, as a user progresses from one FOV (for example the first FOV) to another FOV (for example the second FOV) for image 1, the display in right pane similarly progresses through the corresponding FOVs (here from the first FOV to the second FOV) for image 2.

Figure 11:
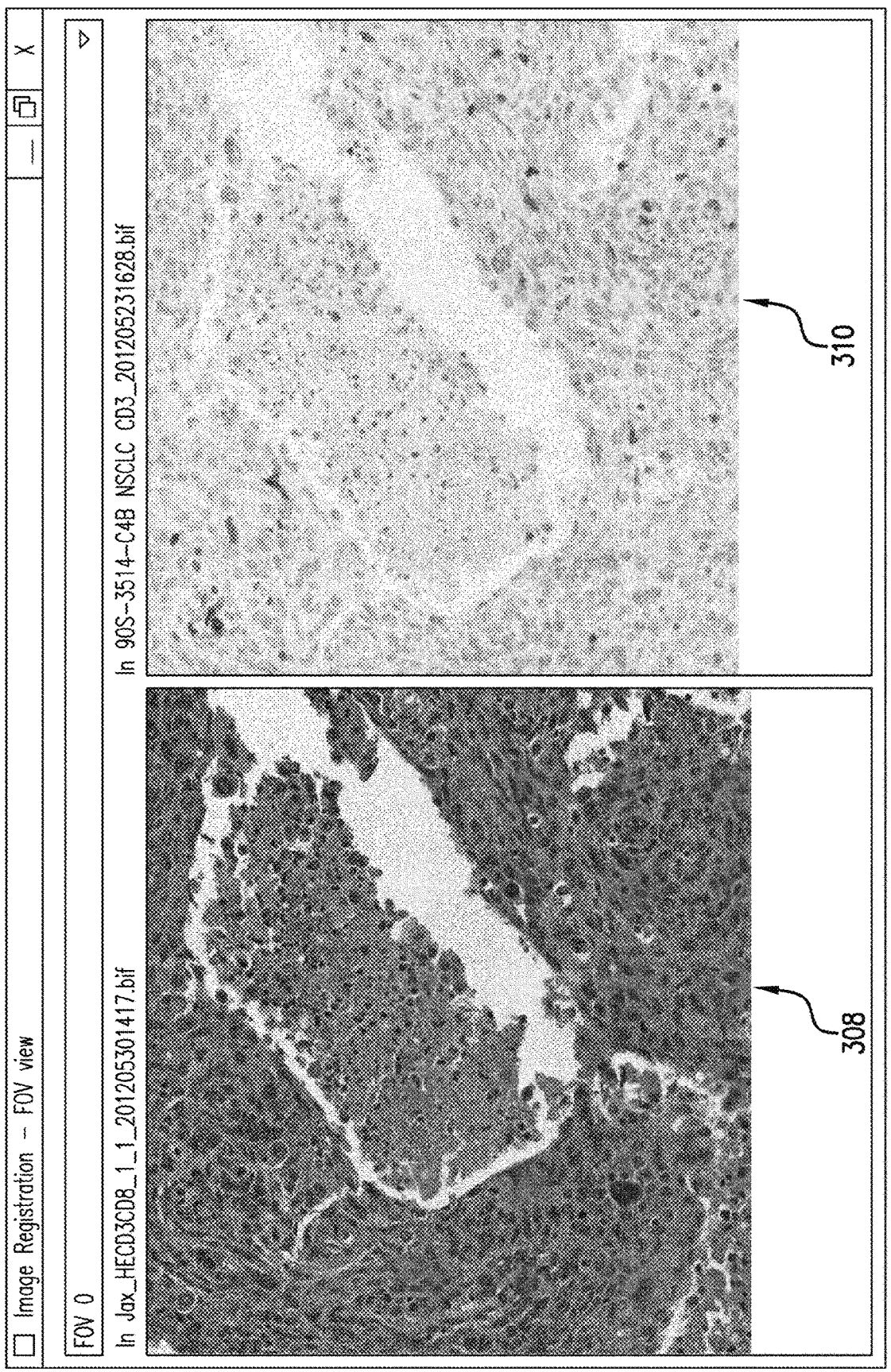
FIG. 11 is a screenshot of a window that is opened when a user selects the display button 310 under the image registration tab of the homescreen shown in FIG. 8.

FIG. 11 is a screen shot illustrating an alternative image display for viewing individual FOVs that is available under the image registration tab 314 of WorkBench. Clicking on the side-by-side image FOV viewing button 324 (FIG. 5) opens up the screen of FIG. 11. Similar to the VersoViewer implementation, the WorkBench view is also a split screen wherein at least a portion of the annotated HE source image 308 is displayed on one part of the screen and the corresponding portion of the annotated IHC target image 310 is displayed on the second part of the screen. FIGS. 10 and 11 depict the first annotation FOV in the annotation module and image registration module respectively, and illustrate how matched annotations can be compared using Verso Viewer as compared to WorkBench. As is apparent from the figures, in the annotation module (VersoViewer), the annotation is displayed in the middle of each split screen in addition to other parts of the slide image. By contrast, in the image registration module (WorkBench), only the annotation portion of the digital image can be seen. In the image registration module, similar to the annotation module, there is an option to run through all the available image pairs. In the example, there are three image pairs, which can be selected for independent viewing by the user. Accordingly, similar split screen views of the second and third annotation may also be launched in the annotation module and/or the registration module, which in the case of the registration module are accessed for example by using up/down arrows to scroll through the pairs of images. Also as illustrated, the annotation module provides the user with flexibility in terms of how to view the results. For example, the user can choose the resolution at which to view the image (4× is illustrated in the screen shot) using the zoom buttons 340 and/or zoom slider 350.

Figure 12:
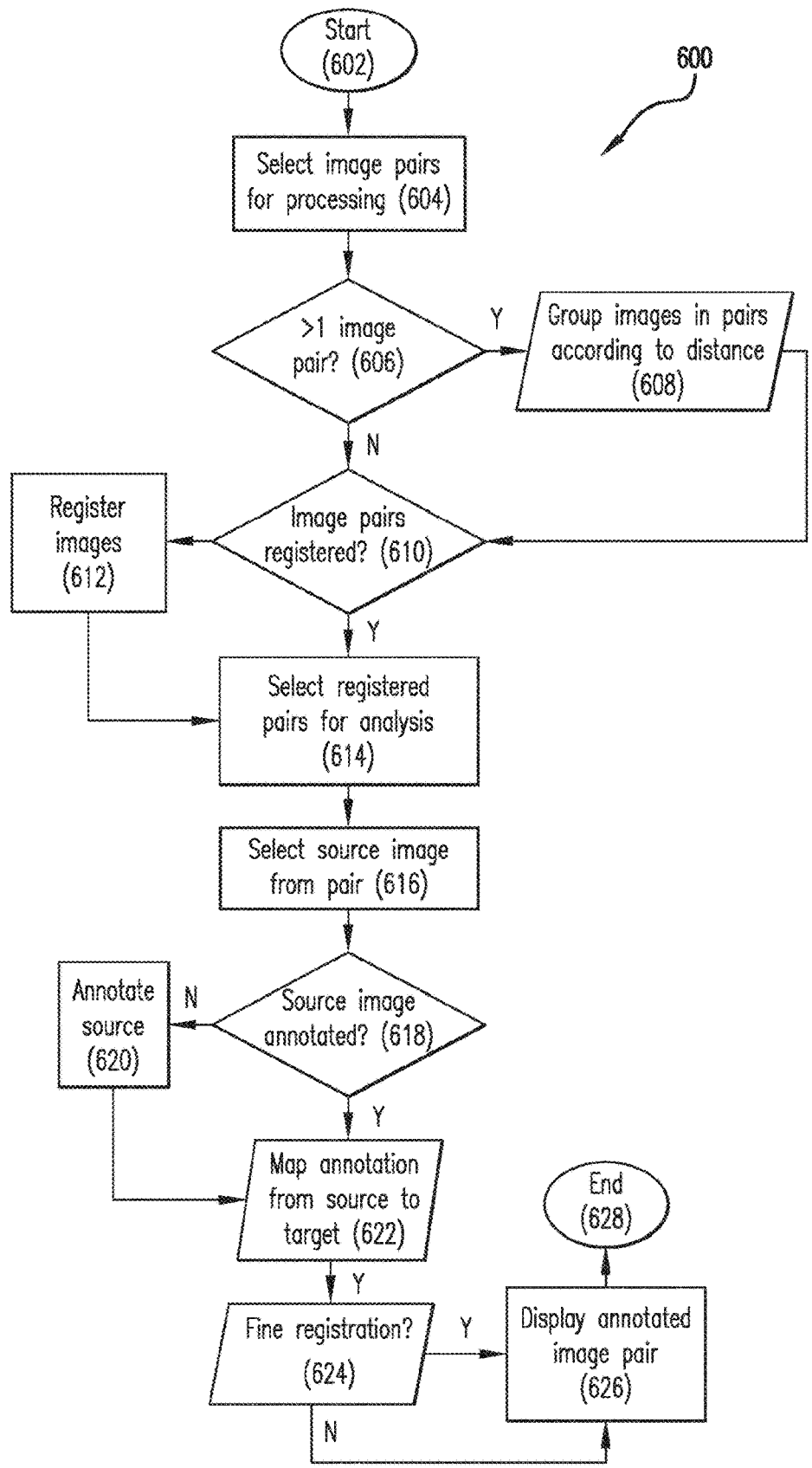
FIG. 12 is a flow diagram illustrating an embodiment of a method carried out by an image analysis software program in accordance with this disclosure.

FIG. 12 is a flow diagram illustrating an implementation of a method carried out by an embodiment of an image analysis software program in accordance with this disclosure. The image analysis software program enables a user to instruct the processor to align selected digital images (e.g. digital images of scanned slides of tissue sections, including whole slide images, partial slide images, or portions of whole or part slide images), annotate one or more of the images, map annotations from one or more images to other images, or combinations thereof. In some embodiments, the overall workflow for global alignment involves: generating a soft-weighted foreground image from an input image, wherein a region is assigned a higher weight in the soft-weighted foreground image where the stain contribution is higher (considering the two dominant stains) or the gradient (gradient image is computed from the grayscale image obtained from the color image) magnitude image is stronger; obtaining a binary mask from the soft-weighted foreground image; computing line-based features from the boundary of the binary mask; computing transformation parameters between two sets of line-features, wherein the transformation is expressed through rotation, reflection, and translation; and, transforming a first image to globally align it with a second image.

As shown in FIG. 12, the method 600 begins at the start block 602. At block 604, a set of image data or digital images is acquired (e.g. scanned or selected from the database) for manipulation. Each set of image data includes image data corresponding to, for example, a tissue section from a set of adjacent tissue sections of a single patient. Each set of digital images includes one or more digital images corresponding to a tissue section from a set of adjacent tissue sections of a single patient. Each image may be derived from tissue sections that are differently stained, or that are digitized using a different imaging mode, or both, as compared to another image. In some embodiments, the digital images are produced by scanning slides (e.g. microscope glass slides) prepared from adjacent tissue sections.

At block 606, if only a single image pair is selected, the process proceeds directly to block 610. If more than a single pair of images is selected, then the set of selected images is grouped into pairs at block 608 prior to proceeding to block 610. In some embodiments, image pairs are selected as adjacent pairs. Thus, for example, if the set of selected images includes 10 parallel, adjacent slices (L1 . . . L10), then L1 and L2 are grouped as a pair, L3 and L4 are grouped as a pair, etc. On the other hand, if information is not available as to which pairs of images are most similar to each other then, in some embodiments, images are grouped according to their distance apart, (e.g., inter-edge or inter-image distance corresponding to the chamfer distance between the edge-maps of the various images), pairing together images which are closest to one another. In exemplary embodiments of the present invention, an inter-edge/inter-image distance is utilized to pair of images. In some embodiments, edge-based Chamfer distance may be used to compute the inter-image/inter-edge distance. If the pairs of images have previously undergone a coarse registration process, such that the images have been coarsely aligned and the results have been saved, the process advances to block 614. Otherwise, at block 612 a coarse registration process is performed on the selected image pairs. The coarse registration process is described in further detail below.

Passing to block 614, the selected, and now registered (aligned), images are displayed on a common grid, with the images overlaid in a single image, displayed as separate images, or both, on a single monitor or spread across several monitors. At block 616, the client user may select one of the images from a pair of images as the source image. If the source image has already been annotated as desired, the process proceeds to block 622. Otherwise, the client user annotates the source image as desired at block 620. In some embodiments, the annotation is reproduced on that selected image, for example substantially simultaneously with the user inputting the annotation. In some embodiments, the user first identifies a source and target image, and if the source image has been annotated the user proceeds to instruct the program to register the images (for example undergo a coarse registration process). If the source image has not yet been annotated, the user may annotate the source image prior to registering the pair of images. At block 622, which may (or may not) occur substantially simultaneously with block 620, the annotation is mapped to the other image in the pair (the target image) and graphically reproduced on the target image. In embodiments wherein annotation occurs prior to coarse registration, the annotation may be mapped from the source image to the target image at substantially the same time as the pair of images is registered (aligned). At block 624, the user may choose to whether or not to engage in a fine registration process. If the user chooses to directly display the results without performing fine registration, the process proceeds to block 626. Otherwise, at block 624 a fine registration process is performed on the selected image pairs, for example to optimize the location of the mapped annotations and/or alignment of the images. The fine registration process is discussed in further detail below. At block 626, the annotated image pair is displayed with the results of the fine registration process (or the annotated image pair may be displayed only with the results of the coarse registration process if fine registration is not used). The method then ends at the final block 628.

Figure 13:
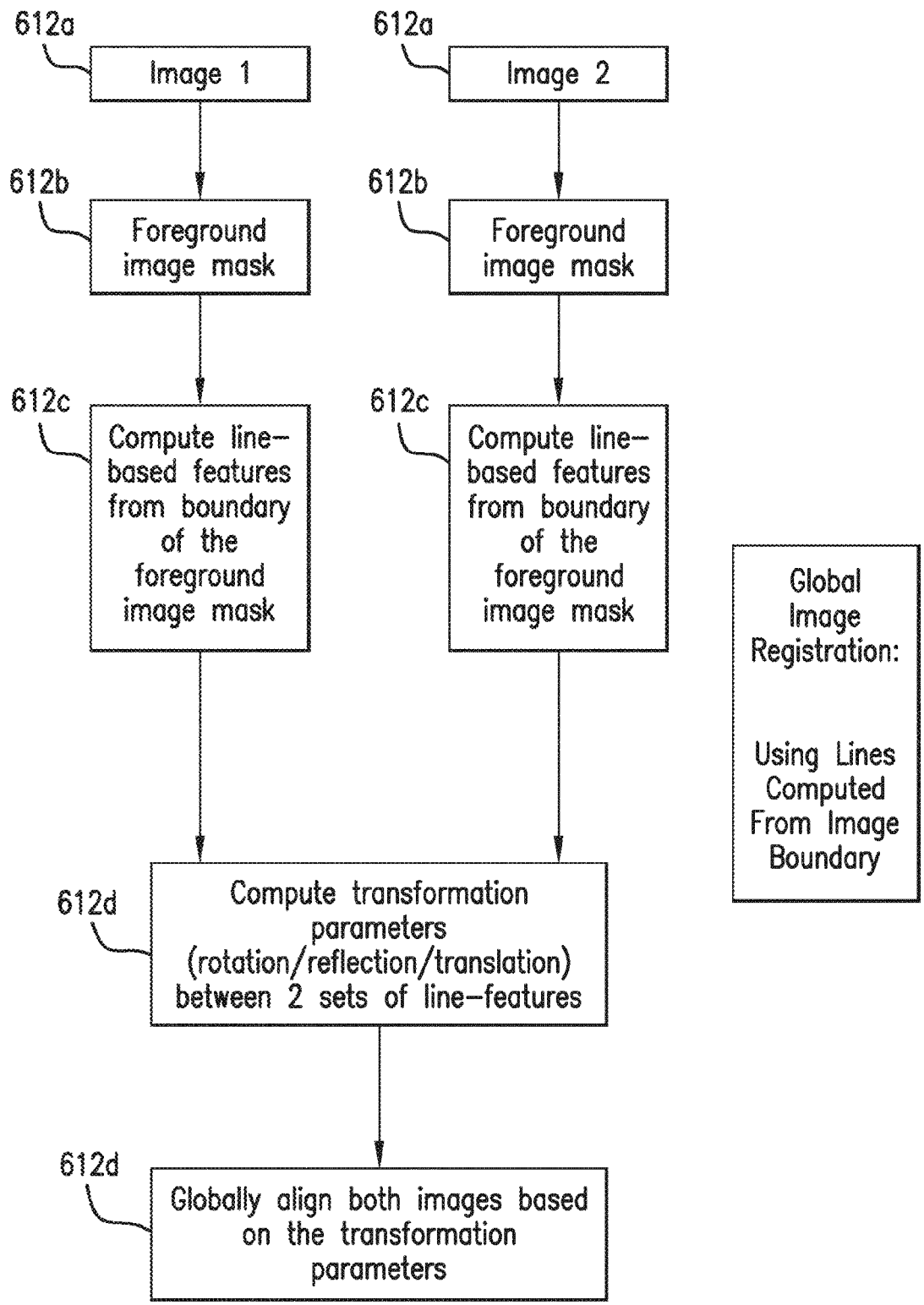
FIG. 13 is a flow diagram illustrating a line-based global image registration process in accordance with an embodiment of this disclosure.
Figure 14A:
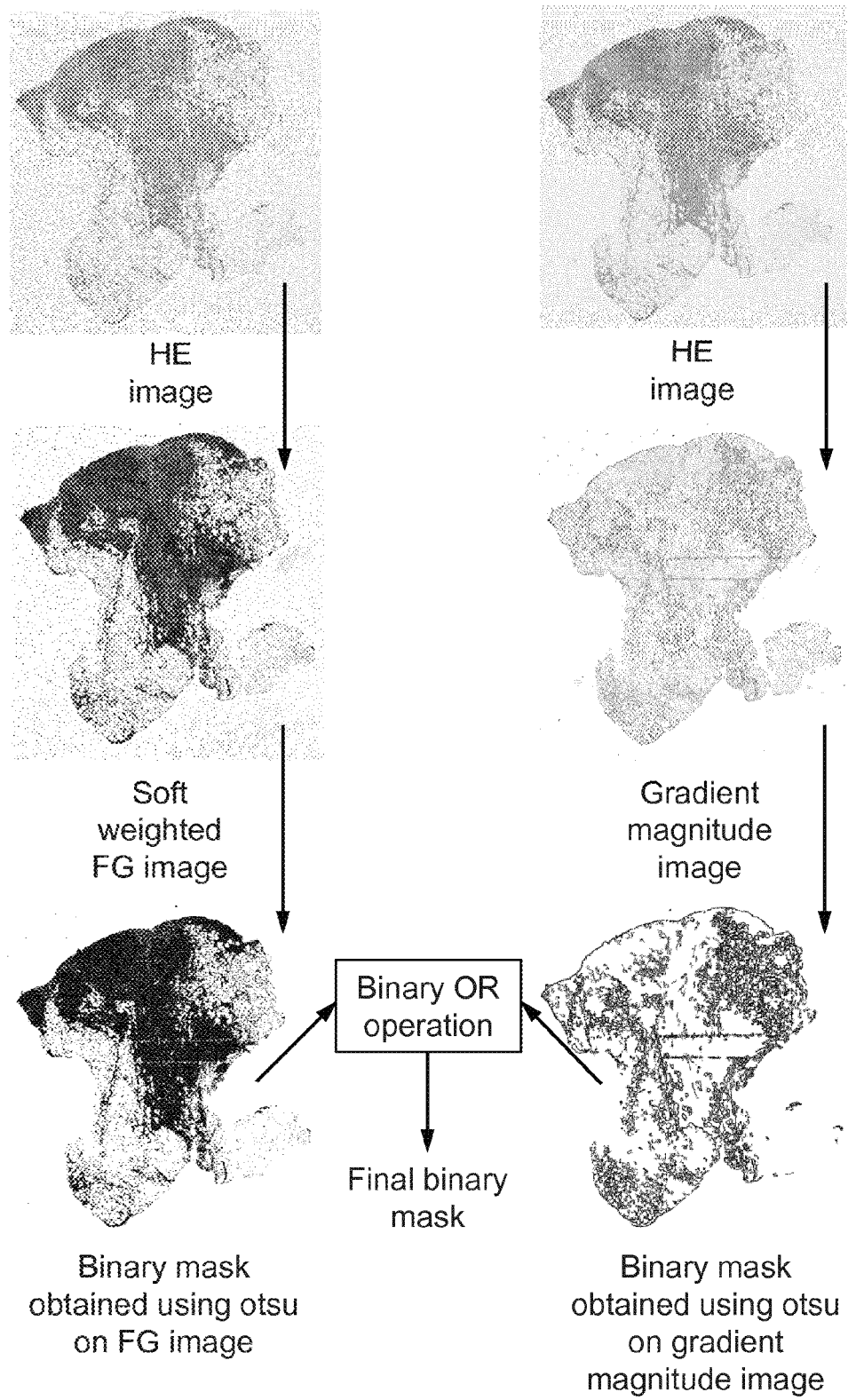
FIG. 14A illustrates the basic steps of an embodiment of generating a foreground mask, which may be part of the global image registration process of FIG. 13.
Figure 14B:
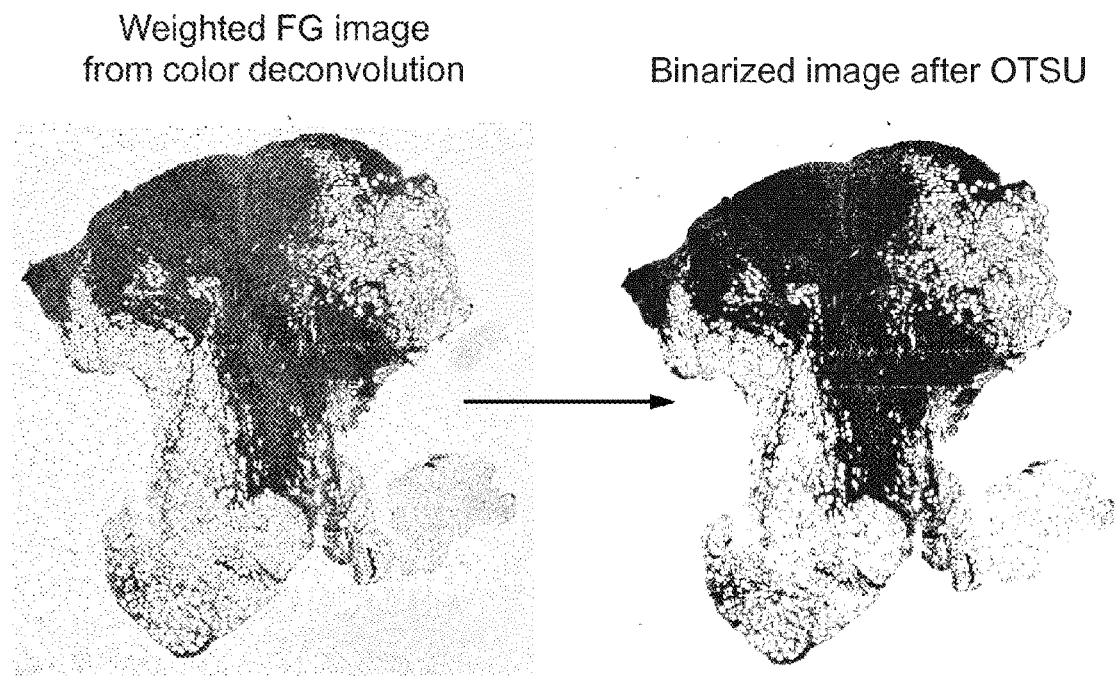
Figure 14C:
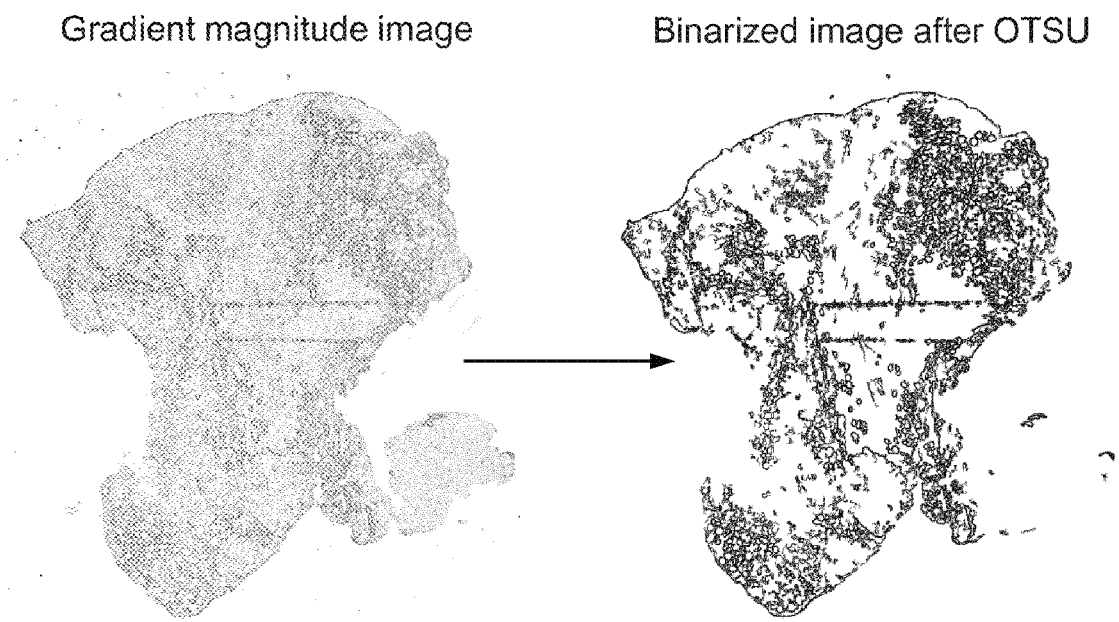
Figure 15A:
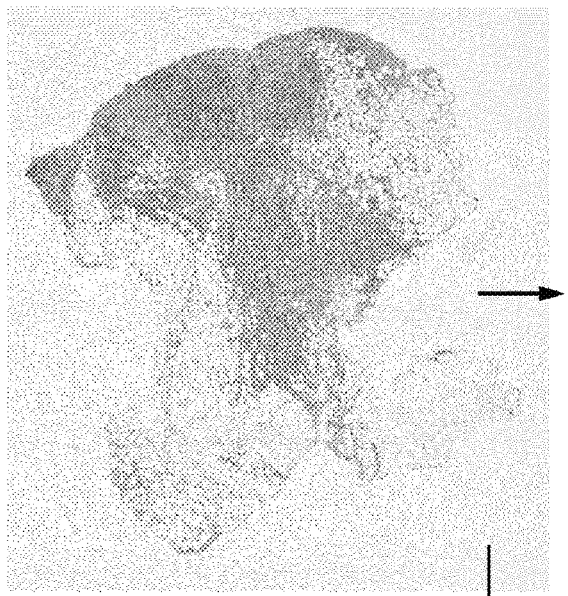
Figure 15B:
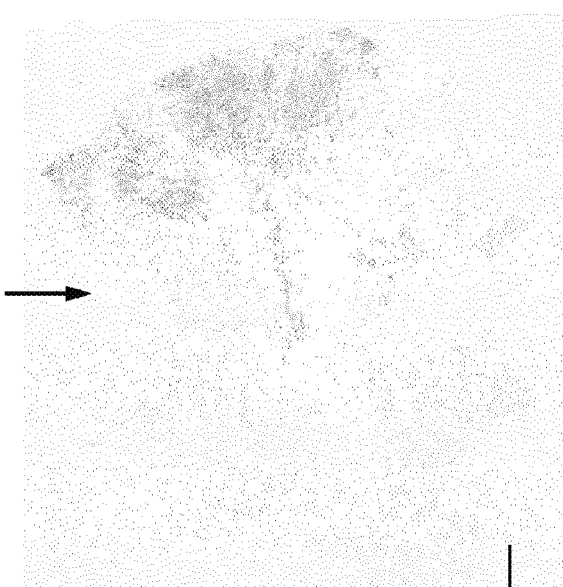
Figure 15C:
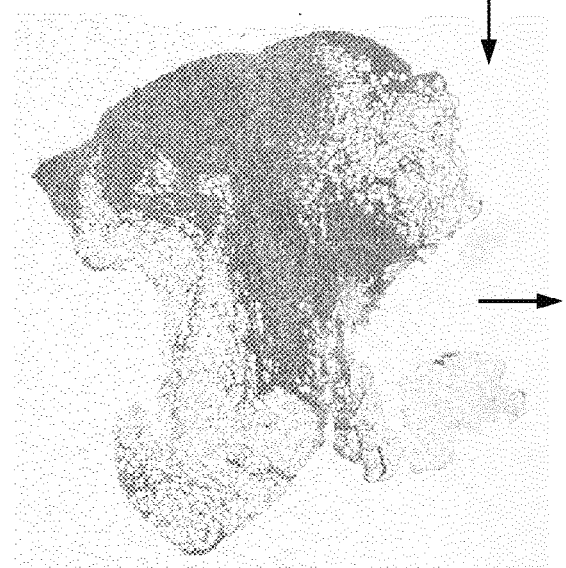
Figure 15D:
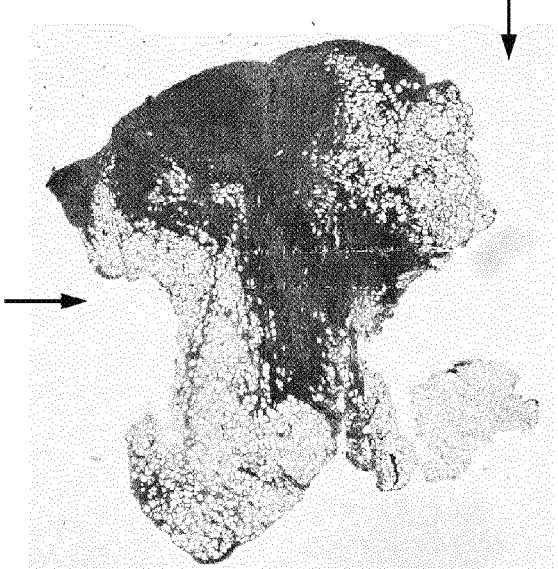

FIG. 13 illustrates further details regarding block 612, the coarse registration process. Prior to initiating the coarse registration process, two images are selected for alignment (block 612a, FIG. 13; block 604, FIG. 12). As shown in FIG. 13, in some embodiments, the coarse registration process, which is applied to the two images, may involve: 1) obtaining a foreground image mask from each of the selected images (block 612b, FIG. 13; 2) computing line-based features from the boundary of the foreground image mask (block 612c, FIG. 13); and, 3) computing global transformation parameters (e.g. rotation, scale, shift) (block 612d, FIG. 13) between the two sets of lines resulting from the computations of 612b. Finally, as shown in FIG. 13, the two images are aligned using the global transformation parameters and may be displayed on a common grid on a monitor (or monitors) (block 612e).

FIGS. 14 to 19 illustrate further details of an embodiment of block 612b, wherein foreground image masks are obtained for the source and target images. In some embodiments, the method involves obtaining a soft-weighted (continuous valued) foreground image from each of the selected images. In some embodiments, as shown in FIG. 14a, the method involves obtaining a soft-weighted foreground image (based on stain components) from each of the target and source images, separately obtaining a gradient magnitude image (the gradient is computed based on the grayscale image and may help distinguish foreground regions where the stain contribution is very faint but have higher gradient magnitude as compared to smoother background regions with lower gradient magnitude) from each of the target and source images, applying OTSU thresholding on each of the soft-weighted foreground image and gradient magnitude image to obtain a binary mask image for the soft-weighted foreground image and a binary mask image for the gradient magnitude image, and OR-combining the two binary masks to obtain a final binary image mask (final foreground image mask or foreground image mask). FIG. 14b provides a larger scale view comparing the soft-weighted color unmixed or deconvolved image with the binary mask generated from the soft-weighted image, whereas FIG. 14c provides a larger scale comparison of the gradient magnitude image and the binary mask generated from it.

FIGS. 15 to 19 illustrate further details for generating soft-weighted image masks. "Soft-weighted" images are images corresponding to a soft weighting applied to the stain images with higher/lower values denoting that a certain stain color is more/less present. The soft weighting method is a method for obtaining a continuous-domain valued image from a discrete valued unsigned character image (e.g., wherein the range of the pixel values is 0-255). In some embodiments, the goal of obtaining the soft weighted foreground image is to separate tissue from non-tissue in the digital image and to provide for scaling and translation estimation. In some embodiments, the continuous-valued foreground images are obtained by applying a color de-convolution process to the selected digital images, which may be scans of glass slides prepared from tissue sections which have been stained. The specific color de-convolution process depends on the specific stain, and will be described herein by way of three examples: HE stain, IHC stain and fluorescent image.

Figure 16:
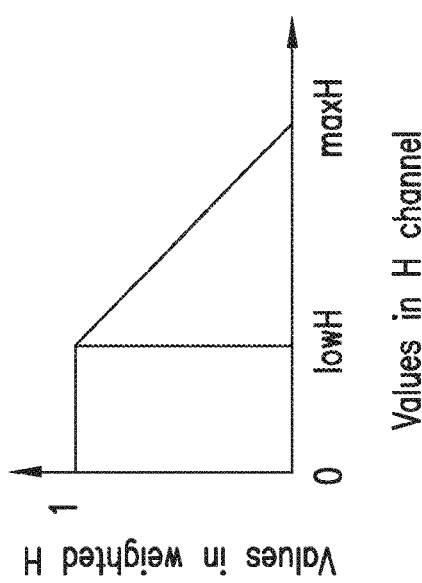
FIG. 16 illustrates an embodiment of the soft weighting process of FIG. 14 for an H channel image.

FIGS. 15 to 16 illustrate the process for generating a soft-weighted binary mask from an HE image. As shown in FIGS. 15 to 16, the image extraction process is essentially a color de-convolution process, wherein the color stain is removed from the original HE image (FIGS. 15A-15C) and optionally an OTSU thresholding is applied to the color deconvolved image to result in the soft weighted binary mask (FIG. 15d).

More specifically, as shown in FIG. 15, an H channel image and an E channel image are obtained by removing two image components (specifically H (haematoxylin: Blue colored) and E (Eosin: red colored)) which have been mixed/added to form the composite image HE image of FIG. 15A. The HE color de-convolution can be performed by any method known in the art, for example as described in: Ruifrok A C, Johnston D A, Quantification of histological staining by color deconvolution, *Anal Quant Cytol Histol* 23: 291-299, 2001, which is herein incorporated by reference in its entirety. In some embodiments, after the two (H and E) channels are obtained (e.g. after the color de-convolution process), an OTSU and soft weighting method are performed on each of the H channel image and E channel image. The OTSU method is a thresholding method used to automatically perform histogram shape-based thresholding and is described, for example, in Otsu, Nobuyuki, "A Threshold Selection Method From Gray-Level Histograms" Automatica 11.285-296 (1975): 23-27, which is herein incorporated by reference in its entirety. The weighted H image (e.g., a image that reflects the stain contribution of the H channel, where the weighted H image has higher/lower values when the stain contribution of the H channel is higher/lower) is obtained after OTSU-based thresholding and soft weighting on the H-channel image. Similarly, the weighted E image is obtained after OTSU-based thresholding and soft weighting on the E-channel image. Finally, the weighted HE image is obtained as follows: each pixel in the weighted HE image=maximum of (H channel image pixel, E channel image pixel), i.e. it is the maximum of the corresponding pixel values in H and E channel images.

FIG. 16 illustrates an embodiment of the soft weighting process for the H channel image. After OTSU-based thresholding is performed, the threshold value (to separate the foreground from the background H channel) is taken as levelH. Accordingly, levelH is the OTSU-based threshold computed on the H channel, lowH is the value of fraction*levelH, and maxH is max(H channel image), i.e. the maximum value of all the pixels in the H channel image. As may be understood from this description, in H and E channels, lower intensity values correspond to darker regions in the image; also, higher intensity values correspond to lighter regions in the image (in an unsigned char image, for pixel values in [0,255], the darker regions correspond to pixels close to 0 and brighter regions correspond to pixels close to 255); e.g., in the H channel, darker regions denote areas where haematoxylin (blue component) is more strongly expressed. In the final weighted H image, a high intensity value for these darker regions (more blue regions) is expected. Similarly, in the weighted H image, a low intensity value for lighter regions, where the contribution of the haematoxylin is low, is expected.

In some embodiments, the objective is to obtain a weighted H image that is higher in value when the contribution of the blue haematoxylin channel is high, and lower in value when the blue channel contribution is low. FIG. 16 illustrates how the soft-weighted image (i.e., an image that is weighted based on the stain content in an image and is weighted higher in pixels with higher stain content; i.e. for an HE image, the regions with higher contribution from H or E channels get assigned higher weight values) can be computed. To generate the weighted image (e.g. for HE), each pixel of the individual weighted image (weighted H image and weighted E image) is assigned a value. In FIG. 16, the fraction term controls the mapping between pixels in the H image to the weighted H image, and from pixels in the E image to the weighted E image; to select this parameter, we conducted an experiment on a data set of training images. The value 0.8 for the fraction term gave us the best registration output based on the result from this data set. As an example, however, pixel values of the H image are mapped to weighted H image as follows: when fraction=1, then lowH (lowH=fraction*levelH, where levelH is OTSU-based threshold computed on the H channel)=levelH (corresponding to fraction=1), and image pixels having a blue channel contribution (value of H channel) less than lowH get assigned a value of 1. Thus, when the fraction is 1, the weighted H image has non-zero pixel intensity values in the range [low H=levelH, maxH] (where level H represents the OTSU-based threshold computed on the H channel and maxH represents the maximum value of the H channel image). In some such embodiments, for pixel/pixel intensity values in the H channel which are lower than levelH, the weighted H image is assigned a value of 1. For pixel values in the H channel which lie in the range [lowH, maxH], the weighted H values are in the range [1,0]. A range of [lowH, maxH] in the H channel is mapped to a range of [1,0] in the weighted H image. In some embodiments, the fraction is an empirically-chosen value of 0.8. Accordingly, the weighted H image will have values in a wider range of pixel values; often, in fainter image regions, the threshold returned by OTSU may not be accurate and hence, lower values are assigned to the weighted image for image pixels with values slightly higher than the OTSU threshold.

Figure 17A:
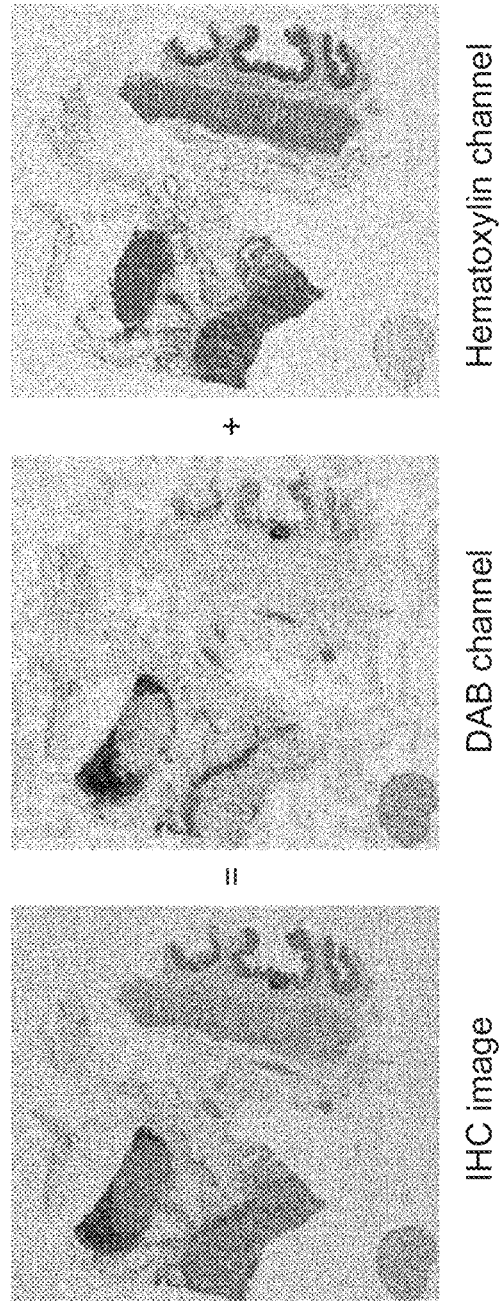
FIGS. 17A to 17C illustrate an IHC image and its corresponding soft weighted foreground image, as well as details of the basic steps or a portion of the basic steps of an embodiment generating a foreground mask in the coarse registration process of FIG. 13.
Figure 17B:
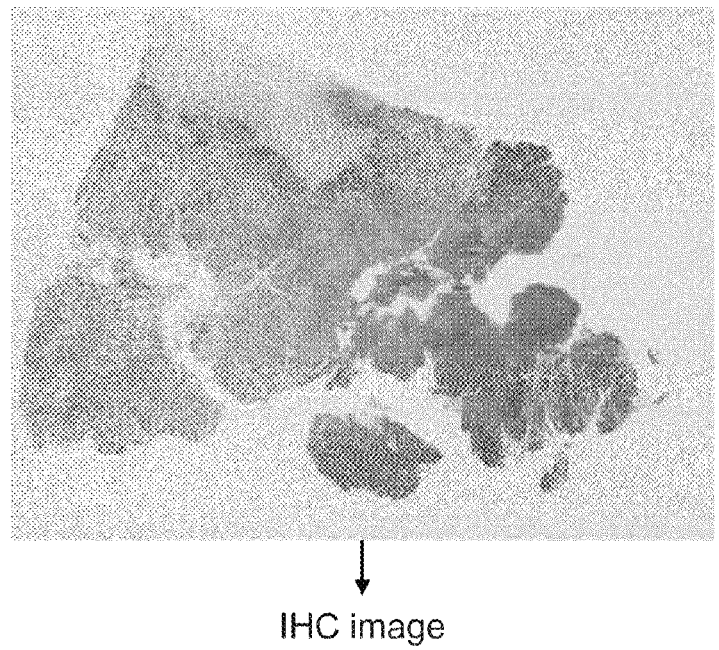
Figure 17C:
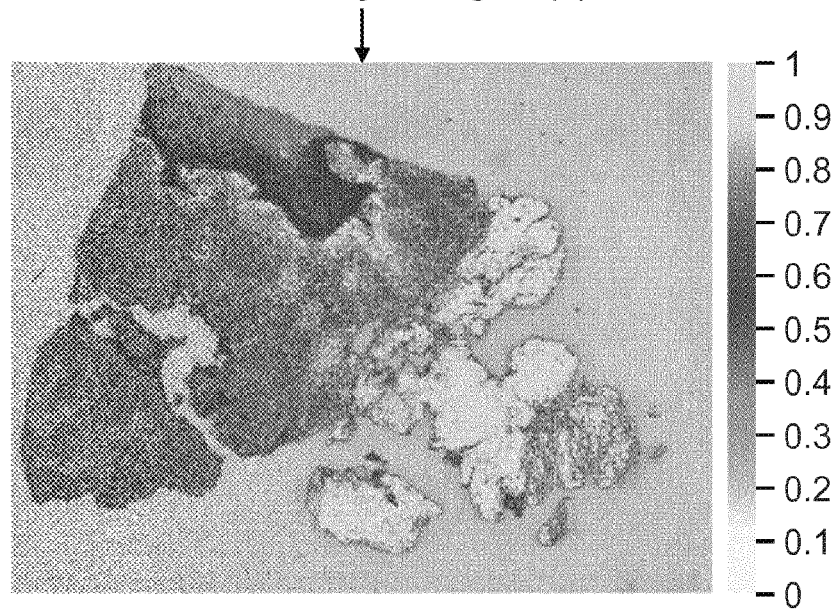
Figure 18:
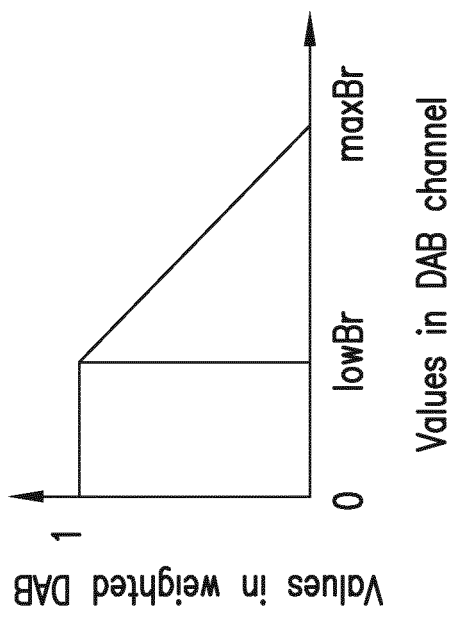
FIG. 18 illustrates an embodiment of the soft weighting process of FIG. 14 for the IHC image of FIG. 17.

FIGS. 17 and 18 together illustrate the soft weighting foreground image extraction process for an IHC image. As shown in FIG. 17A, the image extraction process is essentially an unmixing or color de-convolution process, wherein the main color components are extracted from the image. For example, in the illustrated embodiment, haematoxylin (blue) and DAB (brown) are the main stain components, and unmixing or color deconvolution is used to separate the IHC image into these two color channels.

The same soft weighting method, as used for HE images, is now used for the IHC image. The weighted DAB image is obtained after OTSU-based thresholding and soft weighting on the DAB channel image. Similarly, the weighted Hematoxylin image is obtained after OTSU-based thresholding and soft weighting on the Hematoxylin image. Finally, the weighted IHC image is the max(weighted DAB image, weighted Hematoxylin image), per pixel; i.e. each pixel in the weighted IHC image is the maximum of the two corresponding pixels in DAB and Hematoxylin channel images.

FIG. 18 illustrates an embodiment of the soft weighting process for the DAB channel image. After OTSU-based thresholding is performed, the threshold value (to separate the foreground from the background in DAB (brown) channel) is taken as levelBr. Accordingly, levelBr is the OTSU-based threshold computed on the Brown channel, lowBr is the fraction*levelBr (here, the fraction is 0.8), and maxBr is max(brown channel image); i.e. maxBr is the maximum of all the pixel values in the brown channel image. For values in the Brown channel which are lower than lowBr, the weighted DAB image is assigned a value of 1. A range of [lowBr, maxBr] in the Brown channel is mapped to a range of [1,0] in the weighted DAB image. As may be understood from this description, in brown and blue channels, lower intensity values correspond to darker regions in the image. Similarly, higher intensity values correspond to lighter regions in the image. The overall process results in generating a soft weighted foreground image as shown in FIG. 17C from the original IHC image as shown in FIG. 17B.

A soft weighted foreground image can also be extracted from a fluorescent image, for example by preparing a grayscale image and applying OTSU to transform the grayscale image to a binary image. In some embodiments, as the starting point for extracting the soft weighted foreground image, a grayscale thumbnail image is read off from the fluorescent image. Then, OTSU is used to transform the grayscale thumbnail image to a binary image. And then, connected components (connected components is a technique used to study a binary image and separate it into multiple non-overlapping blobs—i.e., regions made up by connected pixels, to access the separate non-touching blobs individually) is performed on the binary image, for example as described in Samet, Hanan, "An Improved Approach to Connected Component Labeling of Images," *Proceedings*, IEEE Computer Society Press, 1986, which is herein incorporated by reference in its entirety. In some embodiments, the connected components analysis is used to return contiguous regions in the binary image using standard algorithms. Out of the contiguous regions returned after connected components determination, some of the outlier regions are discarded based on predetermined criteria such as smaller cell sizes (once all the non-overlapping blobs are extracted, then those blobs which are smaller than a certain size are discarded and so the foreground corresponds to only those blobs which satisfy a size constraint).

The result of the process is to have foreground regions in the thumbnail image, where each region exceeds a certain minimum size. In some embodiments, if N is the total number of ON pixels in the foreground image (here N denotes the total number of pixels which are non-zero in the foreground image, an ON pixel is a pixel in the foreground image which is greater than 0), the minimum size expected from a single blob obtained from a connected component should be at least N/20—the choice of minimum area, wherein N/20 is empirically chosen. For example, the parameter N/20 was chosen based on experiment results from a data set of training images wherein a range of this parameter was tested on the images and the value N/20 provided the best result. For these regions, a higher value is assigned for the soft weighted foreground image where the thumbnail image is darker. In a thumbnail image, the intensity of the glass is generally in the region [240-255] and the tissue content is generally darker than the glass and has pixel values<240. Therefore, the darker regions in a thumbnail image, corresponding to regions with lower intensity, are more likely to be tissue regions. Similarly, the lighter regions in the thumbnail, where the intensity values are generally higher than in the tissue region, generally correspond to the glass.

Although in some embodiments, the foreground image is the binary mask generated from the soft-weighted foreground image (obtained for example by the methods described above), in other embodiments, as shown in FIG. 14, the foreground image is a binary OR combination of two binary masks—the binary mask generated from the soft-weighted foreground image, and a binary mask generated from a gradient magnitude image. In some embodiments, the gradient magnitude image is computed from a grayscale image obtained from the color image, and then using Gaussian first derivatives along x and y axes, using kernels with a standard deviation (a Gaussian function is specified by 2 parameters, mean and standard deviation: here the mean is 0 and standard deviation is set to σ) σ of 3 along both axes. With respect to the soft-weighted foreground image, the relevant foreground regions should have higher contribution of the stain components as compared to the background region, and with respect to the gradient magnitude image, there can be foreground regions where the stain contribution can be very faint and the gradient magnitude can help distinguish between fainter foreground regions and smother background regions.

After the foreground image mask is extracted, global transformation parameters are estimated (block 612*d*, FIG. 13). In some embodiments, a first image (for example, the source image where the user/pathologist has marked certain regions) and a second image (for example a target image which the user/pathologist has selected for retrieving the marked regions) are compared to compute the global transformation. As shown in FIGS. 19-20, in some embodiments, the comparison is done using a line-based features approach (block 612c, FIG. 13). Generally, as shown in FIG. 19, to find correspondence between images coming from parallel slices but different stains (markers), modalities (brightfield/ fluorescent), scanners, etc., in some embodiments: line-based features are computed along the boundary of the effective binary mask (foreground image) generated from the soft-weighted foreground and gradient magnitude images for each pair of source/target images; and, as shown in FIG. 13, transformation parameters are then computed between the two sets of line-based features, with the transformation being expressed through rotation, reflection and translation. In some embodiments, line-based features may be computed in the internal parts of the tissues; however, the inventors have empirically observed that tissue wear-and-tear may result in more significant changes in the internal parts of the tissue as compared to the boundary regions. ("Wear and tear" mismatch or flips can result from the slide preparation process, such as when staining and laying the stained tissue slide on a scanner bed.) Accordingly, line-based image registration may still be used in the case of wear-and-tear mismatch between source and target images, for example where the wear-and-tear is to internal and not boundary structure (it has been empirically observed that the wear-and-tear effects are more observed for internal structures as compared to the boundary structure, and so the registration algorithm is more likely to end up with matching lines if we consider the boundary lines as compared to using line segments representing internal structures), or where it is still possible to match greater than 50% of the line segments extracted from the source image, can be matched with corresponding line segments in the target image.

Figure 22:
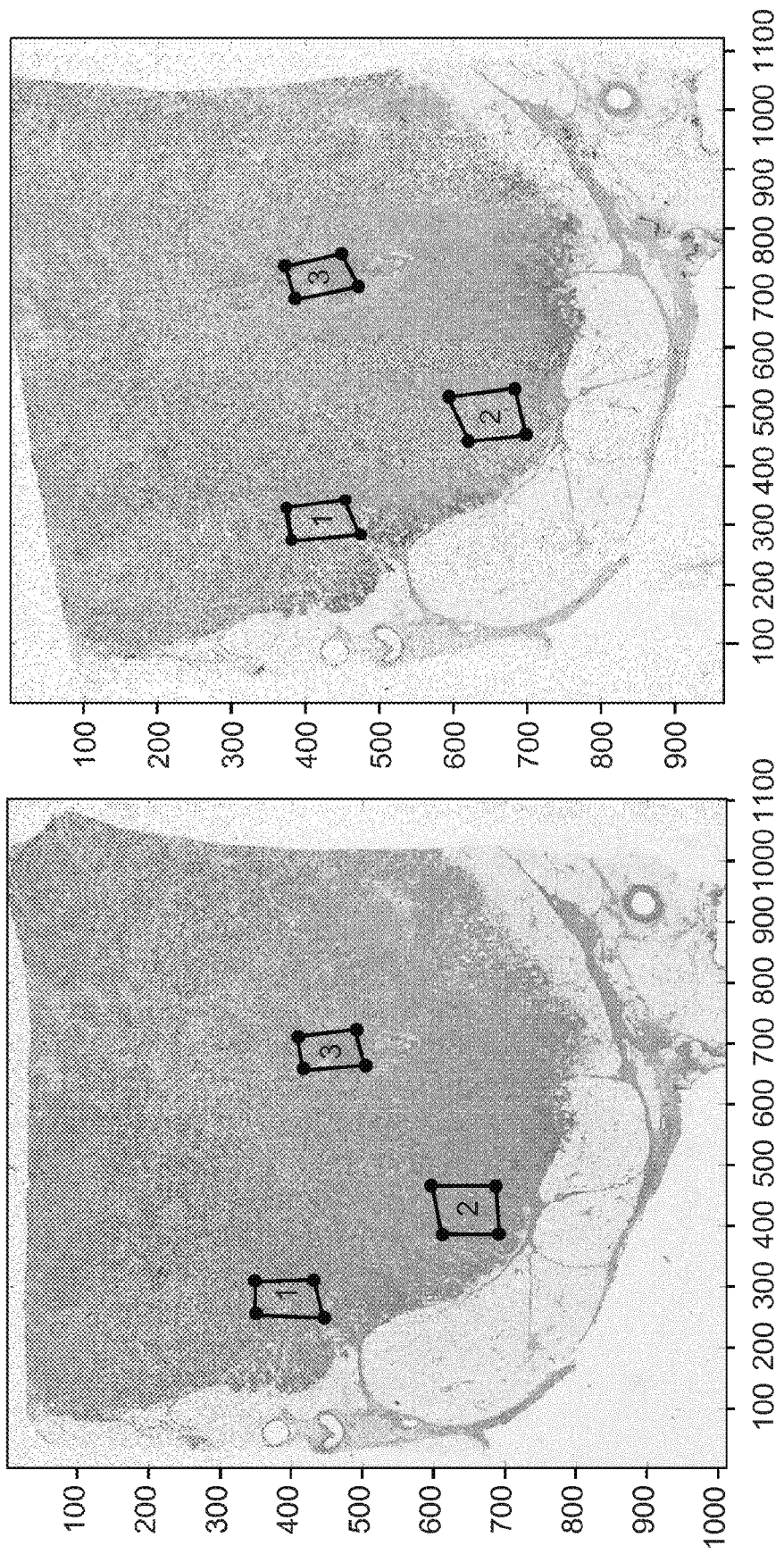
FIG. 22 illustrates the applicability of embodiments of coarse registration processes according to this disclosure for slides which have rotation and shift mismatch.
Figure 24:
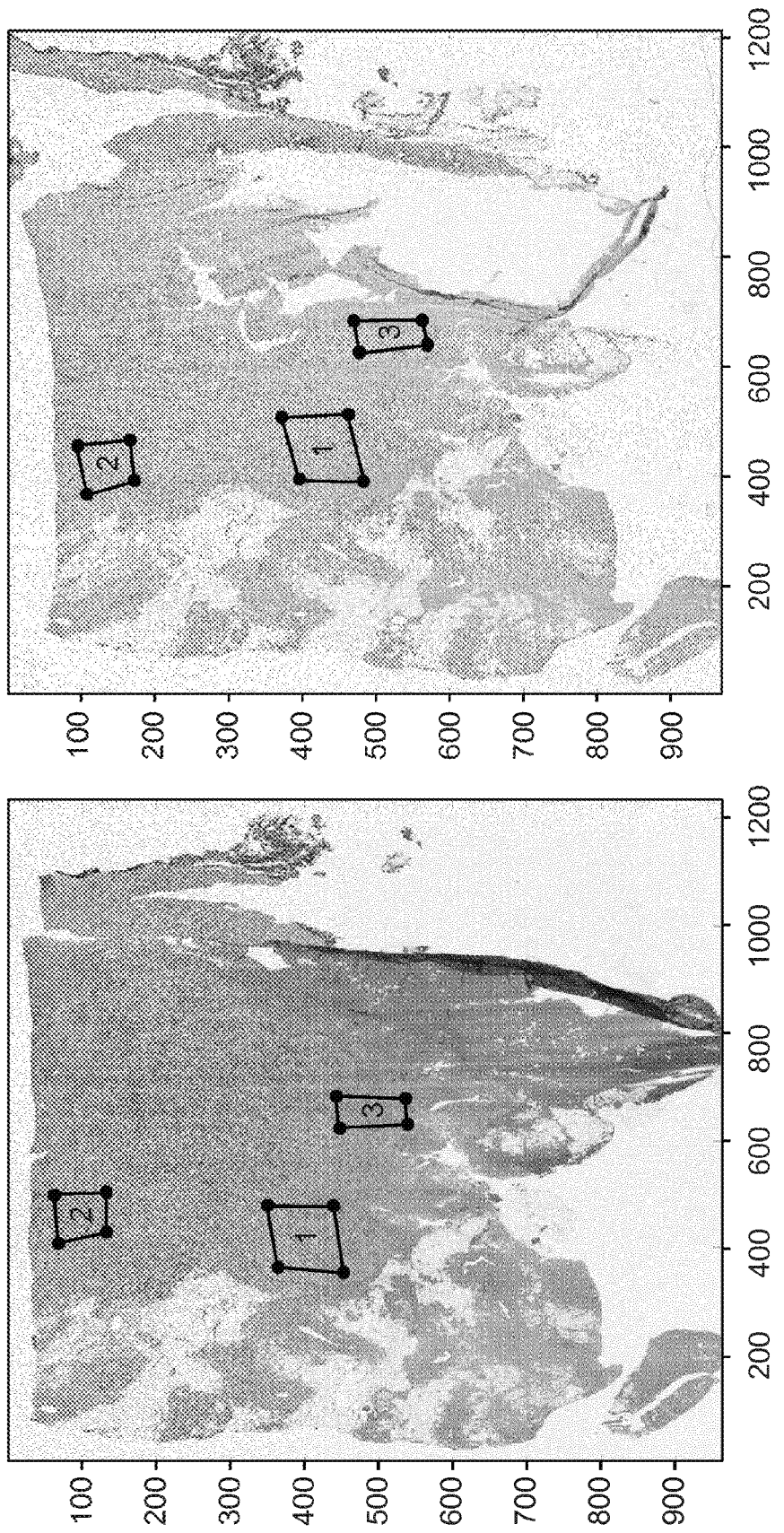
FIG. 24 illustrates the applicability of embodiments of coarse registration processes according to this disclosure for slides which have wear-and-tear mismatch.
Figures 27A, 27B:
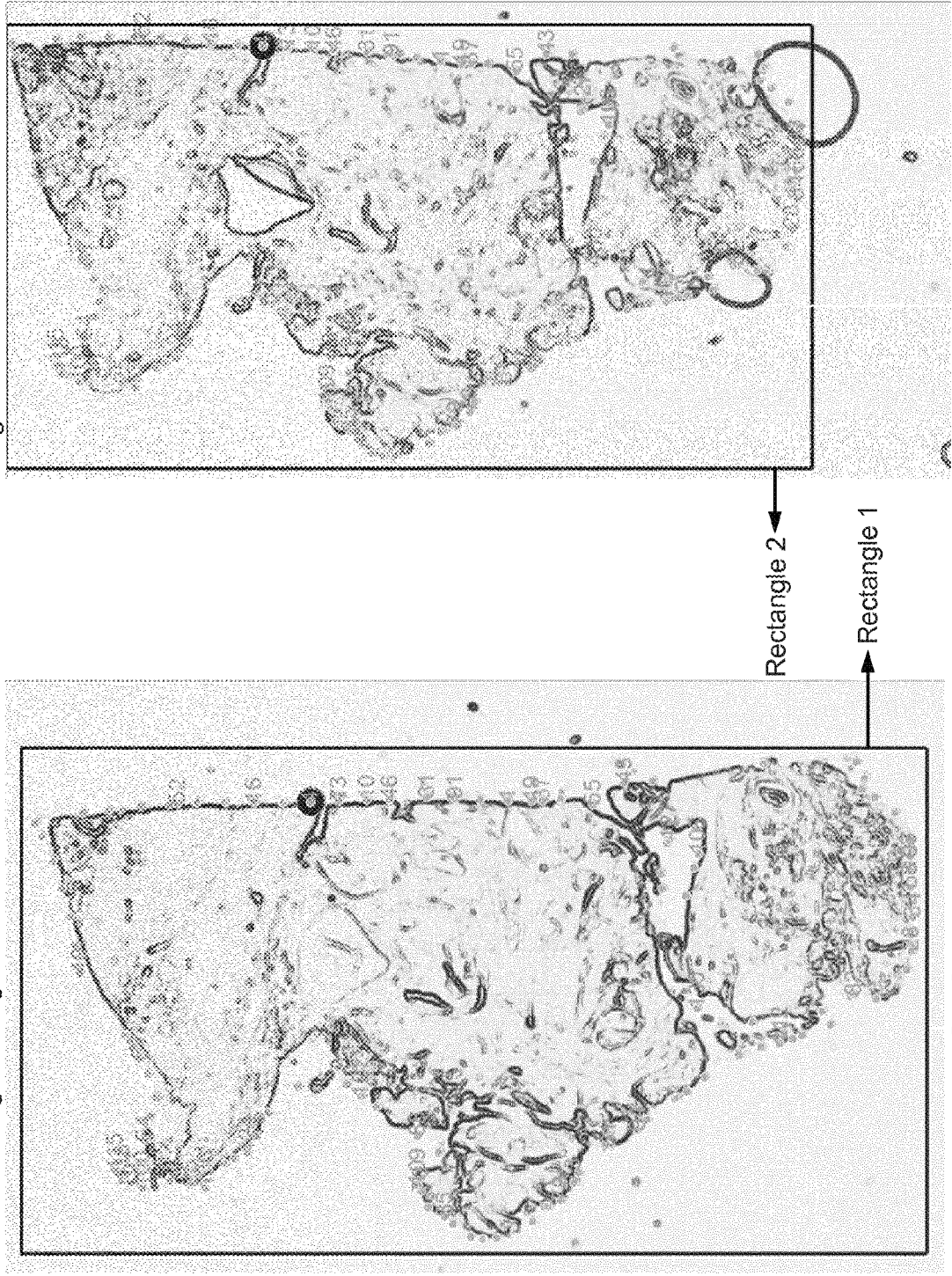
FIGS. 27A and 27B collectively illustrate an example of slide AOI mismatch, to which embodiments of the registration process in accordance with this disclosure may be successfully applied.

FIG. 20A to 20E illustrate an embodiment of a method for determining line-based features and finding a transformation (e.g. rotation plus x,y shifts) which transforms a first image in a first area to a second image in a second area, even sometimes in cases of defects such as insertions, deletions, AOI mismatch, streaky black lines, etc. Mismatch among slides of adjacent tissue sections may result because of the physical process involved in preparing the slides. For example, while scanning, the regions of a physical slide which get picked up for high resolution scanning constitute the Area of Interest ("AOI"). As shown in FIG. 21A, when two adjacent slices are scanned, the AOI picked up may differ between two slides; there can be enough variations between two adjacent slides so that the AOI captured during the scans of these slices may have additional/missing regions in one as compared to the other. Hence, one scanned image may be a subset/superset of the other. As a result, as shown in FIG. 21B, there can be mismatch in the retrieved regions after registration. As shown in FIG. 21C, line-based embodiments according to this disclosure may nonetheless automatically compute the proper subset regions to be compared in both images. Similarly, as shown in FIGS. 22 to 24, embodiments of the line-based registration method may properly transform a first area of a first image into a second area of a second image despite defects such as small rotation angle and x-y translations between slides (FIG. 22), or large rotate angles (a 180 degree angle in the case of FIG. 23), or wear and tear (FIG. 24). In other words, registration embodiments according to this disclosure may successfully align two adjacent images despite mismatch, for example based on aligning a transformed version of a certain subset of a first image to a certain subset of a second image, and does not require alignment of the entirety of one image to the entirety of the other image. FIGS. 27A and 27B illustrate an example of AOI mismatched slides which may nevertheless be properly aligned by the line-based registration process described herein.

As the examples of FIGS. 20A to 20D illustrate, in some embodiments, line-based features are computed by breaking each image into smaller-sized windows, with the size being chosen to return appropriate results (i.e. the windows are sized such that lines may be distinguished). In some embodiments, the windows are 80×80 windows—a line segment is computed per window, with window shifts of 40 pixels along x and y axes.

Figure 20A:
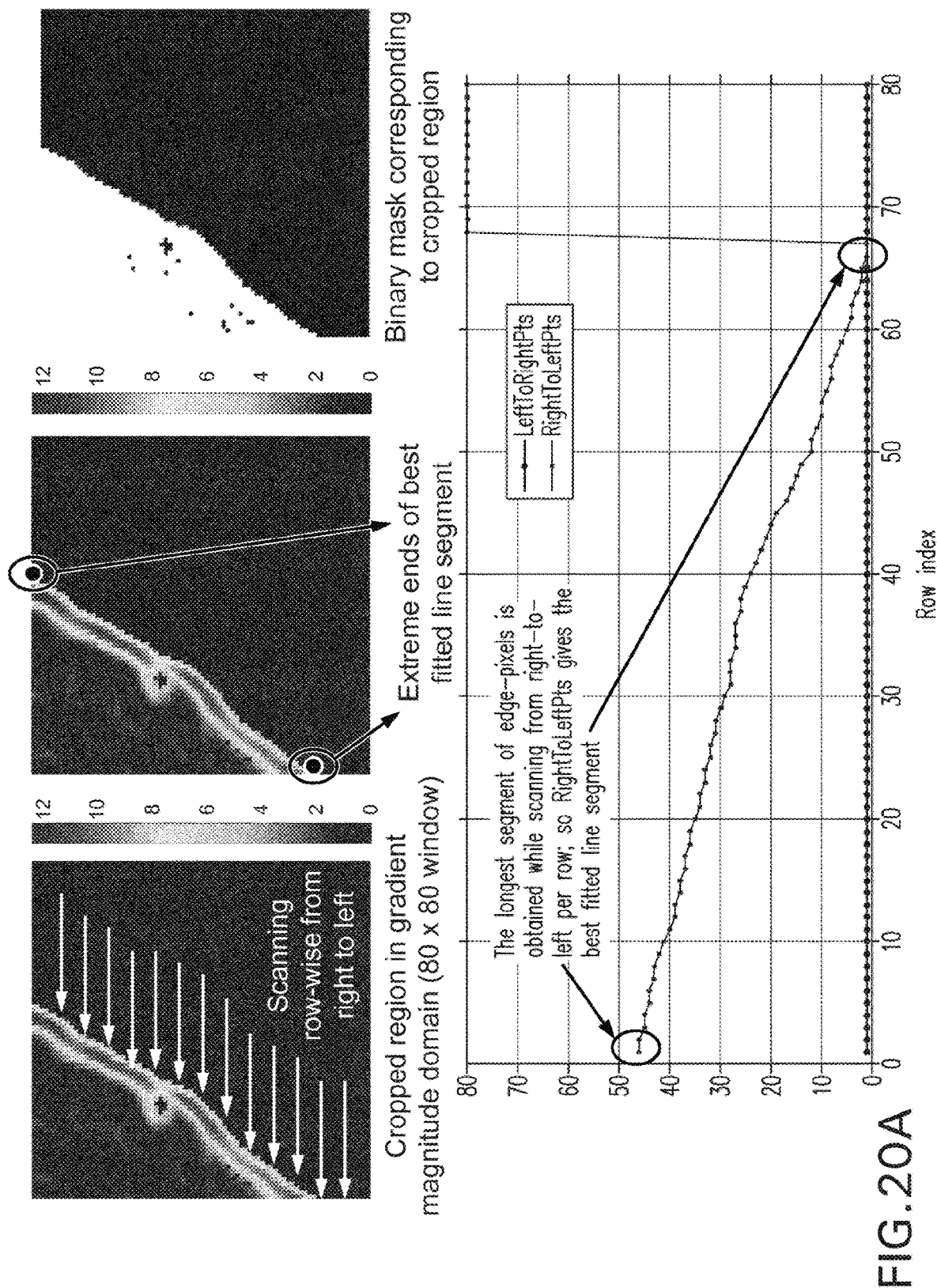
Figure 20B:
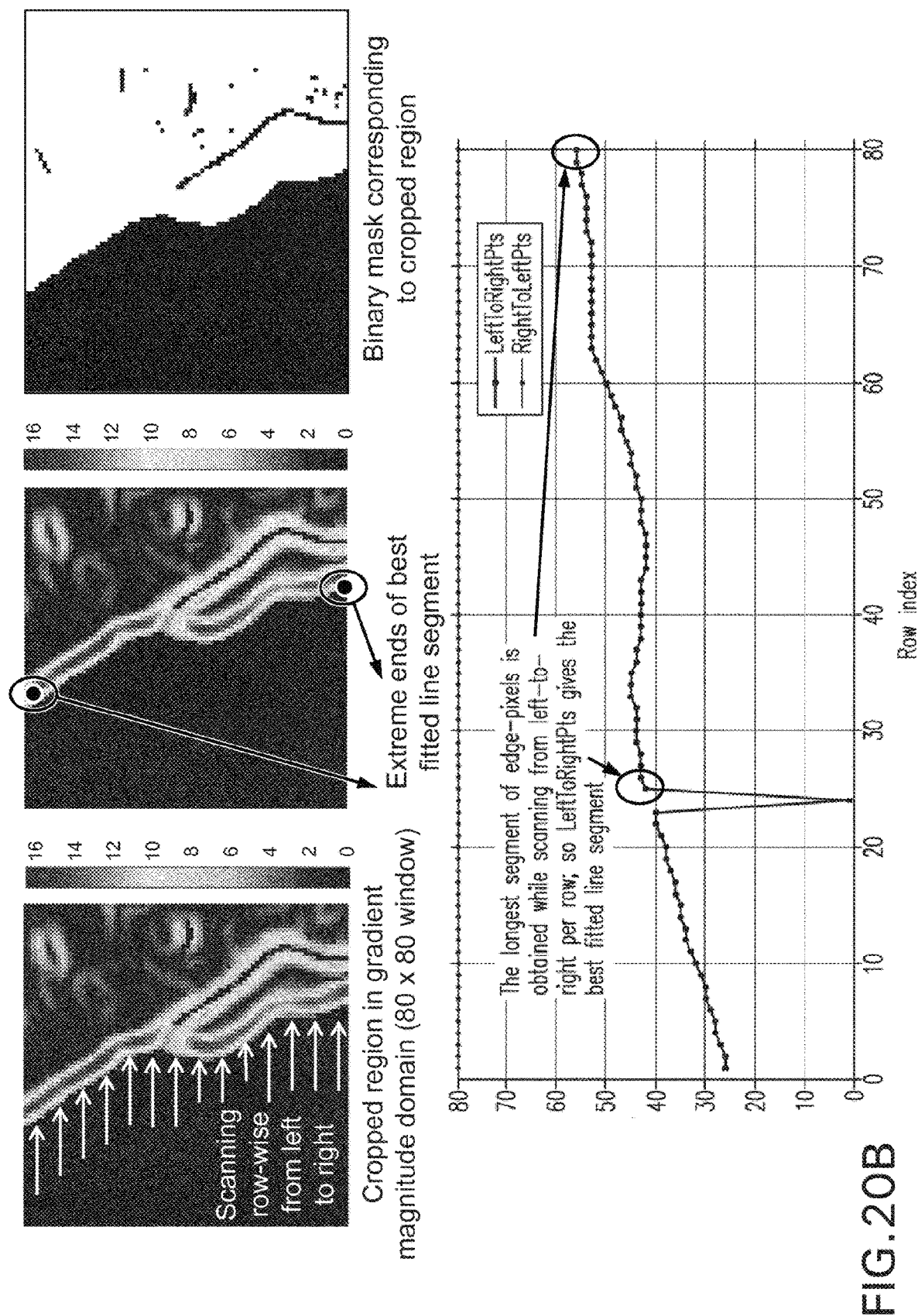
Figure 20C:
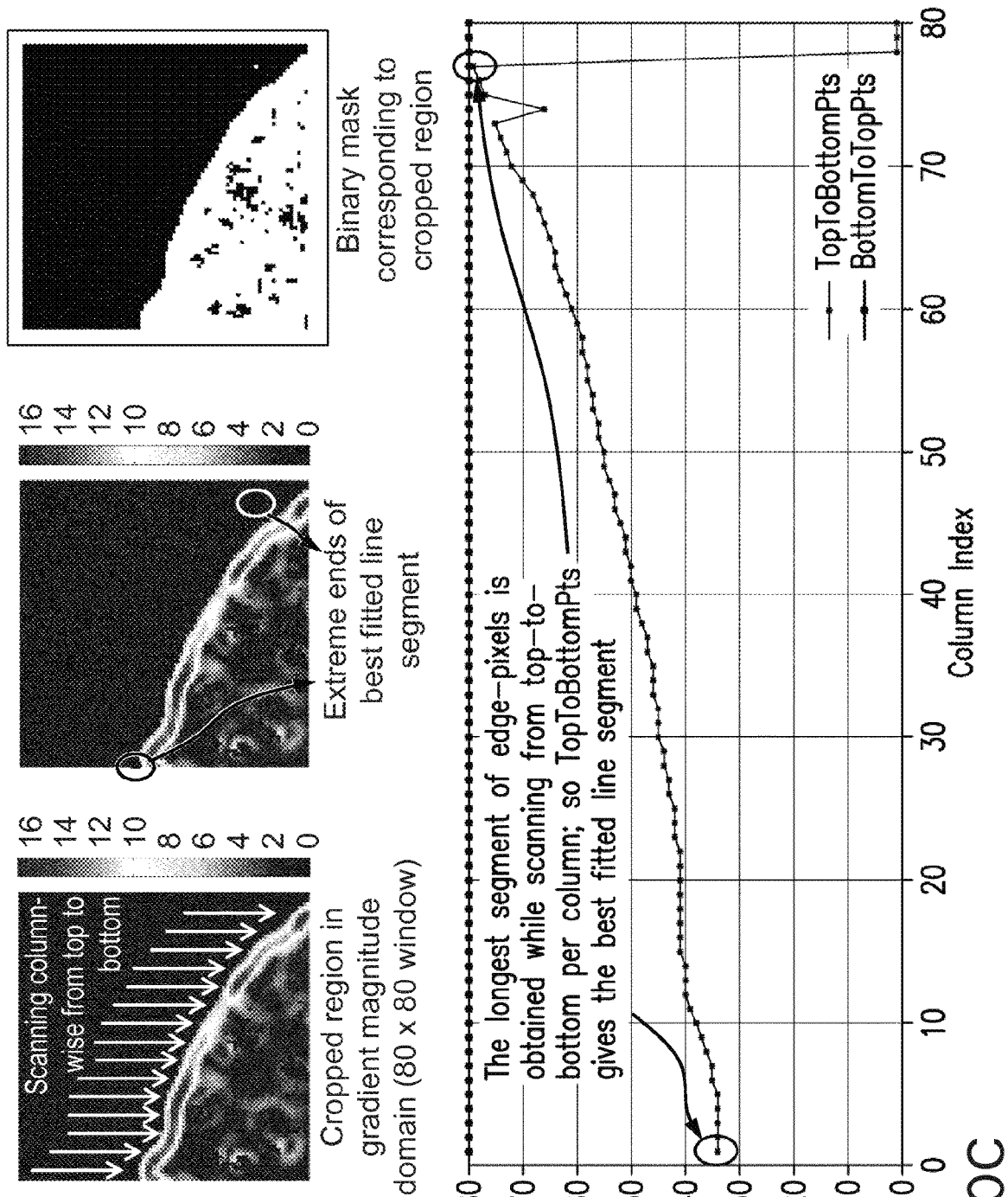
Figure 20D:
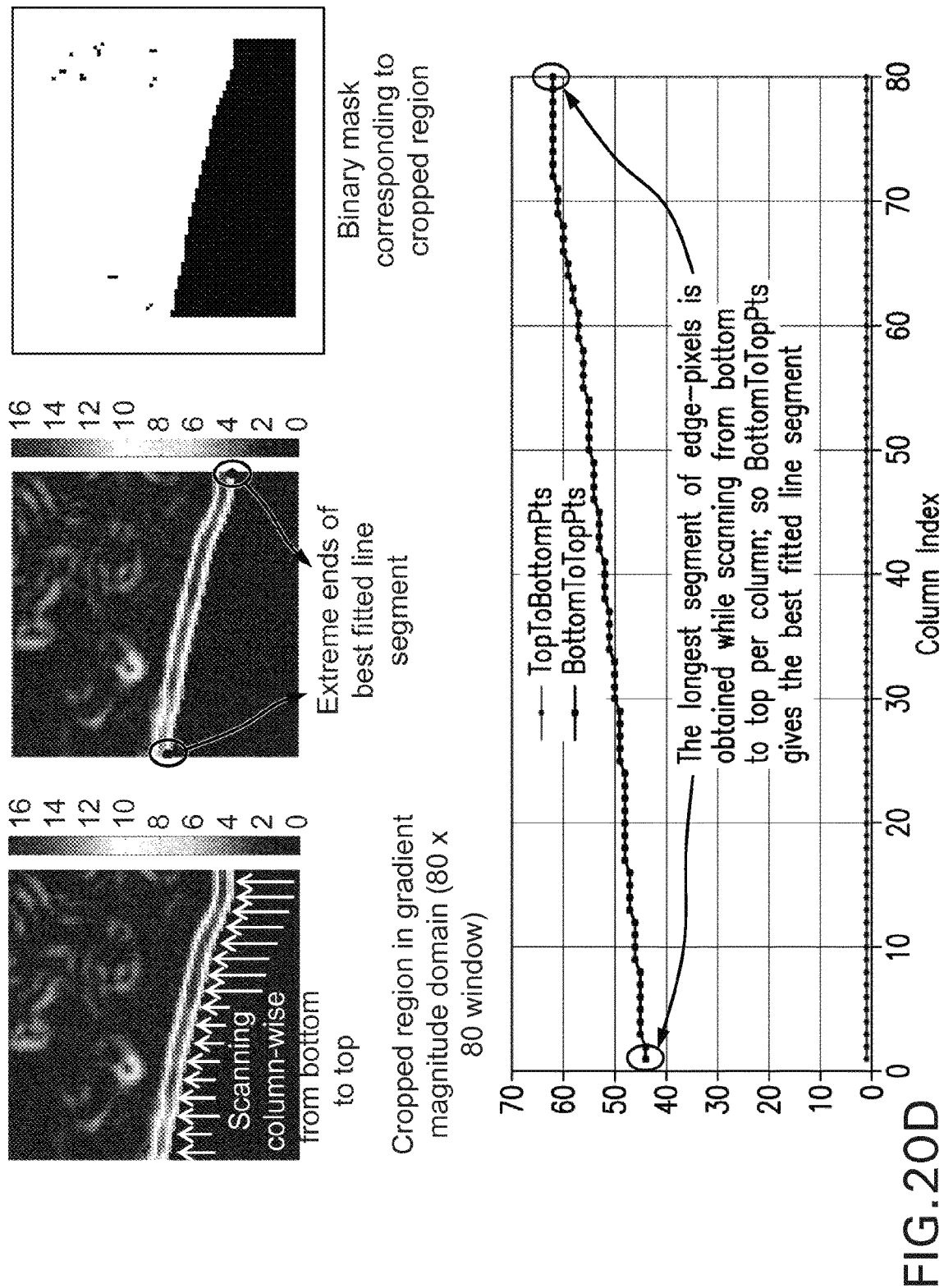

For each window, which are along the boundary, line-based features are computed. Given a certain window, each row of the window is considered. For example, for the ith row, LeftToRightPts(i) are defined as the leftmost column which has an ON pixel (foreground pixel) (an ON pixel in a binary image is a pixel with value of 1 while the OFF pixels are those with value of 0), as shown in FIG. 20B. For the ith row, RightToLeftPts(i) are defined as the rightmost column of the considered window which has an ON pixel (foreground pixel) as shown in FIG. 20A. Similarly, each column is considered in turn. For the ith column, TopToBottomPts(i) is defined as the topmost row which has an ON foreground pixel as shown in FIG. 20C. For the ith column, BottomToTopPts(i) is defined as the bottommost row which has an ON foreground pixel as shown in FIG. 20D.

In the described model, the objective is to see whether the best fitting line for a given window, lying near the boundary, is given by a sequence of leftmost edge points along each row (given by LeftToRightPts), or by rightmost edge points along each row (given by RightToLeftPts), or by topmost edge points along each column (given by TopToBottomPts) or by the bottommost edge points along each column (given by BottomToTopPts). Then, for every case, consideration is given to which case gives the maximum length interval, i.e. the maximum number of consecutive points, based on the understanding that the dominant edge direction (representing the boundary pixels for the considered windowed region) can be expressed by points along one of these four edges—leftmost edge, rightmost edge, topmost edge, or bottommost edge.

Examples of computing the line based on these edge points is shown in FIGS. 20a-d. Specifically, in the embodiment of FIG. 20, for each 80×80 sized window, let there be N boundary points ($\{(x_i, y_i)\}$, i=1, 2, . . . , N are the set of N points). For every two points, a line segment model can be computed. We perform a random sampling of the points (for example according to M. Fischler and R. Bolles, "Random sample consensus: a paradigm for model fitting with applications to image analysis and automated cartography, *Communications of the ACMI*, vol. 24, no. 6, pp. 381-395, 1981, which is herein incorporated by reference in its entirety) of the points and compute the line segment model for a given pair of selected points. If the model is proper enough, then it will hold true for a large majority of the points. For example, for two given points $(x_m, y_m)$ and $(x_n, y_n)$, let the slope of the computed line segment be $M_{m,n}$ and the y-intercept be $C_{m,n}$. For all the input boundary points, if we assume this line-based model, then, for the x-coordinates $\{x_i\}$, i=1, 2, . . . , N, the corresponding y-coordinates $\{y_i\}$, i=1, 2, . . . , N can be computed as $y'_i = M_{m,n}(x_i) + C_{m,n}$. In other words, if $\{(x_i, y_i)\}$, i=1, 2, . . . , N are the set of N points obtained from the boundary region of the windowed region under consideration, and a line segment is computed using the $m^{th}$ and $n^{th}$ points $(x_m, y_m)$ and $(x_n, y_n)$, and let the computed line model be represented by $y = M_{m,n}x + C$ (here the slope of the fitting line is given by $M_{m,n}$ and the y-intercept of the line is given by C); then all the points $\{x_i\}$, i=1, 2, . . . , N are transformed using this line model given by $M_{m,n}$ and C, and let $y'_i=M_{m,n}(x_i)+C$. The cost of fitting the line model is given by "dist"=$\Sigma|y_i-y'_i|$, summed over i=1, 2, . . . , N. The line-parameter set which produces the smallest value of "dist" (Equation A) (in this random sampling process, various pairs of line segments are considered, and a fitting cost termed as "dist" is computed in each case; out of all these cases, the line segment pair which yields the lowest value of "dist" is used to return the best line fitting for the entire boundary region for the window under consideration) is selected as the best line-parameter set and the line points which lie very close to the predicted line model (within two units of distance) are considered and the extreme points are used to represent the two extreme ends of the line segment. A line model is represented by for example, 5 numbers—(x-y coordinates of the starting point along line segment), (x-y coordinates of the ending point along line segment), and (sum of the gradient magnitude values along the points lying on the line segment).

In some cases, for a given window, a single line segment may not be a good fit, for example if there are two or more dominant directions, as shown in FIG. 20E, wherein both top-to-bottom scanning and right-to-left scanning yield significantly long line segments. In such cases, it may be difficult to represent the boundary region using a single line segment model and hence, we refrain on imposing a line model for such regions. The line segment model is computed for those boundary regions where a single line segment can properly capture the boundary region.

In some embodiments, a computed line segment is considered significant if the set of points well fitted by the line (Equation B) covers more than half of the boundary points (Equation C). For a given window, a single line segment may not be a good fit if there are two/more dominant directions.

$$\{m^*, n^*\} = \underset{m,n}{\mathrm{argmin}} \sum_{i=1}^{N} |y_i - (M_{m,n}x_i + C_{m,n})| \quad \text{(EQ. A)}$$

$$P = \{i : |M_{m^*,n^*}x_i + C_{m^*,n^*}| \le 2\} \quad \text{(EQ. B)}$$

IF $|P| > \dfrac{N}{2}$, fitted line is significant. (EQ. C)

The extreme ends of P (EQ. B) are used to represent the line segment. A line segment, stretching from $(x_1,y_1)$ to $(x_2,y_2)$ is represented by the three terms discussed below.

A computed line segment is considered significant if the set of points well fitted by the line (set of points, which fall within 2 units of distance of the best fitting line model for that window) covers more than half of the boundary points. Thus, when we have a single dominant direction, then the best fitted line segment will have >50% of the boundary points being close to it (within 2 units of distance)—hence, we fit a single line model only when the best fitted line segment can accommodate/fit more than 50% of the boundary points. This model has been empirically determined through experimentation and it rejects those regions where there is ambiguity about fitting a "single" line model for all the boundary points, where the rule for rejection is mentioned in the previous sentence. The set of computed line segments should be such that they represent the boundary portion of windowed regions; and avoiding computing line-segments for the windowed regions where there is ambiguity about a single fitted line helps the subsequent line-matching step in reducing the number of false matches.

Figure 25:
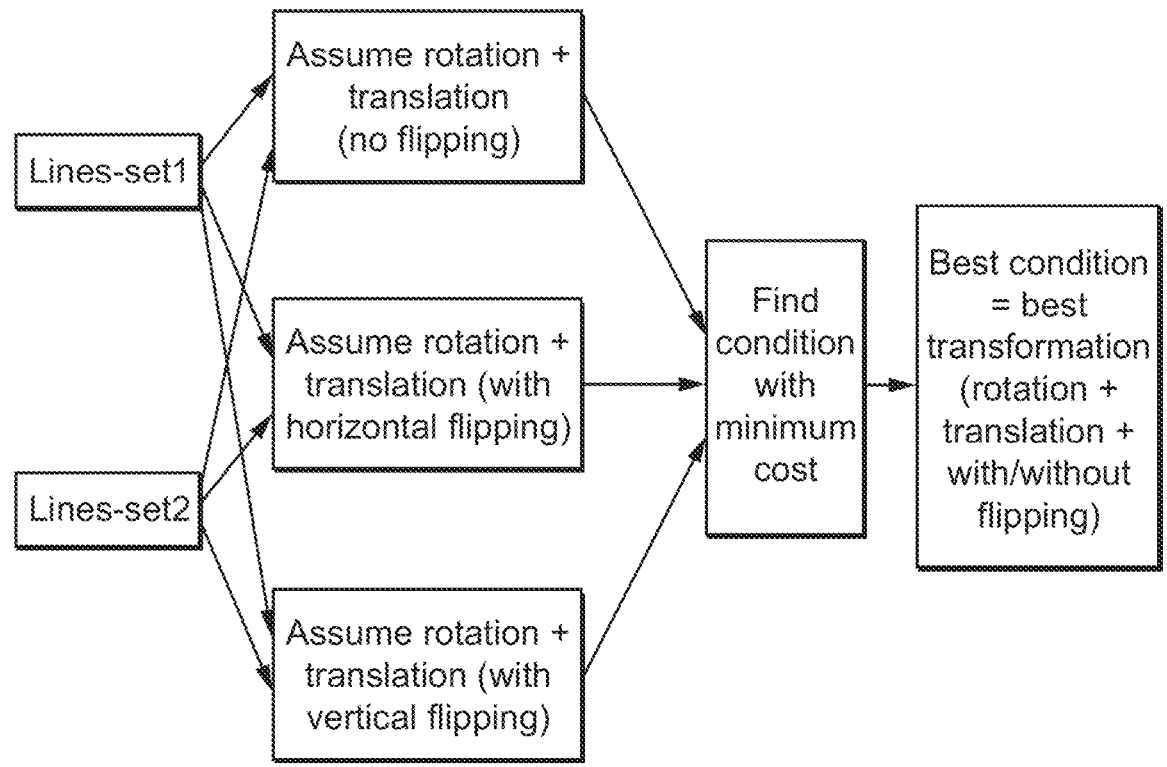
FIG. 25 is a flow diagram of an embodiment of a global registration process which may be part of the method of FIG. 12.

FIGS. 25 and 26 illustrate further details of block 612c, providing an embodiment of a method for computing transformation parameters between two sets of line features. As shown in FIG. 25, and as described in 1) to 3) below, in some embodiments, transformation parameters are estimated for three cases, for each of which rotation (AO), and shifts ($\Delta x$, $\Delta y$) are computed (i.e., in each case, we assume that the tissue can be subjected to rotation and translation, along the x and y axes, wherein "translation" below is shorthand for "translation along x axis and translation along y axis"):
  1) rotation+translation (this first case assumes the tissue has not been flipped);
  2) horizontal flip+rotation+translation (this second case assumes the tissue has undergone a horizontal or left-to-right flip);
  3) vertical flip+rotation+translation (this third case assumes the tissue has undergone a vertical or top-to-bottom flip).

In the illustrated embodiment, a line-matching based cost is computed for all the three cases, and the case which results in the best matching (minimum cost) is regarded as the transformation condition. For the selected transformation condition, the rotation ($\Delta\theta_{opt}$), and shifts ($\Delta x_{opt}, \Delta y_{opt}$) are returned. An aim is to obtain the translation ($\Delta x_{opt}, \Delta y_{opt}$) and rotation angle ($\Delta\theta_{opt}$); and also find the sub-part of image 1 which best matches to a sub-part of image 2. If among the stronger lines (a stronger line segment is one with a higher value of the sum of gradient magnitude, summed along its pixels), a pair of corresponding lines in images 1 and 2 can be found, then the shift and angle between these lines can be computed that explains the global registration.

More specifically, a line segment, stretching from $(x_1,y_1)$ to $(x_2,y_2)$, may be represented by three parameters:
  a) Line center=$(x_1+x_2)/2$, $(y_1+y_2)/2$
  b) Line angle=$\tan^{(-1)}((y_2-y_1)/(x_2-x_1))$
  c) Gradient strength M=sum of gradient magnitude values along the line.

Assume that there are $N_1$ lines for image 1 with line centers at $(x_{i1}, y_{i1})$, i=1, . . . , $N_1$ and line angles ($\theta_{i1}$) and strength ($M_{i1}$): the line segments are sorted in descending order of $\{M_{i1}\}$. Assume also that there are $N_2$ lines for image 2 with line centers at $(x_{i2}, y_{i2})$, i=1, . . . , $N_2$ and line angles ($\theta_{i2}$) and strength ($M_{i2}$): the line segments are sorted in descending order of ($M_{i2}$). With these assumptions, computation of line-matching cost for a given case (no flip, left-to-right flip and top-to-bottom flip) is provided by the following example:
  Consider top $T_1$ lines in image 1, and top $T_2$ lines in image 2 (e.g. in our experiments, we have empirically used $T_1$=min(50, number of lines in set 1) and $T_2$=min(50, number of lines in set 2))
  We construct a score matrix S is of size ($T_1 \times T_2 \times 2$), where we keep track of a matching cost for every line-pair in between the 2 sets of lines, and we consider 2 possible angles between 2 line segments (considering the 180° shifted version of the $2^{nd}$ line)
  We consider all ($T_1 \times T_2$) pairs and compute shifts and rotation angle for every pair of line-segments, while considering the top $T_1$ lines in set 1 and the top $T_2$ lines in set 2
  The matrix rotDiff contains the difference in angles between every possible line pair, in sets 1 and 2, where rotDiff(i,j)=$\theta_{i1}-\theta_{j2}$
  For i=1:$T_1$//here i=index of selected line in image 1
    For j=1:$T_2$//here j=index of selected line in image 2

Fork=1:2
    When k=1; dr=$\theta_{i1}-\theta_{j2}$
    When k=2; dr=$\theta_{i1}-(-sign(\theta_{j2})*(\Pi-|\theta_{j2}|))$ (considering the 180° shifted version of line 2)
    For each case, rotate all lines in set 1 by dr
    let transformed line centers of set 1 be $\{(x'_{i1},y'_{i1})\}$, i=1, . . . , $N_1$
    locDiffX(i,j)=$(x'_{i1})-x_{j2}$, locDiffY(i,j)=$y'_{i1}-y_{j2}$; dx=locDiffX(i,j); dy=locDiffY(i,j)
    DX=|locDiffX-dx|; DY=|locDiffY-dy|;
    DR=|rotDiff-dr| (limit values to [0, Π/2])
    sc=sqrt(DX.^2+DY.^2)+α*DR (empirically, α=⅓)
    S(i,j,k)=median of (minimum distance from every line center in set 1 to nearest transformed line center in set 2)
    Also, save the shifts (-dx,-dy) and rotation angle (dr)
    End for loop (k)
    End for loop (j)
End for loop (i)
From S, compute the minimum value $S_{min}$ and also record the corresponding shifts and angle
For all 3 conditions (without flip, with horizontal flip, or with vertical flip), find corresponding $S_{min}$, and record the condition which results in minimum $S_{min}$: the corresponding shifts=$(\Delta x_{opt}, \Delta y_{opt})$, while the corresponding angle=$(\Delta \theta_{opt})$.

The line-based model may have benefits as regards horizontal and vertical flip conditions in that it may only need to be computed once. More specifically, suppose image 1 is a M×N image, with M rows and N columns. Then, once the line model is computed for image 1, the same model can be easily extended to account for flipped versions of image 1. For example, a line is represented by start and end points and by the sum of gradient magnitudes. Since the effective line segment remains the same (only the coordinates of its constituent points changes), we need to recompute the start and end points while the sum of gradient magnitudes is constant. For example, for a horizontally flipped case, a point (x,y) in image 1 will get mapped to (N−1−x, y) in the grid of horizontally flipped version of image 1, where column indices are numbered as 0, 1, 2, . . . , N−1. For a vertically flipped case, a point (x,y) in image 1 will get mapped to (x,M−1−y) in the grid of vertically flipped version of image 1, where row indices are numbered as 0, 1, 2, . . . , M−1.

FIG. 26 illustrates the basic concepts of an embodiment of a fine registration process according to this disclosure where the search window is shown around the annotation region returned after coarse registration. Field of View 1 (FOV-1) marked by the user is mapped to window W1 in the transformed image 1 grid (image 1 is transformed using the transformation parameters returned after global transformation). Window W2 is obtained when window W1 in the transformed image 1 grid is directly mapped to the grid of image 2 (the slight mismatch is due to inaccuracy of global transformation). A window of the same size as window W1 is slid in the search window and a normalized correlation for each window location, between location W1 in image 1 and the current window in image 2, is computed.

Once we have computed the best transformation condition, as shown in FIG. 26, we may also utilize this information to compute which "subset" in image 1 matches well with which "subset" in image 2—this "subset" computation may permit successful alignment even when due to AOI mismatch in between the 2 images, there is a mismatch between the entire image 1 and the entire image 2—but there is a certain subset in image 1 which does match well with a certain subset in image 2. More specifically:

a) For points $(x_{i1}, y_{i1})$ in image 1, suppose it gets mapped to $(x'_{i1}, y'_{i1})$ after transformation. The key here is to select which points in image 1 are represented in image 2 after transformation: the bounding box, or the relevant subset in each image, is the enclosing rectangle for the set of corresponding points.
    b) For the transformed points which are also represented by points in image 2, the Euclidean distance between transformed line centers in image 1 and the nearest line centers in image 2 will be less than a certain threshold—i.e. $\{(x_{k1}, y_{k1})\}$ is a representative point if $$\min(\text{for all } i) d(\{x'_{k1}, y'_{k1}\}, \{x_{i2}, y_{i2}\}) <= 10.$$

c) For example, out of $N_1$ points in image 1, P is the set of $N_1'$ ($N_1'<=N_1$) points are such that after transformation, they are close to (<=10 units in Euclidean distance) corresponding points in image 2: P=$\{(x_{k1}, y_{k1})$: k is such that min (for all i) $d(\{x'_{k1},y'_{k1}\},\{x_{i2},y_{i2}\})$ <=10$\}$.
    d) Hence, the relevant bounding box B1 in image 1 is given by the $N_1'$ points in set P; while the relevant bounding box B2 in image 2 is given by its corresponding $N_1'$ points. Thus, the subset B1 in image 1 can be matched with the subset B2 in image 2. For example, in FIGS. 27A and 27B, the computed subsets are shown by rectangle 1 in FIG. 27A (subset B1 for image 1) and by rectangle 2 in FIG. 27B (subset B2 for image 2). Similarly, the marked rectangles in FIGS. 21A-C show how for AOI mismatched images, matching subsets can be returned as an output of the registration process.

The line-based method may also be used to transform an image given a certain rotation angle, translation terms along x and y axes and globally align both images. For example, suppose (x,y) is a point location in image 1 and we desire to rotate image 1 by θ and translate by dx and dy along x and y axes, respectively. Then, in the point (x,y) in the grid of image 1 will get mapped to (x',y') in the grid of transformed image 1 where:

$$[x' y' 1]^T = [\cos(\theta)-\sin(\theta) dx; \sin(\theta) \cos(\theta) dy; 0 0 1] * [x y 1]^T$$

where T denotes the transpose operator.

In cases where flipping occurs, it may be assumed that the flipping occurs first and then the rotation and translation parameters are computed. Suppose that image 1 is a M×N image (with M rows and N columns). When horizontal flip occurs, then a point (x,y) in the grid of image 1 gets mapped to (N−1−x, y) in the grid of horizontally flipped version of image 1—here we assume that column indices vary from 0, 1, 2, . . . , N−1. In this case, the total transformation equation is as follows:

$$[x' y' 1]^T = [\cos(\theta)-\sin(\theta) dx; \sin(\theta) \cos(\theta) dy; 0 0 1] * [(N-1-x) y 1]^T$$

In the case where vertical flipping occurs, a point (x,y) in the grid of image 1 gets mapped to (x,M−1−y) in the grid of vertically flipped version of image 1—here we assume that row indices vary from 0, 1, 2, . . . , M−1. In this case, the total transformation equation is as follows:

$$[x' y' 1]^T = [\cos(\theta)-\sin(\theta) dx; \sin(\theta) \cos(\theta) dy; 0 0 1] * [x (M-1-y) 1]^T$$

Figure 28:
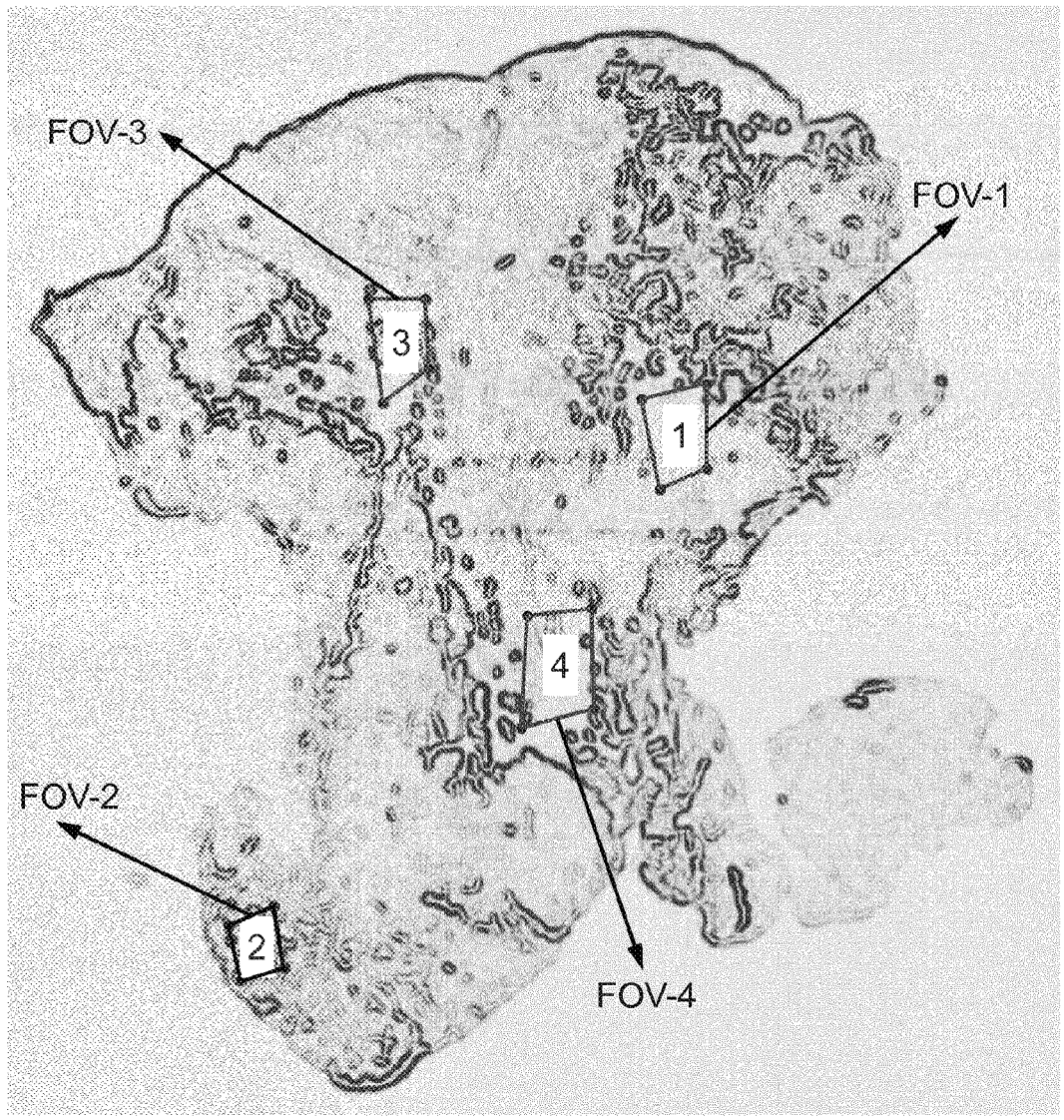
FIG. 28 illustrates the gradient magnitude image, computed from the grayscale version of a first color image, in a set of two adjacent tissue images.
Figure 29A:
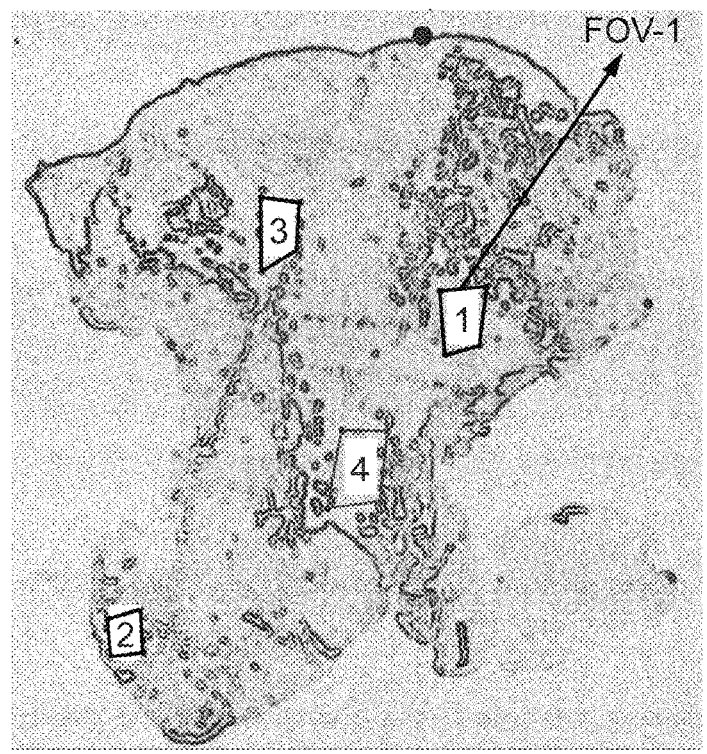
FIGS. 29A and 29B illustrate the gradient magnitude image of FIG. 1 after it has been transformed into the grid of image 2 side-by-side with gradient magnitude of image 2 with annotations mapped from the transformed image 1.
Figure 29B:
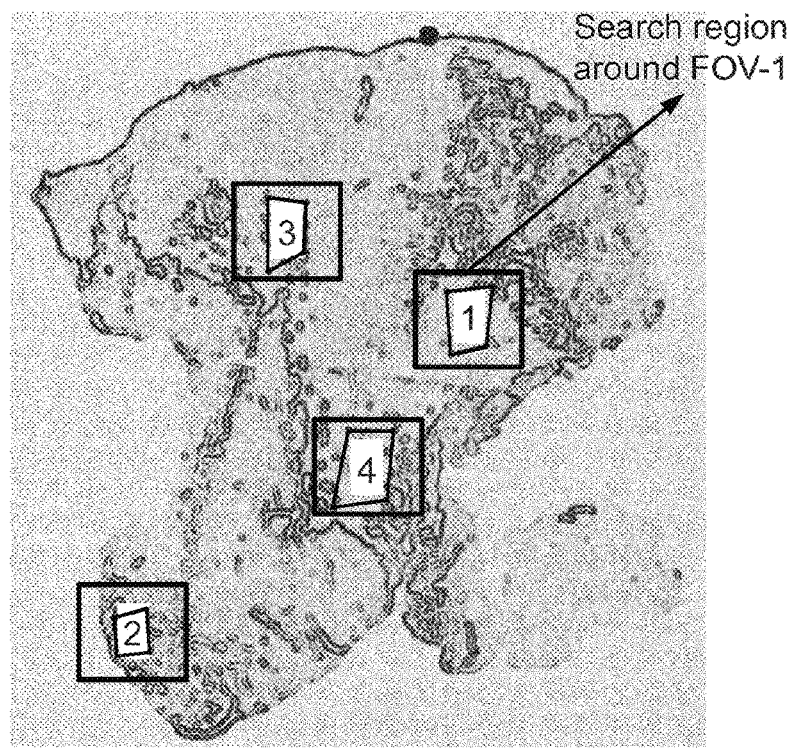
Figure 30:
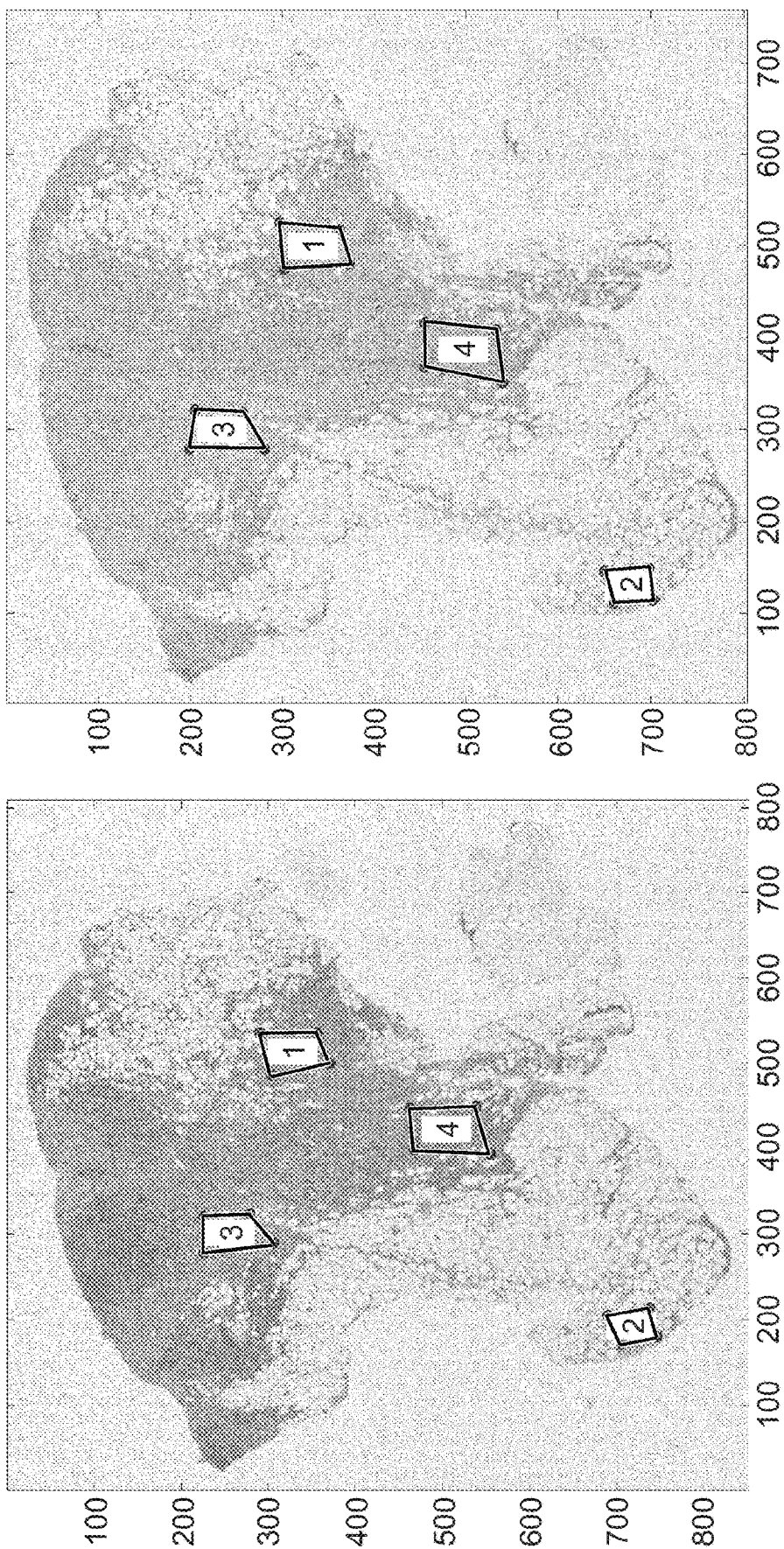
FIG. 30 illustrates a HE source image with several FOVs and an IHC target image with the recovered FOVs after a coarse registration in accordance with an embodiment of this disclosure.

Once the global transformation module is executed, the rotation, translation and reflection parameters (if any flipping is there), which explain the transformation between the images, may be obtained. In some embodiments, the $2^{nd}$ image is retained and the $1^{st}$ image is transformed using the above-mentioned transformation parameters. FIGS. 28 to 30 show how image 1 can be transformed so that it can be aligned on the same grid as image 2, in which FIG. 28 shows a gradient magnitude image 1 on the grid for image 1, FIG. 29A shows the gradient magnitude image 1 transformed and aligned to the grid of image 2, and FIG. 29B shows the points marked in image 1 recovered (transformed and mapped) in the gradient magnitude domain of image 2 in the grid of image 1. FIG. 30 shows the HE image corresponding to image 1 in FIG. 29A and the IHC image corresponding to image 2 in FIG. 29B, and how the points marked in the HE image are recovered in the IHC image after the coarse registration process described herein. The coarse matching method does not require the full high-resolution image; hence, for example, for registering two 20× whole slide images, their low resolution versions (for example, 1× images) may be considered for foreground estimation, line feature computation, and subsequent line-matching based transformation estimation.

Figure 33:
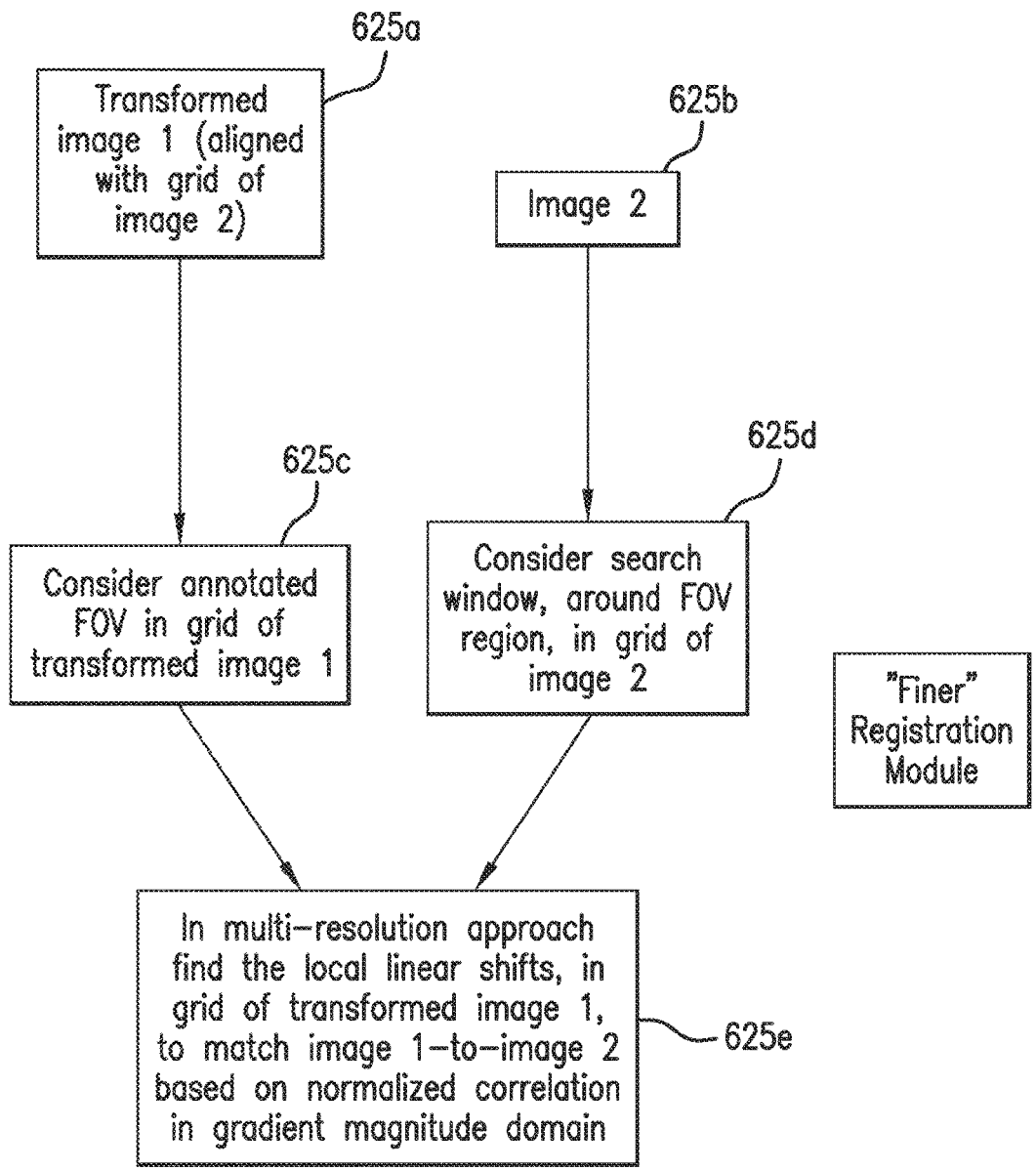
FIG. 33 is a flow diagram of an embodiment of a fine registration in accordance with this disclosure.

After aligning the two images on the same grid using a coarse registration process, a "finer" registration module identified by block 625 in FIG. 12 may be invoked, for example to improve the matching at higher resolutions. FIGS. 31 and 32 provide two different examples of registration results before (FIGS. 31A and 32A) and after (FIGS. 31B and 32B) invoking a fine registration process. FIG. 33 is a workflow diagram of an embodiment of a fine registration process which can be used as part of the image analysis devices, systems and methods of this disclosure.

As shown in FIG. 33, the exemplified fine registration module embodiment begins with the transformed image 1 (aligned with the grid of image 2) (block 625*a*) and image 2 (block 625*b*) and considers an annotated region in the grid of transformed image 1 (block 625*c*) (note that after transformation, transformed image 1 and image 2 are on the same grid) and a search window around the annotated region in the grid of image 2 (block 625*d*). A normalized, correlation-based measure is used as described below. We consider a window, of the same size as the annotation region marked in image 1, and this window is varied to cover all the possible locations inside the larger search window in image 2. For each combination of shifted sub-window inside the search window, a normalized correlation score is computed between the sub-window in image 2 and the fixed window in transformed image 1 (the fixed window location in transformed image 1 is obtained after coarse global registration where the 2 images are aligned) and the sub-window which produces the maximum normalized correlation score is chosen to represent the best localization in image 2 of the annotation region marked in image 1 (block 625*e*).

Figure 34B:
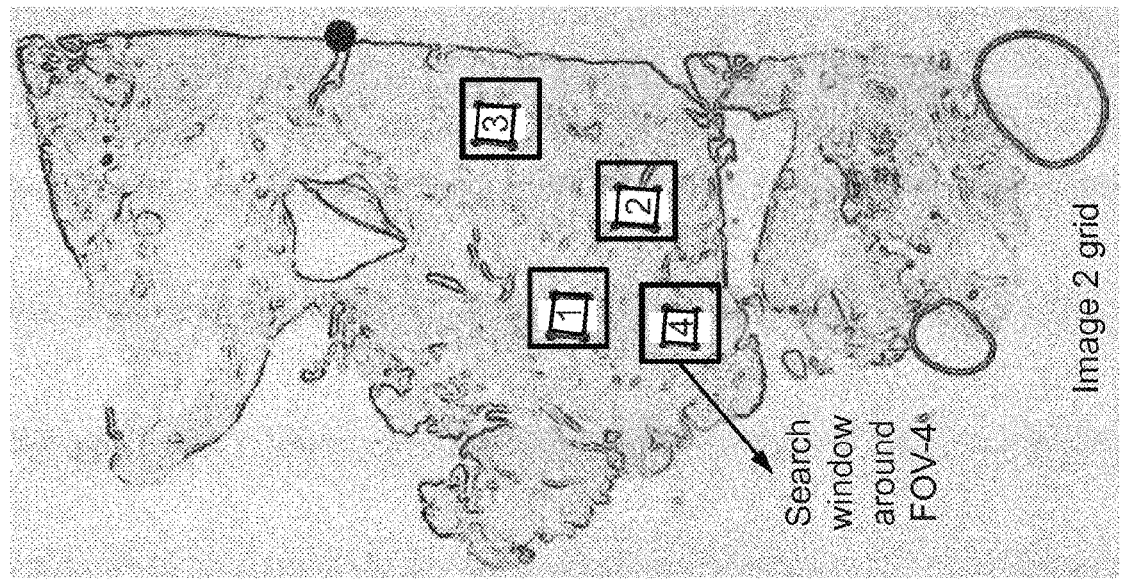
FIGS. 34A to 34D illustrate an implementation of a fine registration process in accordance with an embodiment of this disclosure—in the grid of transformed image 1, the user marked annotations are shown; in the grid of image 2, the search window around the retrieved annotation regions are shown where a detailed search is performed for finer registration. For both images, the gradient magnitude images are shown, where the gradient is computed based on the grayscale image obtained from the color image.
Figure 34A:
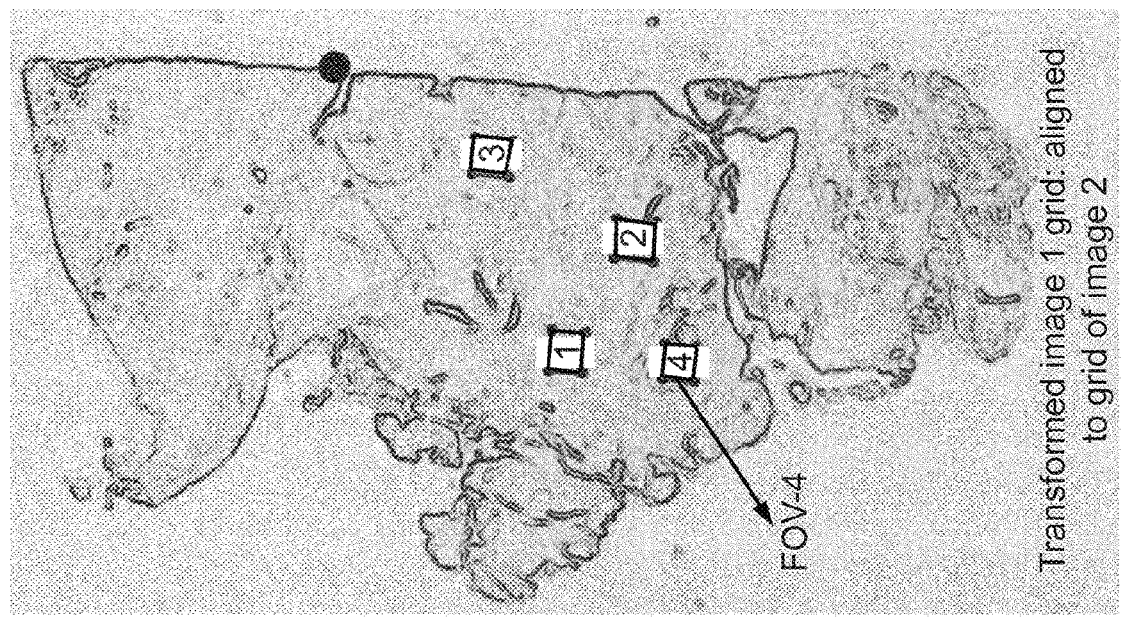

Examples of showing both image 1 aligned to the grid of image 2 and having a larger search window around each annotation region in the grid of image 2, are shown in FIGS. 34A and 34B. As shown, for the marked Fields of View ("FOV"s or "annotations"), we map them to the transformed image grid (FIG. 34A), and then consider a certain window around it in image 2 (denoted by black rectangles in FIG. 34B). Normalized correlation is used in the gradient magnitude domain to match the FOVs used in FIG. 34A to the shifted windows obtained in the search regions, as in FIG. 34B. In some embodiments, the maximum of the correlation matching based search is found robustly—once the top five maxima points are obtained, the standard deviation of their x-y locations is considered and if it is less than a certain threshold (e.g. 3 pixels) in both dimensions, it indicates that all 5 maxima are placed closely enough—then only the maximum location is used.

The search for the best matching window takes place in a multi-resolution approach and with each resolution, in some embodiments, the search window is halved to reduce the computational complexity. In other words, because the size of the area doubles when moving from 1× to 2×, the template window size is reduced by half to reduce the search time. For example, if a search window of 40 pixels (on each size of the annotation region at 1×) is used at resolution=1×, then once the best matching window is localized in 1×, a search of window 40/2=20 pixels (on either side of annotation region at 2×) is used at resolution 2×. As explained in the previous sentence, a search window size is divided into smaller portions, for example, halved in each step to reduce the computation complexity—hence a search window of 40 pixels at a certain resolution is reduced to 20 pixels when we proceed to the next higher resolution. Similarly, the search window is reduced to 20/2=10 pixels at 4× and 10/2=5× at 10×. Usefulness of the second-pass matching is shown in FIGS. 31 and 32.

Figure 34D:
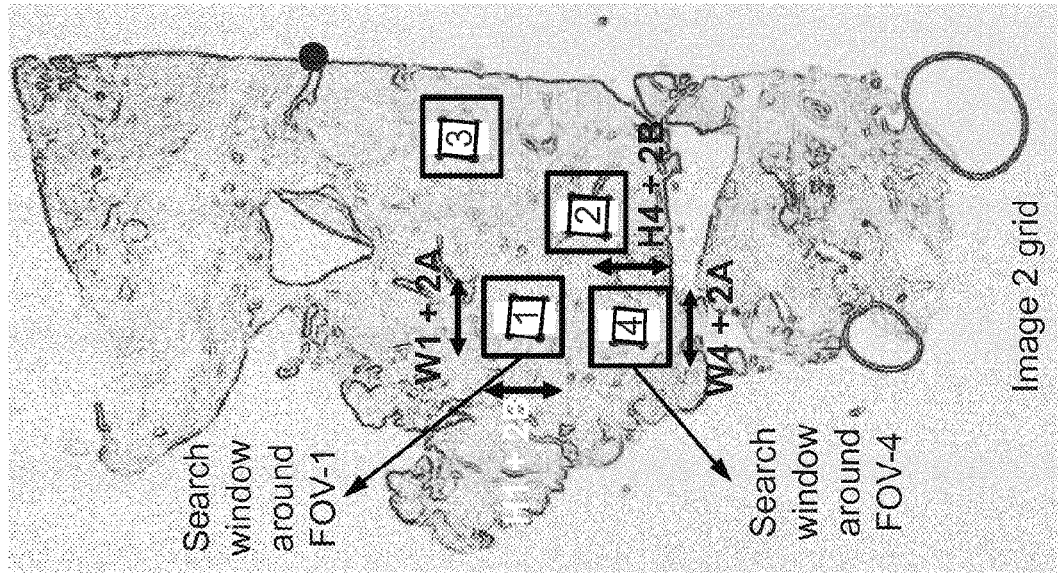
Figure 34C:
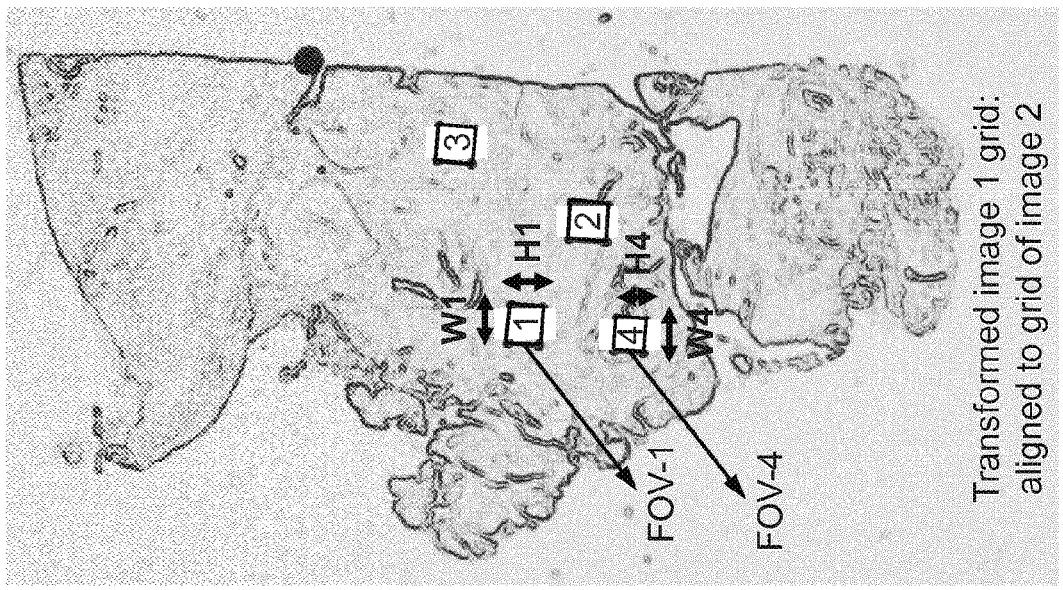

As another example of this concept of using a larger search window to allow for shifting of the retrieved annotation returned after global transformation is shown in FIGS. 34C and 34D. As is suggested, a region W1 is located in image 1. If we allow a search region of (+—A pixels along the x-axis) and (+—B pixels along the y axis), then, we have (2A+1)×(2B+1) possible candidate windows in image 2 which can match with window W1 in image 1. Here, the variables A and B have been used only as examples to describe that the search window is larger than the annotation window, and the extent to which the search window is larger than the annotation window, it is governed by the 2 variables A and B—in our experiments, we have used A and B as 75 pixels. For each case, we compute a normalized correlation based score which compares the gradient magnitude image in window W1 of image 1 with the corresponding window in image 2. The window configuration which returns the maximum normalized correlation score (i.e., the window for which there is best normalized correlation between the annotation window and the corresponding window within the larger search window, while performing normalized correlation between the two gradient magnitude images) is returned. In other words, each window configuration includes its location (e.g., top-left corner (x,y)) and the size. Once a window configuration gives the highest normalized correlation score, we output this (x,y) and window size as the found location of the searching template window from another image. The output location and the location of the template window from another define a pair of (x,y) correspondence for registration.

A number of embodiments have been described but a person of skill understands that still other embodiments are encompassed by this disclosure. It will be appreciated by those skilled in the art that changes could be made to the embodiments described above without departing from the broad inventive concepts thereof. It is understood, therefore, that this disclosure and the inventive concepts are not limited to the particular embodiments disclosed, but are intended to cover modifications within the spirit and scope of the inventive concepts including as defined in the appended claims. Accordingly, the foregoing description of various embodiments does not necessarily imply exclusion. For example, "some" embodiments or "other" embodiments may include all or part of "some", "other," "further," and "certain" embodiments within the scope of this invention.

The invention claimed is:

1. A method comprising:
generating a first set of line segments corresponding to at least part of a first tissue section depicted in a first image;
generating a second set of line segments corresponding to at least part of a second tissue section depicted in a second image, wherein the first tissue section includes one or more mismatching regions relative to corresponding regions of the second tissue section;
identifying a first subset of the first set of line segments, wherein the first subset includes line segments that are determined to be capable of being matched to corresponding line segments of a second subset of the second set of line segments, wherein a line segment of the first subset is represented by a line-center value, a line-angle value, and a gradient-strength value, wherein the gradient-strength value is generated based on a sum of gradient magnitude across the line segment;
determining that a count of line segments corresponding to the first subset exceeds a predetermined threshold; and
in response to determining that the count of line segments corresponding to the first subset exceed the predetermined threshold, generating, based on the first subset of line segments, one or more transformation parameters for performing a first alignment operation to align the first image to the second image.

2. The method of claim 1, wherein the first alignment operation includes applying the one or more transformation parameters to align the first image to a common grid generated from the second image.

3. The method of claim 1, further comprising:
performing, based on the one or more transformation parameters, the first alignment operation to align the first image to the second image; and
in response to performing the first alignment operation, transferring an annotation at a particular location of the first image to a corresponding location of the second image.

4. The method of claim 1, wherein generating the one or more transformation parameters includes:
for each line segment of the first subset:
determining a rotation sub-parameter and a shift sub-parameter between the line segment of the first subset and a corresponding line segment of the second subset; and
generating a line-matching cost of the line segment based on the rotation sub-parameter and the shift sub-parameter;
selecting a line segment of the first subset having a minimum line-matching cost; and
generating, based on the selected line segment, a transformation condition for generating the one or more transformation parameters.

5. The method of claim 1, wherein the one or more mismatching regions include an inserted sub-region, a deleted sub-region, and/or a flipped sub-region.

6. The method of claim 1, further comprising:
performing, based on the one or more transformation parameters, the first alignment operation to align the first image to the second image, thereby generating an aligned first image;
identifying a first window region of the aligned first image and a second window region of the second image;
determining a normalized correlation score between the first window region and the second window region; and
performing a second alignment operation by applying the normalized correlation score to the aligned first image.

7. A system comprising:
one or more data processors; and
a non-transitory computer readable storage medium containing instructions which, when executed on the one or more data processors, cause the one or more data processors to perform operations comprising:
generating a first set of line segments corresponding to at least part of a first tissue section depicted in a first image;
generating a second set of line segments corresponding to at least part of a second tissue section depicted in a second image, wherein the first tissue section includes one or more mismatching regions relative to corresponding regions of the second tissue section;
identifying a first subset of the first set of line segments, wherein the first subset includes line segments that are determined to be capable of being matched to corresponding line segments of a second subset of the second set of line segments, wherein a line segment of the first subset is represented by a line-center value, a line-angle value, and a gradient-strength value, wherein the gradient-strength value is generated based on a sum of gradient magnitude across the line segment;
determining that a count of line segments corresponding to the first subset exceeds a predetermined threshold; and
in response to determining that the count of line segments corresponding to the first subset exceed the predetermined threshold, generating, based on the first subset of line segments, one or more transformation parameters for performing a first alignment operation to align the first image to the second image.

8. The system of claim 7, wherein the first alignment operation includes applying the one or more transformation parameters to align the first image to a common grid generated from the second image.

9. The system of claim 7, wherein the instructions further cause the one or more data processors to perform operations comprising:
performing, based on the one or more transformation parameters, the first alignment operation to align the first image to the second image; and
in response to performing the first alignment operation, transferring an annotation at a particular location of the first image to a corresponding location of the second image.

10. The system of claim 7, wherein generating the one or more transformation parameters includes:
for each line segment of the first subset:
determining a rotation sub-parameter and a shift sub-parameter between the line segment of the first subset and a corresponding line segment of the second subset; and
generating a line-matching cost of the line segment based on the rotation sub-parameter and the shift sub-parameter;
selecting a line segment of the first subset having a minimum line-matching cost; and
generating, based on the selected line segment, a transformation condition for generating the one or more transformation parameters.

11. The system of claim 7, wherein the one or more mismatching regions include an inserted sub-region, a deleted sub-region, and/or a flipped sub-region.

12. The system of claim 7, wherein the instructions further cause the one or more data processors to perform operations comprising:
- performing, based on the one or more transformation parameters, the first alignment operation to align the first image to the second image, thereby generating an aligned first image;
- identifying a first window region of the aligned first image and a second window region of the second image;
- determining a normalized correlation score between the first window region and the second window region; and
- performing a second alignment operation by applying the normalized correlation score to the aligned first image.

13. A computer-program product tangibly embodied in a non-transitory machine-readable storage medium, including instructions configured to cause one or more data processors to perform operations comprising:
- generating a first set of line segments corresponding to at least part of a first tissue section depicted in a first image;
- generating a second set of line segments corresponding to at least part of a second tissue section depicted in a second image, wherein the first tissue section includes one or more mismatching regions relative to corresponding regions of the second tissue section;
- identifying a first subset of the first set of line segments, wherein the first subset includes line segments that are determined to be capable of being matched to corresponding line segments of a second subset of the second set of line segments, wherein a line segment of the first subset is represented by a line-center value, a line-angle value, and a gradient-strength value, wherein the gradient-strength value is generated based on a sum of gradient magnitude across the line segment;
- determining that a count of line segments corresponding to the first subset exceeds a predetermined threshold; and
- in response to determining that the count of line segments corresponding to the first subset exceed the predetermined threshold, generating, based on the first subset of line segments, one or more transformation parameters for performing a first alignment operation to align the first image to the second image.

14. The computer-program product of claim 13, wherein the first alignment operation includes applying the one or more transformation parameters to align the first image to a common grid generated from the second image.

15. The computer-program product of claim 13, further comprising:
performing, based on the one or more transformation parameters, the first alignment operation to align the first image to the second image; and
- in response to performing the first alignment operation, transferring an annotation at a particular location of the first image to a corresponding location of the second image.

16. The computer-program product of claim 13, wherein generating the one or more transformation parameters includes:
for each line segment of the first subset:
- determining a rotation sub-parameter and a shift sub-parameter between the line segment of the first subset and a corresponding line segment of the second subset; and
- generating a line-matching cost of the line segment based on the rotation sub-parameter and the shift sub-parameter;
selecting a line segment of the first subset having a minimum line-matching cost; and
generating, based on the selected line segment, a transformation condition for generating the one or more transformation parameters.

17. The computer-program product of claim 13, further comprising:
- performing, based on the one or more transformation parameters, the first alignment operation to align the first image to the second image,
- thereby generating an aligned first image; identifying a first window region of the aligned first image and a second window region of the second image;
- determining a normalized correlation score between the first window region and the second window region; and
- performing a second alignment operation by applying the normalized correlation score to the aligned first image.

* * * * *